(12) United States Patent
Aerts et al.

(10) Patent No.: US 9,056,847 B2
(45) Date of Patent: Jun. 16, 2015

(54) ACTIVITY BASED PROBES (ABPS) INTERACTING WITH GLYCOSIDASES

(75) Inventors: Johannes Maria Franciscus Gerardus Aerts, Abcoude (NL); Herman Steven Overkleeft, Leiden (NL)

(73) Assignee: ACADEMISCH MEDISCH CENTRUM BIJ UNIVERSITEIT VAN AMSTERDAM, Amsterdam (NL)

( * ) Notice: Subject to any disclaimer, the term of this patent is extended or adjusted under 35 U.S.C. 154(b) by 199 days.

(21) Appl. No.: 13/583,193

(22) PCT Filed: Mar. 10, 2011

(86) PCT No.: PCT/NL2011/050164
§ 371 (c)(1),
(2), (4) Date: Feb. 25, 2013

(87) PCT Pub. No.: WO2011/112085
PCT Pub. Date: Sep. 15, 2011

(65) Prior Publication Data
US 2013/0143228 A1      Jun. 6, 2013

(30) Foreign Application Priority Data

Mar. 10, 2010   (EP) .................................. 10156139.7

(51) Int. Cl.
| | | |
|---|---|---|
| *C12Q 1/34* | (2006.01) | |
| *C07D 303/14* | (2006.01) | |
| *C07K 1/22* | (2006.01) | |
| *G01N 33/68* | (2006.01) | |
| *C07D 203/26* | (2006.01) | |
| *C07D 303/36* | (2006.01) | |
| *C07F 5/02* | (2006.01) | |

(52) U.S. Cl.
CPC ............... *C07D 303/14* (2013.01); *C07K 1/22* (2013.01); *C12Q 1/34* (2013.01); *G01N 33/6842* (2013.01); *G01N 2333/924* (2013.01); *G01N 2500/04* (2013.01); *G01N 2800/042* (2013.01); *C07D 203/26* (2013.01); *C07D 303/36* (2013.01); *C07F 5/025* (2013.01)

(58) Field of Classification Search
CPC .. C07D 303/14; C07D 303/36; C07D 203/26; C12Q 1/34
See application file for complete search history.

(56) References Cited

FOREIGN PATENT DOCUMENTS

| WO | 2004/079370 A1 | 9/2004 |
| WO | 2004079370 | 9/2004 |
| WO | 2008/054947 A2 | 5/2008 |
| WO | 2008054947 | 5/2008 |

OTHER PUBLICATIONS

International Search Report for PCT/NL2011/050164 Mailed August 23, 2011.
Hekmat O. et al., "Active-site Peptide "Fingerprinting" of Glycosidases in Complex Mixtures by Mass Spectrometry: Discovery of a Novel Retaining [beta]-1,4-Glycanase in Cellulomonas FIMI," Journal of Biology Chemistry; The American Society for Biochemistry and Molecular Biology, Inc., vol. 280, No. 42, pp. 35126-35135, Oct. 21, 2005.
Vocadlo D. J. et al., "A Strategy for funcational proteomic analysis of glycosidase activity from cell lysates," Angewandte Chemie-International Edition 20041011 Wiley-VCH Verlag DE, vol. 43, No. 40, Oct. 11, 2004, pp. 5338-5342, XP002590729.
Witte M. D. et al., "Ultrasensitive in situ visualization of active glucocerebrosidase molecules," Nature Chemical Biology 2010 Publishing Group GBR LNKD-DOI: 10.1038/NCHEMBIO.466, vol. 6, No. 12, Dec. 2010, pp. 907-913, XP002633316.
Nakata M. et al., "A Family of cyclophellitol analogs: synthesis and evaluation," Journal OD Antibiotics 1993, JP vol. 46, No. 12, 1993, pp. 1919-1922, XP008137556.
European Search Report dated Nov. 13, 2013, issued in Application No. 11 712 027.9-1405.

*Primary Examiner* — Karen Cochrane Carlson
(74) *Attorney, Agent, or Firm* — Miles & Stockbridge P.C.

(57) ABSTRACT

An activity based probe (ABP) comprising a glycosidase inhibitor, and a detection-group. The ABPs of the inventions are used for diagnosing storage disorder for screening of compounds suitable for preventing and/or treating a storage disorder, for monitoring of therapeutic enzymes for lysosomal storage disorders, and for ultra-sensitive visualization of glycosidase-fusion proteins in molecular imaging.

13 Claims, 68 Drawing Sheets

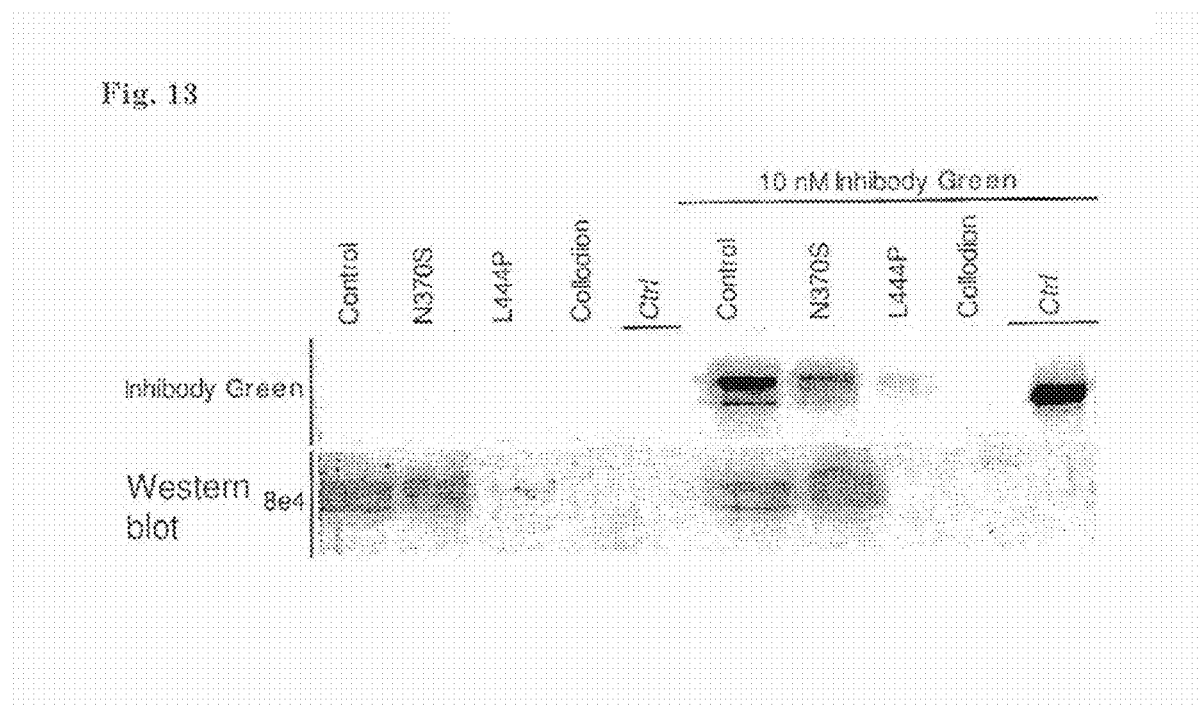

Fig. 16. Additional ABPs for GBA1.

Isofagomine 1

Fig. 22
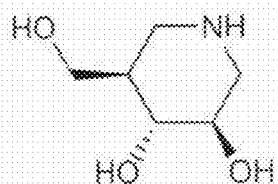
Compound 1
Isofagomine
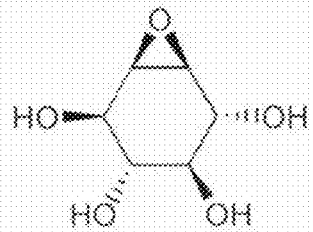
Compound 2
Conduritol B epoxide
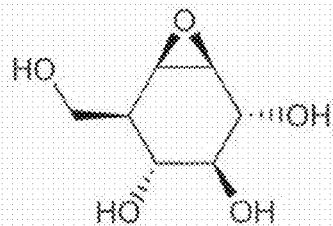
Compound 3
Cyclophellitol
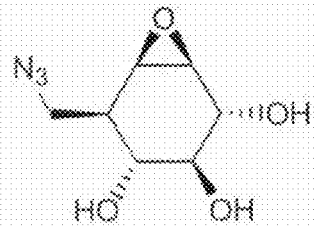
Compound 4
KY170
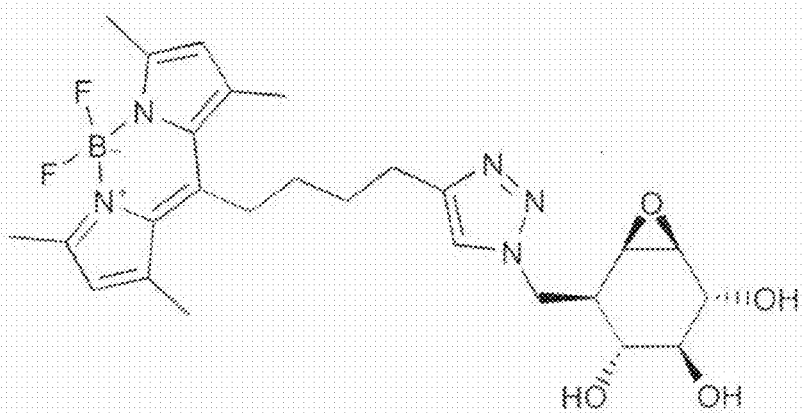
Compound 5
MDW933

Fig. 22, cont'd
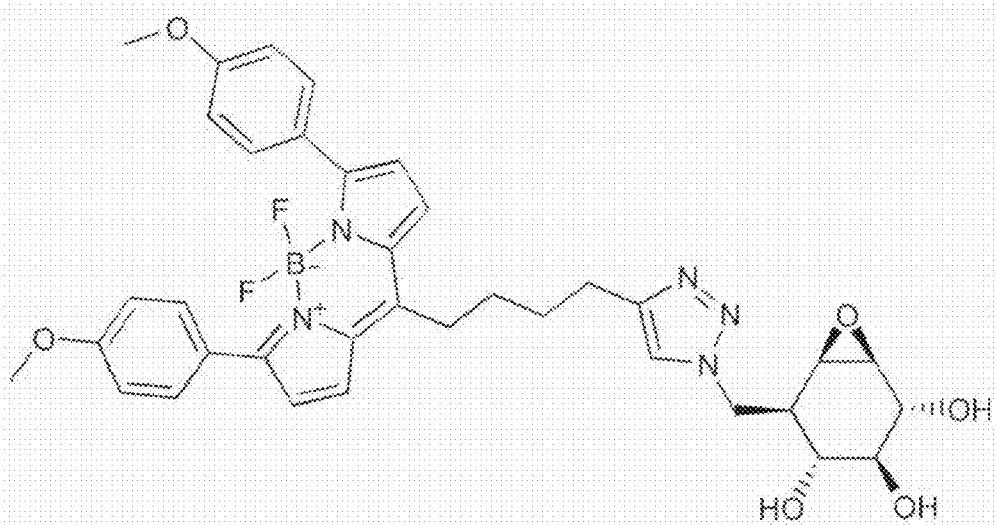
Compound 6
MDW941
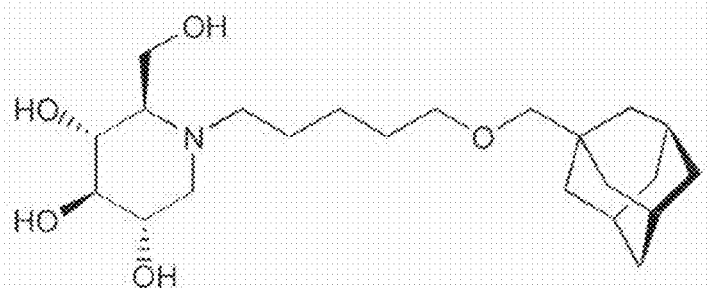
Compound 7
AMP-DNM

Fig. 22, cont'd
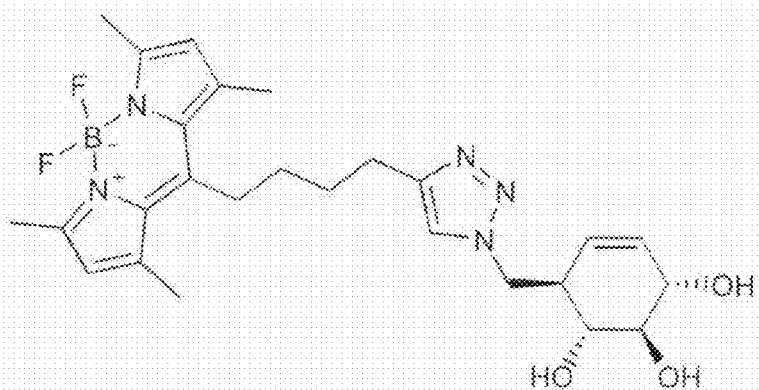
Compound 8
MDW1064
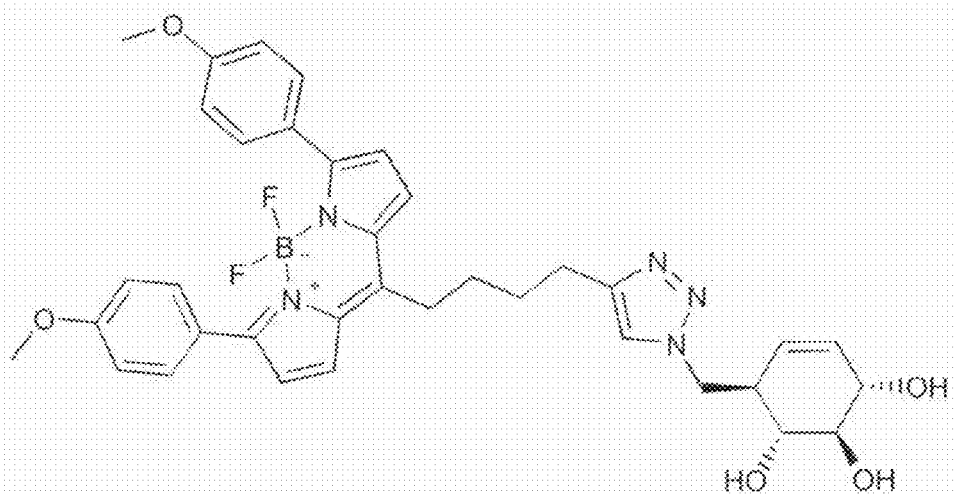
Compound 9
MDW1065

Fig. 22, cont'd
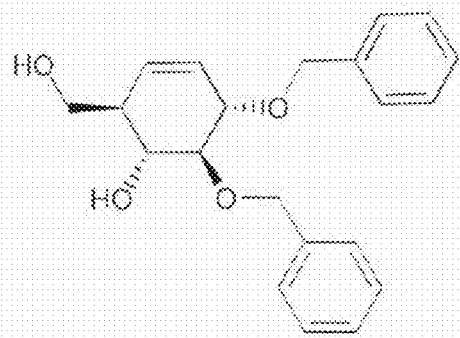
Compound 10
(1*R*,2*R*,5*S*,6*S*)-2-Hydroxymethyl)-5,6-bis(benzyloxy)cyclohex-3-enol
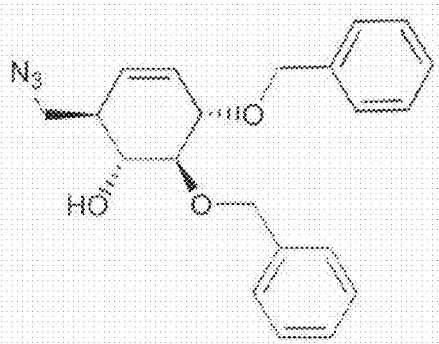
Compound 11
(1*R*,2*R*,5*S*,6*S*)-2-(Azidomethyl)-5,6-bis(benzyloxy)cyclohex-3-enol
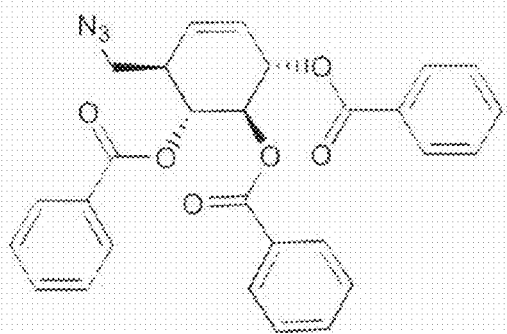
Compound 12
(1*R*,2*R*,3*S*,6*R*)-6-(Azidomethyl)cyclohex-4-ene-1,2,3-triyl tribenzoate Fig. 22, cont'd
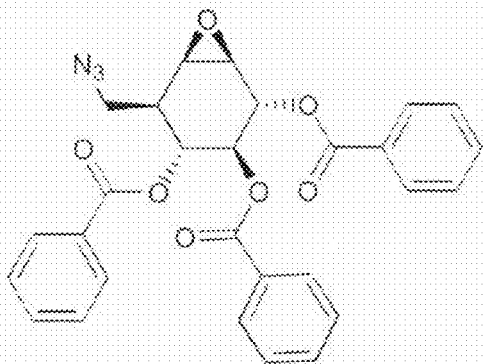
Compound 13
(1R,2S,3S,4R,5S,6R)-5-(Azidomethyl)-7-oxabicyclo[4.1.0]heptane-2,3,4-triyl tribenzoate
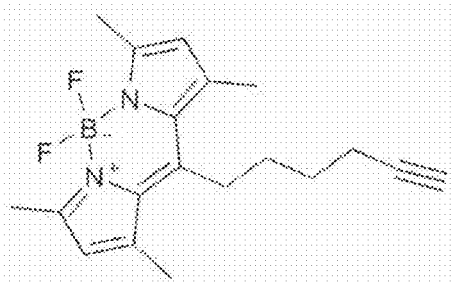
Compound 15
4,4-Difluoro-8-(hept-6-yne)-1,3,5,7-tetramethyl-4-bora-3a,4a-diaza-s-indacene
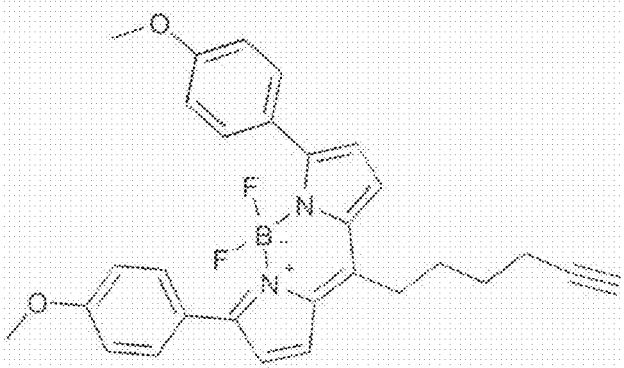
Compound 16
5,5-Difluoro-10-(hex-5-yn-1-yl)-3,7-bis(4-methoxyphenyl)-5H-dipyrrolo[1,2-c:2',1'-f][1,3,2]diazaborinin-4-ium-5-uide

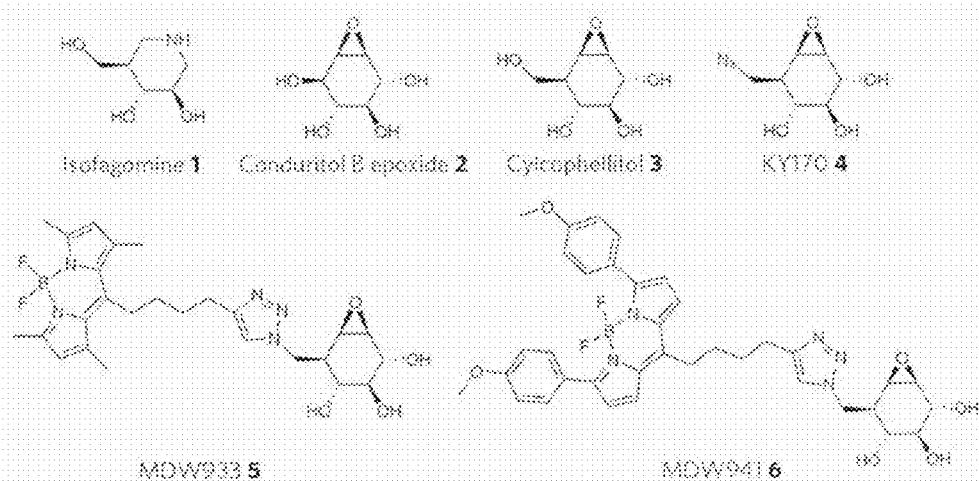

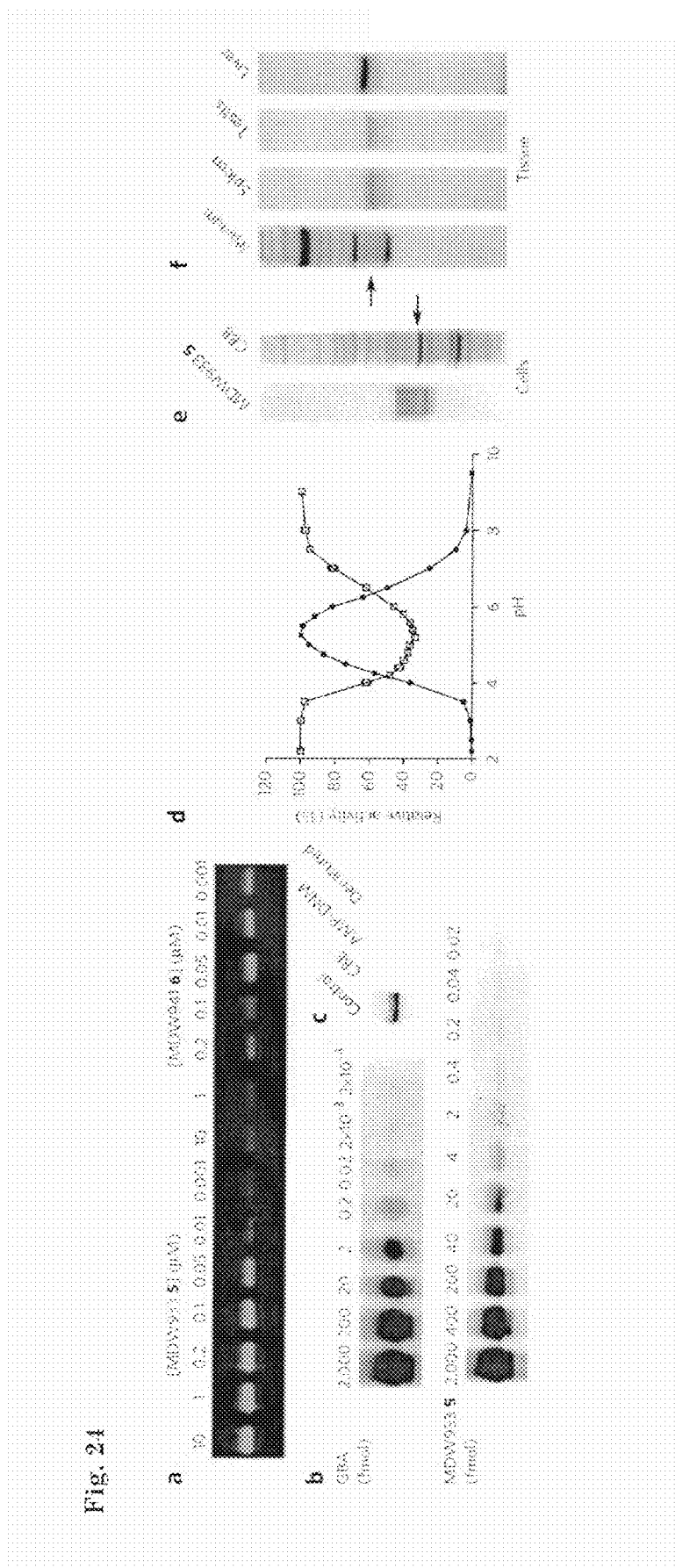
Fig. 2.1

Fig. 29
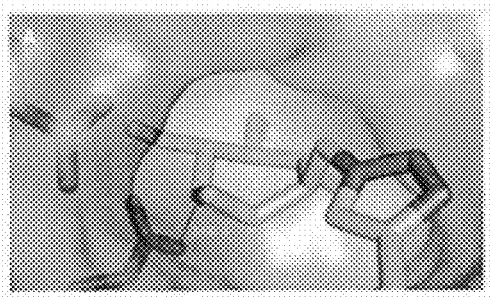
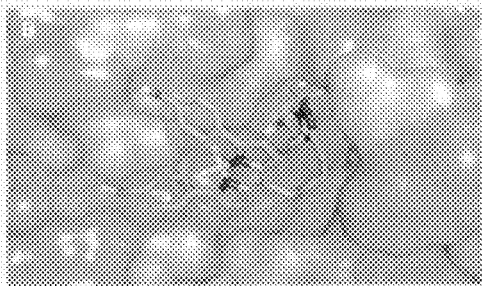
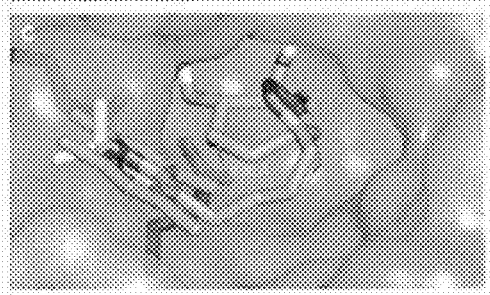
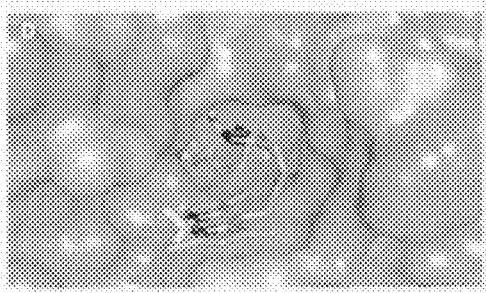
E
F
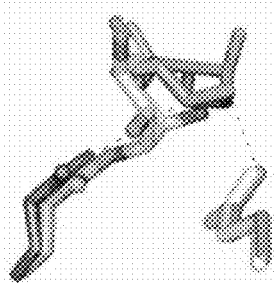
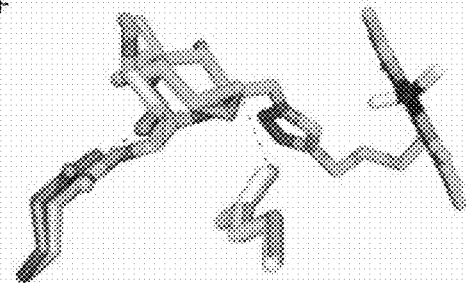
G
H
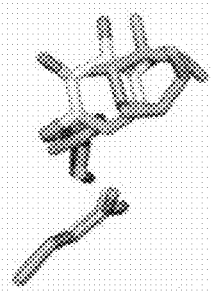
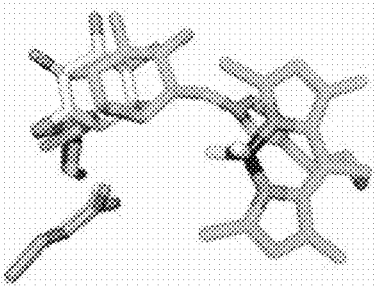

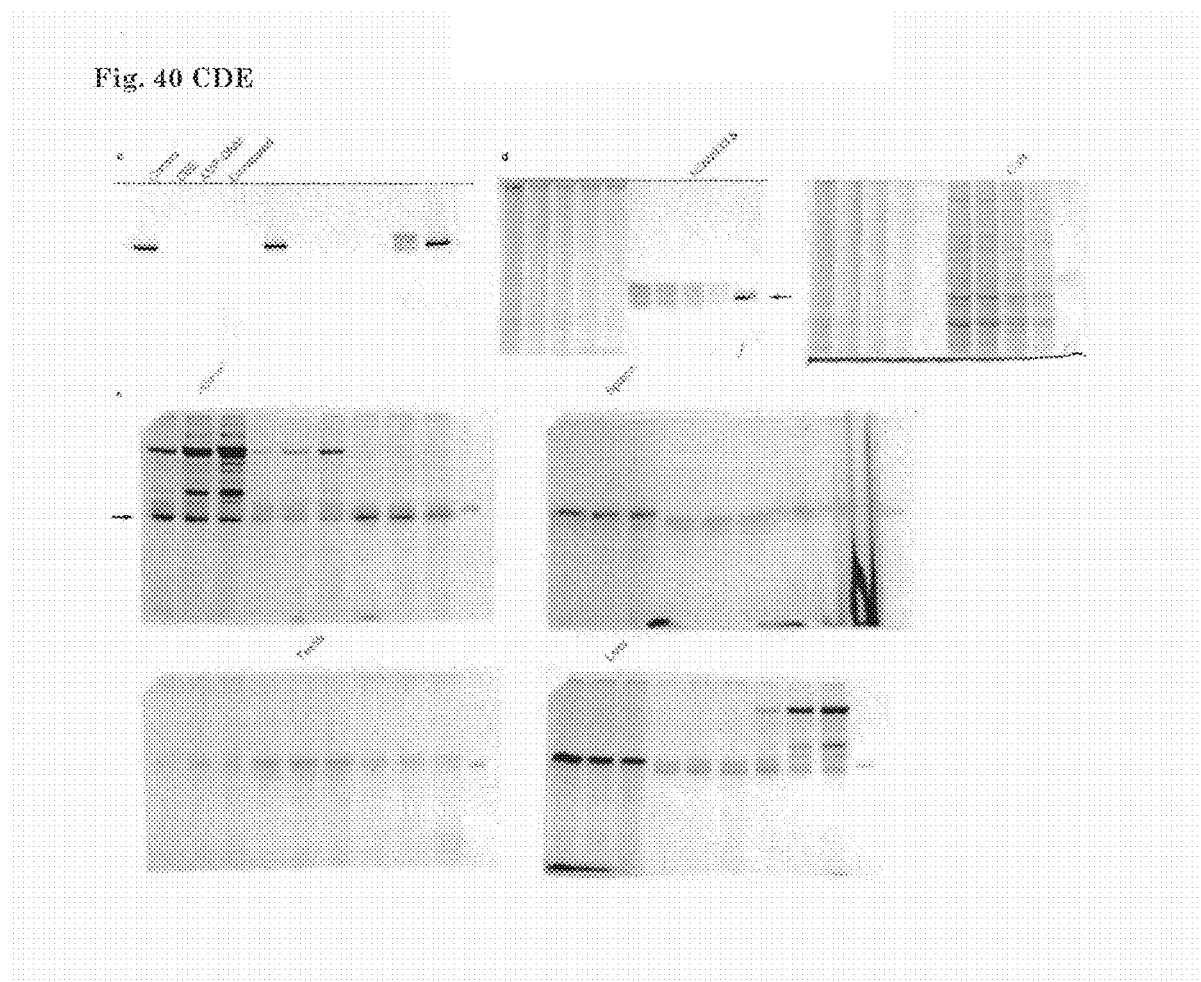

Fig. 46
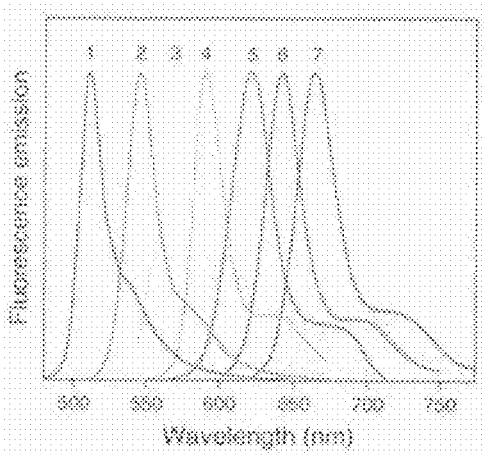
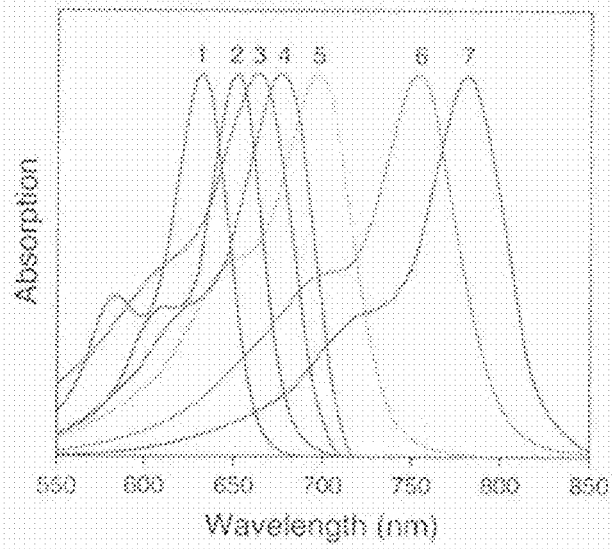
1 Alexa Fluor 633
2 Alexa Fluor 647
3 Alexa Fluor 660
4 Alexa Fluor 680
5 Alexa Fluor 700
6 Alexa Fluor 750
7 Alexa Fluor 790

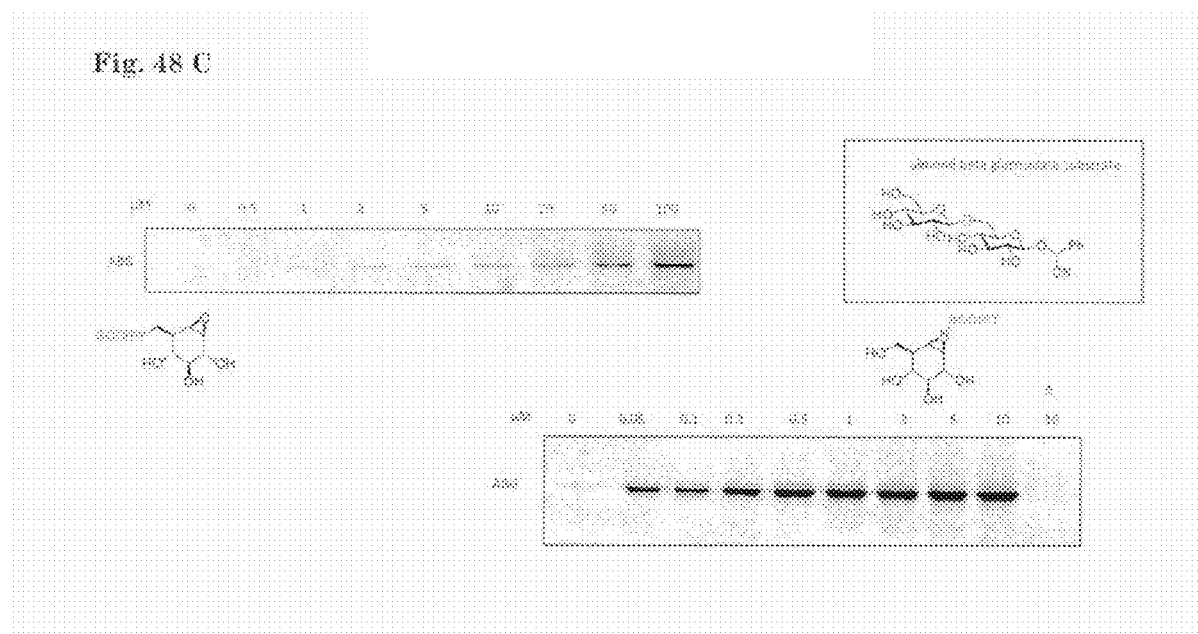

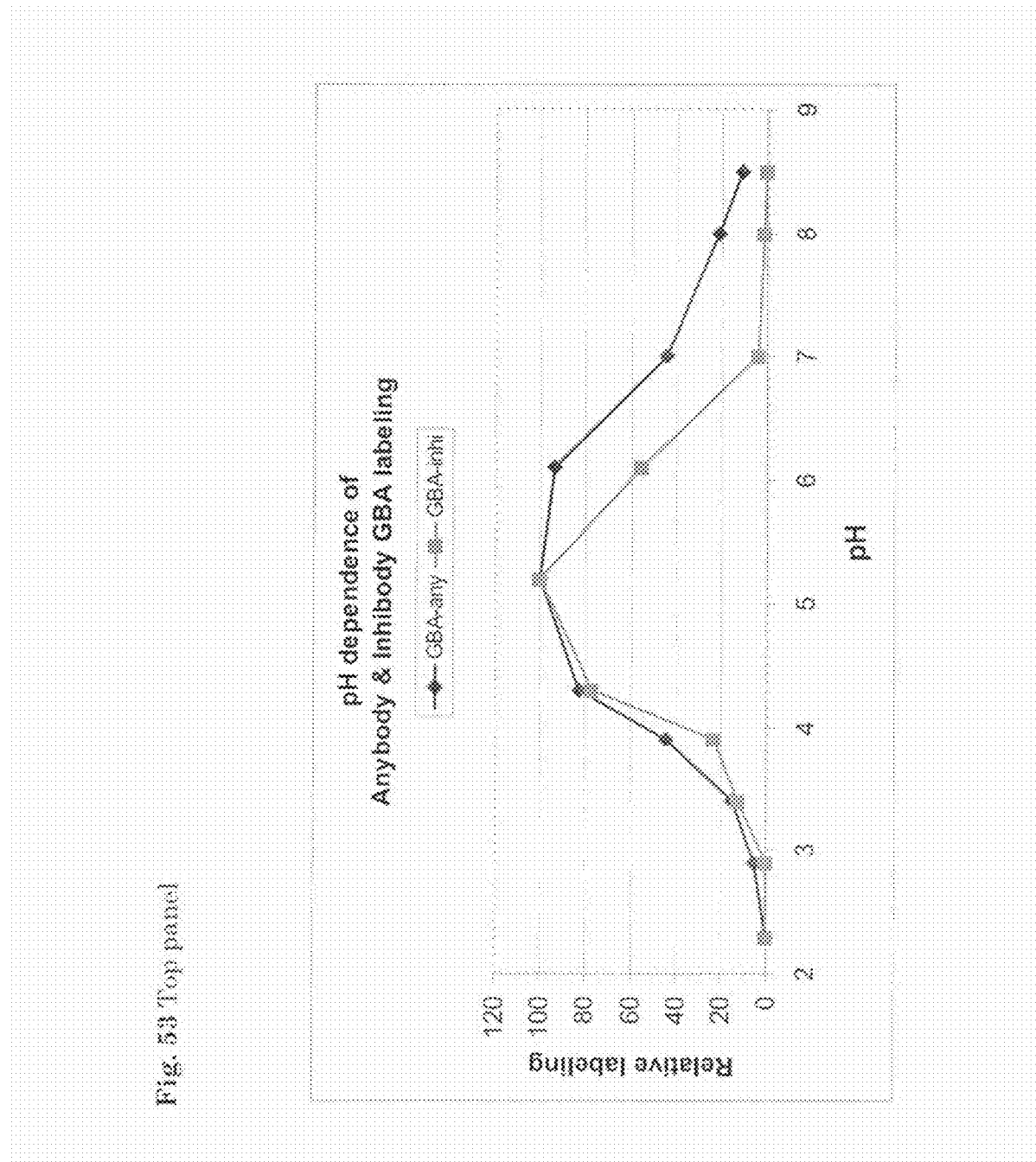
Fig. 53 Top panel

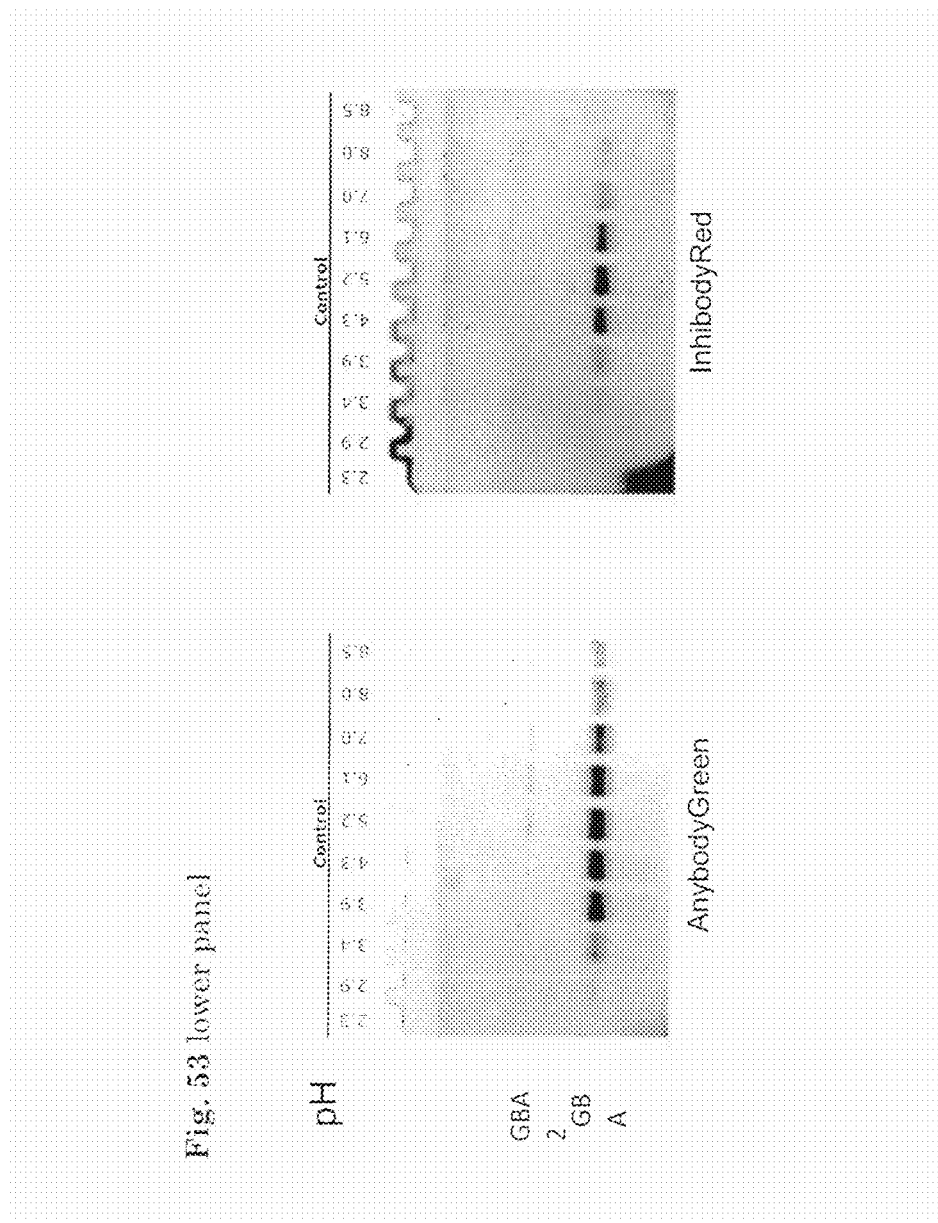
Fig. 53 lower panel

ACTIVITY BASED PROBES (ABPS) INTERACTING WITH GLYCOSIDASES

CROSS REFERENCE TO RELATED APPLICATIONS

This application is a §371 National Stage Application of PCT/NL2011/050164, filed Mar. 10, 2011, which claims priority to European Application No. 10156139.7, filed Mar. 10, 2010.

BACKGROUND OF THE INVENTION

1. Field of the Invention

The present invention refers to an activity based probe (ABP) comprising a glycosidase inhibitor, in particular a beta-glucosidase inhibitor, preferably covalently binding to a glycosidase comprising a detection-group.

2. Description of Related Art

Over the past decade, activity based protein profiling has been used to study many biological processes. The activity based probes (ABPs) used in these studies generally consist of three elements: a warhead, a linker/recognition element and ligation handle or identification tag. The enzyme reacts selectively with the warhead forming a covalent adduct which can then be visualized either by direct visualization (e.g the identification tag is present on the probe) or by two step labeling (e.g post-labeling modification of the ligation handle). This strategy has been widely applied to study proteases such as cathepsins, the proteasome, and esterases such as acetylcholinesterase.

With regard to glycosidases, in particular exo-glycosidases, only a few examples of ABPs are known. Vocadlo and Bertozzi describe a galactosidase probe, which is based on the activated fluorinated glycosides, a class of mechanism based inhibitors of glycosidases. The anomeric center of this galactosidase probe is activated by protonation by one of two carboxylic acids present in the active site of the glycosidase. The other carboxylic acid attacks the anomeric center forming a glycosyl-enzyme complex. The fluorine residue in the galactosidase probe slows formation as well as hydrolysis of the glycosyl-enzyme complex down. The activated leaving group increases the reaction rate of the first step leading to accumulation of the inhibitor complex. Although the complex is stabilized, the acylal ester linkage slowly hydrolyzes due to the endo-cyclic oxygen. Lifetimes ranging from seconds to months have been reported for these complexes. Despite this disadvantage, all ABPs reported so far are based on this class of mechanism-based inhibitors.

Numerous lysosomal storage disorders are based on malfunctions of one or more enzymes, for example glucosidases, involved in the metabolism of different substances. A storage disorder is any disease or condition which is characterised by the abnormal accumulation and storage of material within the cells. The stored material will vary depending upon the type of condition. One of the most common lysosomal storage disorders is Gaucher disease, which is characterized by a defective catabolism of glucosylceramide based on the malfunctioning of the enzyme glucocerebrosidase (GBA1). GBA1 is an acid hydrolase that primarily degrades its substrate in acidic compartments such as endosomes and lysosomes, particularly of macrophages. Increasing GBA1 activity is the rational target for therapy of Gaucher disease. This can be accomplished by enzyme therapy, by which mannose-terminated GBA1 upon intravenous infusion reaches lysosomes of macrophages Clinical response to enzyme therapy is spectacular, but their remain disadvantages. Firstly, the costs are extremely high (>100.000€/adult patient/year) and secondly, enzyme therapy does not prevent neurological manifestations given the inability of enzymes to effectively cross the blood-brain barrier.

Hence, since many years intensive research is ongoing to identify a therapeutic for effective treatment of storage disorders such as Gaucher disease. So-called substrate reduction therapy, using iminosugars or ceramide-mimics, aims to reduce biosynthesis of glucosylceramide in Gaucher patients, thus restoring the balance with impaired degradation. The common drugs for treating Gaucher disease these days (for example Zavesca, GENZ) show severe side-effects leading to gastrointestinal complications, such as flatulence and severe diarrhea resulting in abrupt weight loss, and poorly penetrate the brain. An interesting new approach for treating storage disease is the use of chaperones. The concept of chaperones implies that particular (point) mutant forms of an enzyme such as GBA1 can be assisted in their folding and stability by chaperones interacting with the catalytic pocket of the enzyme. For example isofagomine and hydrophobic iminosugars are considered as promising chaperones. When cells containing mutant GBA1 are incubated for some days with such chaperones (at concentrations close to $IC_{50}$ values), indeed an increased GBA1 activity is measured in cell lysates and increased GBA1 protein is detected by immunofluorescence. Unfortunately, it has not yet been documented that endo/lysosomal degradation of the glucosidase's substrate such as glucosylceramide improves, i.e., increases by chaperone treatment.

The lack of experimental evidence results from the fact that measurement of an increase in active enzyme in situ is difficult. No reliable methods for its measuring exists. Presently, some groups test the effect of chaperone treatment by incubating cells for 1 hour in acetate buffer (pH 4.0) containing the artificial substrate 4-methylumbelliferyl-beta-D-glucoside. It is far from being clear that under this condition the cellular surrounding of GBA1 is not fundamentally changed. Other research groups have measured GBA1 activity in living cells using fluoresceine-diglucoside (FDG) or fluorescent NBD-glucosylceramide as substrates. FDG is cleaved by GBA1 to generate fluorescent fluoresceine that can be detected for example by FACS. Fluorescent C6-NBD-GlcCer is added to cells, where after it is intracellularly converted to C6-NBD-Cer by GBA1. After harvesting the cells and extraction of lipids, the fluorescent NBD-glucosylceramide and NBD-ceramide can be separated, for example by thin layer chromatography, and be quantified. These advanced assays require considerable expertise, are labour-intensive and cumbersome.

Hence, it is presently problematic to assess the value of small compounds as effective chaperones for stabilization of a defect glucosidase such as GBA1 and thus, their therapeutic value for the treatment of lysosomal storage disorders such as Gaucher disease. Researchers presently still rely on artificial assays that poorly reflect a chaperone-mediated increase in in vivo degradative capacity, see for example Mu T W, Ong D S, Wang Y J, Balch W E, Yates J R 3rd, Segatori L, Kelly J W, Chemical and biological approaches synergize to ameliorate protein-folding diseases. Cell 2008 Sep. 5; 134(5):769-81.

The present invention now provides the development of highly efficient ABPs interacting with a glycosidase, providing basis for diagnosing a storage disorder and/or screening of compounds for preventing and/or treating a storage disorder such as Gaucher disease.

The present invention is further directed to efficient ABPs interacting with a glycosidase, providing basis for in vitro or in vivo monitoring of glycosidases in living organisms and cells.

Moreover, the present invention refers to efficient ABPs interacting with a therapeutic glycosidase, providing basis for in vitro or in vivo monitoring of a pre-labeled enzyme with respect to its delivery to lysosomes in cells and tissues of model animals and patients.

Further, the present invention relates to efficient ABPs interacting with a glycosidase-fusion protein, providing basis for ultra-sensitive in vitro or in vivo monitoring of the fusion protein.

SUMMARY

The present invention is directed to an activity based probe (ABP), which interacts with an enzyme, in particular a glycosidase, and preferably binds covalently to the active site of the enzyme. In one embodiment the ABP comprises a beta-glucosidase inhibitor, and a detection group. Optionally, the beta-glucosidase inhibitor is substituted for an alpha-glucosidase inhibitor, an alpha-galactosidase inhibitor, a beta-galactosidase inhibitor, an alpha-hexosaminidase inhibitor, a beta-hexosaminidase inhibitor, an alpha-mannosidase inhibitor, a beta-mannosidase inhibitor, an alpha-xylosidase inhibitor or a beta-xylosidase inhibitor. Optionally, the glycosidase inhibitor is not an iminosugar or an iminosugar derivative in particular not an iminoalditol derivative. In a preferred embodiment, the glycosidase inhibitor is a glucocerebrosidase inhibitor such as cyclophellitol or an analogue thereof. The ABP is used for diagnosing a storage disorder, preferably a lysosomal storage disorder such as Gaucher disease, Fabry disease, Pompe disease, or Tay-Sachs disease, Sandhoff disease and/or for screening of a compound to prevent and/or treat a storage disease. In a preferred embodiment the screened compound is a chaperone.

Moreover, the present invention refers to a method for producing and detecting an ABP and to kits for diagnosing a storage disorder and/or for screening of a compound to prevent and/or treat a storage disease comprising an ABP.

The ABP is used for ultra-sensitive labeling of therapeutic glycosidases used for treatment of lysosomal storage disorders, allowing in vitro or in vivo monitoring of cell/tissue targeting and stability of the therapeutic enzymes.

The ABP is used to label an appropriate glucosidase-fusion protein to monitor its expression, subcellular and/or tissue localization, and stability in vitro or in vivo.

DETAILED DESCRIPTION OF A PREFERRED EMBODIMENT

The ABPs of the present invention comprise enzyme inhibitors such as a glycosidase inhibitor, in particular a glucocerebrosidase inhibitors. In one embodiment inhibitors of the invention comprise cyclophellitol as a core structure or sterio-isomers thereof. The oxigen atom in the epoxide group of cyclophellitol can be substituted for a nitrogen or a sulfur atom, thereby forming an aziridine group or an episulfide group. Cyclophellitol was originally isolated form *Phellinus* sp. The inhibitors comprise a detection group in physical linkage with the inhibitor. For the inhibitors based on cyclophellitol the detection group is attached to the carbon atom that corresponds to the C6 position in glucose. For the cyclophellitol inhibitors with an aziridine or episulfide group instead of the epoxide group, the detection group can be attached to said Nitrogen or Sulfur atom. A preferred inhibitor is fluorophore-cyclophellitol, which is able to interact with, in particular covalently bind to, the active site of an enzyme such as a glucosidase. The present invention also provides inhibitors comprising an analogue of cyclophellitol. The term "analogue" comprises any compound that differs from the chemical structure of cyclophellitol, but shows the same effect on enzymes, in particular on glucosidases such as a glucocerebrosidase.

A glycosidase, comprising α- and β-glycosidases is any enzyme that belongs to the class of hydrolases and cleaves the glycosidic bond between two molecules. Examples of glycosidases are beta-glucosidases (e.g. glucocerebrosidase), alfa-glucosidase, beta-xylosidases, alfa-hexosaminidases, beta-hexosaminidases, alfa-galactosidases, beta-galactosidases, alfa-mannosidases and beta-mannosidases.

Conduritol B-epoxide (CBE), an irreversible inhibitor of GBA1 is known since a certain time. CBE has a xylose-type configuration and clicks covalently in the catalytic pocket of GBA1 after a nucleophile attack shown in FIG. 1, $1^{st}$ reaction. An advantage of CBE is that cells, are permeable for CBE, and the longer cells are incubated with CBE in situ, the more enzyme is irreversibly inactivated via CBE. It can be seen that cells from Gaucher patients with mutant N370S GBA1 are less sensitive for inactivation of their GBA1 compared to cells from healthy donors (FIG. 13).

Figure 3:
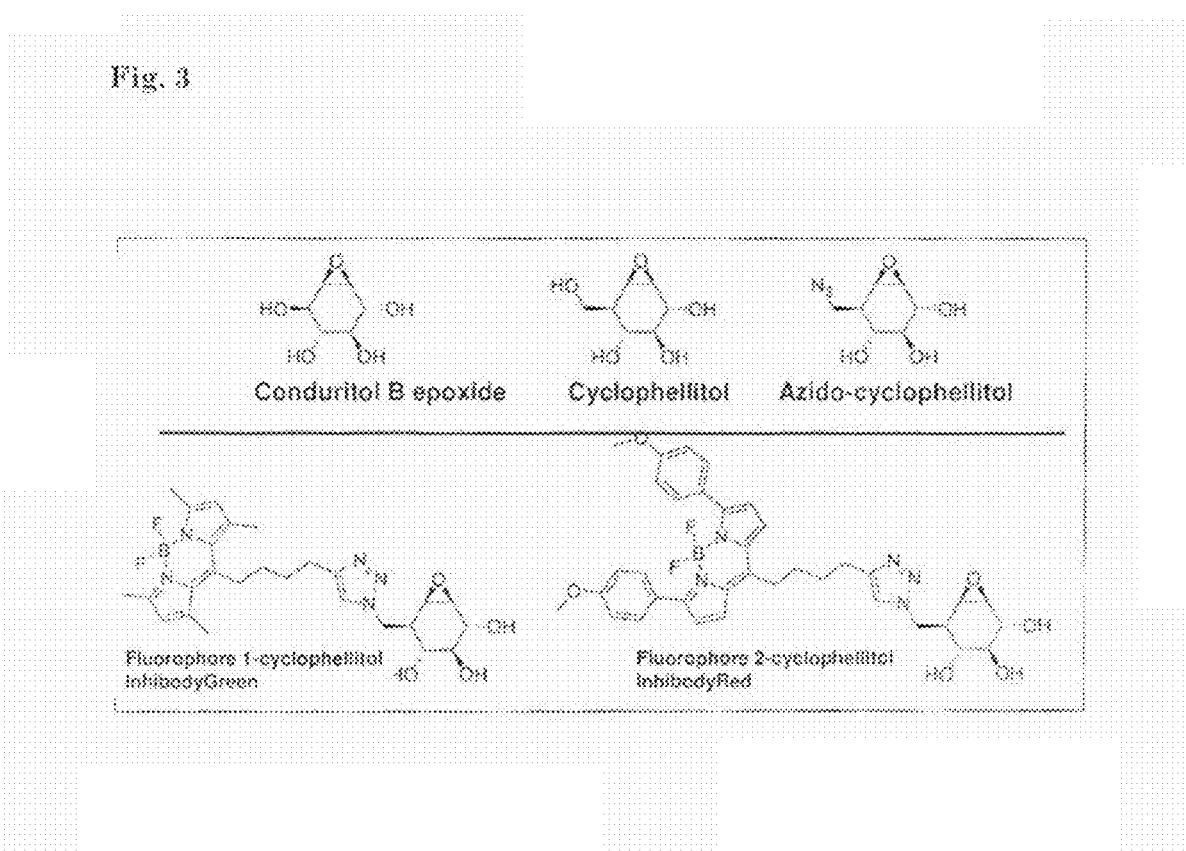
Figure 4:
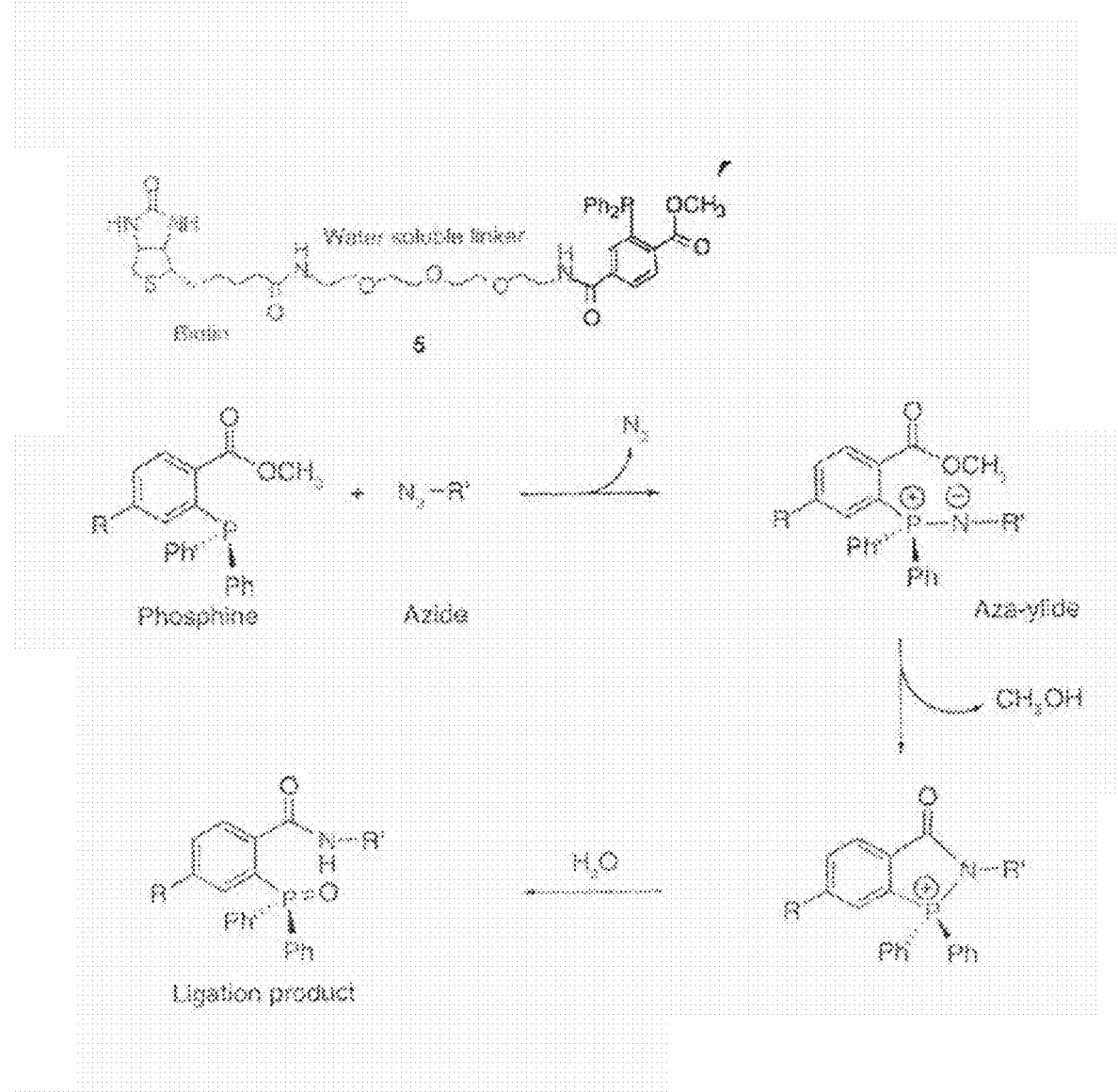

In contrast to CBE, cyclophellitol, a natural compound for example produced by yeast, has a glucose-type configuration as can be seen in FIG. 3. Cyclophellitol is intrinsically a superior inhibitor of beta-glucosidases such as GBA1 or lactase-phloridzin hydrolase. In a preferred embodiment, the glycosidase inhibitor such as cyclophellitol is modified for example by introducing an azid at position 1, 2, 3, 4, 5, or 6 of the glycosidase inhibitor, preferably at position 6 of the glycosidase inhibitor such as azido-cyclophellitol (FIG. 4). Azido-cyclophellitol is an excellent inhibitor of a glucosidase for example GBA1 (Tables 1 and 2) or lactase-phloridzin hydrolase or sucrase, and advantageously, the azide-group is detectable, for example on SDS-PAGE. However, coupling the detection group to the inhibitor prior to incubating the inhibitor with the target enzyme surprisingly led to a markedly improved affinity/sensitivity of detection/inhibition. In a very preferred embodiment, the modification group such as azid is coupled to the glycosidase inhibitor during the synthesis of the inhibitor. This group can subsequently be used to click on the detection group.

In one embodiment, the modified group of the glucosidase inhibitor, for example the azid group of azido-cyclophellitol, is linked to a detection group such as a fluorophore, a fluorescent moiety, or biotin. The glycosidase inhibitor and the detection group such as a fluorophore or biotin is for example linked via Staudinger reaction (FIG. 3), or any other state-of-the art ligation reactions. The combination of for example an azid group and a fluorophore or a biotin, or of for example an azid group with more than one detection group, e.g., a combination of a fluorophore and biotin leads in a preferred embodiment to an increase of the detection signal.

The detection group is connected to the glycosidase inhibitor before the inhibitor binds to the target glycosidase (which is for example a glucocerebrosidase or a lactase-phloridzin hydrolase or a sucrase). The inventors noticed that the affinity of the inhibitor unexpectedly increases, even if the detection group leads to a significant extension of the inhibitor (see for example Tables 1 and 2 for fluorophore 1-cyclophellitol, fluorophore 2-cyclophellitol). Table 1 shows a comparison of CBE and cyclophellitol analogues such as azido-cyclophellitol, fluorophore 1-cyclophellitol, wherein the $IC_{50}$ of the compound decreases with increase of the size of the compound. Fluorophore-cyclophellitols are highly potent inhibitors of GBA1, being ~5000× more potent than CBE. Table 2 shows the kinetic constants CBE, azidocyclophellitol, fluorophor 1-cyclophellitol, and fluorophor 2-cyclohelltiol. It should be noted that the affinity for binding (Ki) has been enormously improved by the presence of the hydrophobic fluorophore.

cosidase is the fact that the inventive ABPs like fluorophore-cyclophellitol detect only active glucosidase such as a glucocerebrosidase, e.g., GBA1 or a lactase-phloridzin hydrolase, whereas an antibody detects active and inactive enzyme. Thus, the present invention allows the differentiation of active and inactive enzyme, in particular of glucosidase such as glucocerebrosidase.

Figure 7:
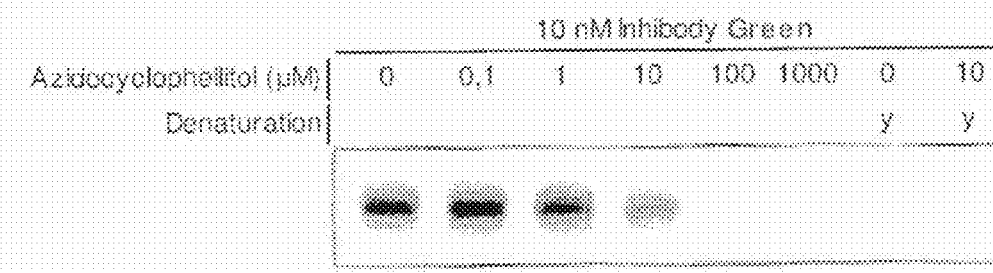

In addition, the specificity of the fluorophore-cyclophellitol is excellent, which is shown by the competition of GBA1 labelling by AMP-DNM, a competitive inhibitor showing Ki=~200 nM (FIG. 7). The dependency of the labelling on active glucosidase is demonstrated by the effect of heat dena-

TABLE 1

Structure formulas are shown in FIG. 3.

| Structure | Compound | Apparent $IC_{50}$ (nM) rec. GBA1: 30 min, 37 C., pH 5.2 + Tch, Tr |
|---|---|---|
| (structure image) | Conduritol B-epoxide | 12,000 ± 250 |
| (structure image) | Azido-cyclophellitol | 150 ± 30 |
| (structure image) | Fluorophore 1-cyclophellitol | 2 ± 0.5 |

TABLE 2

|  | $k_i$ (µM min$^{-1}$) | $K_i$ (µM) |
|---|---|---|
| CBE | 0.0244 | 7.726 |
| Azido-cycl. | 0.0237 | 0.083 |
| F1-cycl. | 0.0236 | 0.00095 |
| F2-cycl. | 0.0236 | 0.00156 |

Figure 8:
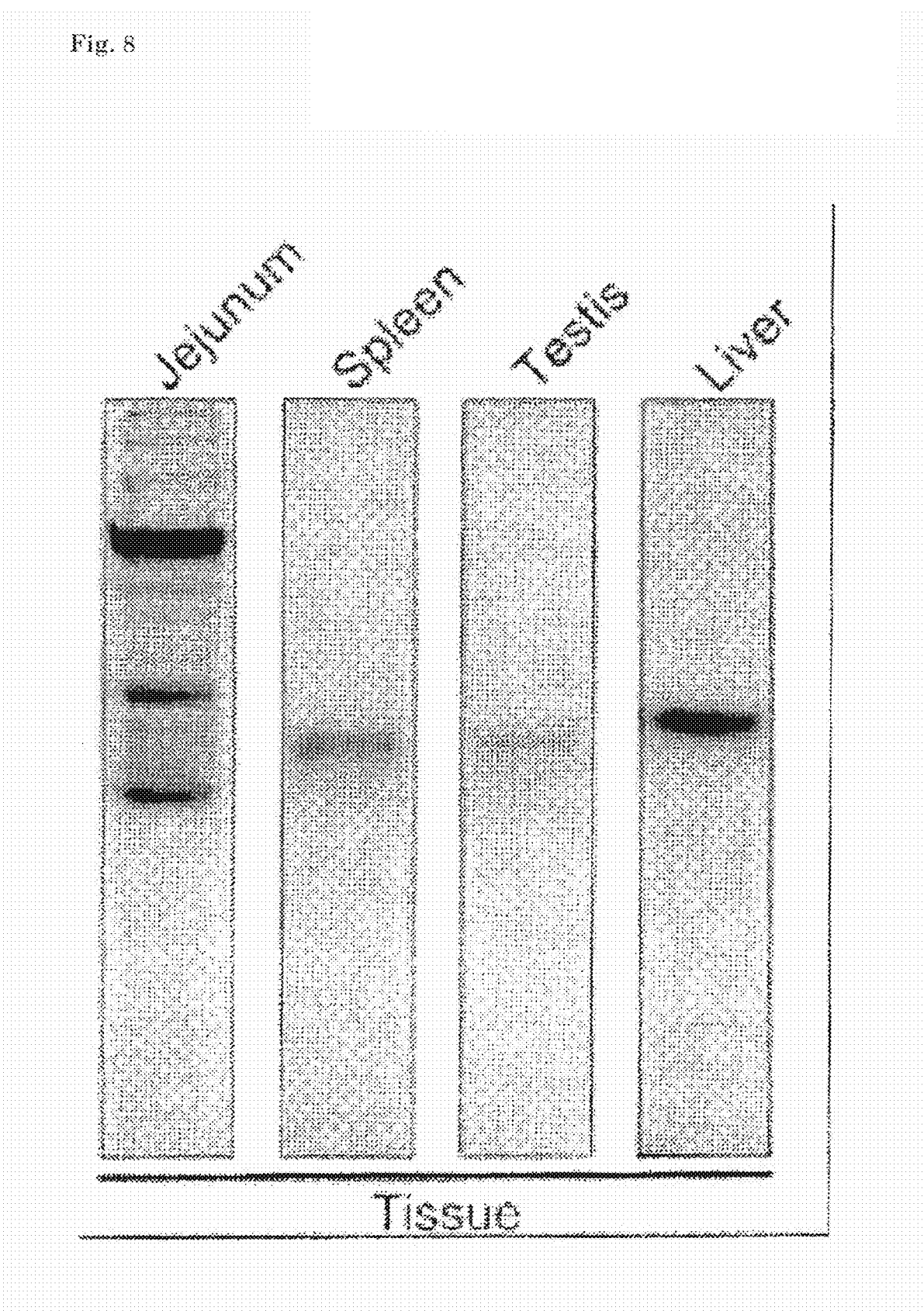

Moreover, the detection of a glycosidase such as a glucocerebrosidase, e.g., GBA1 or a lactase-phloridzin hydrolase or a sucrase having an ABP of the present invention such as fluorophore 1-cyclophellitol or fluorophore 2-cyclophellitol is highly sensitive (FIG. 6). Using an ABP of the invention such as fluorophore 1-cyclophellitol, an amount of GBA1 of 10 attomole was detected on slab gel. To illustrate this enormous and unexpected sensitivity of ABPs of the invention, a comparison with the detection of GBA1 using an antibody in a western blot is useful (see also FIG. 13). A supreme anti-GBA1 monoclonal antibody in an excess concentration allows only detection of GBA1 in the range of 100 femtomoles. A further advantage of the ABPs of the invention such as fluorophore-cyclophellitol used for the detection of a gluturation of the glucosidase, which prevents the labeling (FIG. 7). Even when total tissue lysates are labeled with fluorophore-cyclophellitols remarkable specific labeling of GBA1 occurs (FIG. 8).

In another preferred embodiment, the ABPs of the invention such as fluorophore-cyclophellitol are likewise efficient, i.e., specific and sensitive, on living cells (FIG. 9) for example on isolated cell or tissue samples. The ABPs of the invention were detectable in cultured fibroblasts, COS and HepG2 cells, respectively, allowing detection of the glucosidase such as a glucocerebrosidase, e.g., GBA1 in the attomole range after incubation of cells for 1 hour with a low amount for example 100 nM of fluorophore-cyclophellitol.

Figure 10:
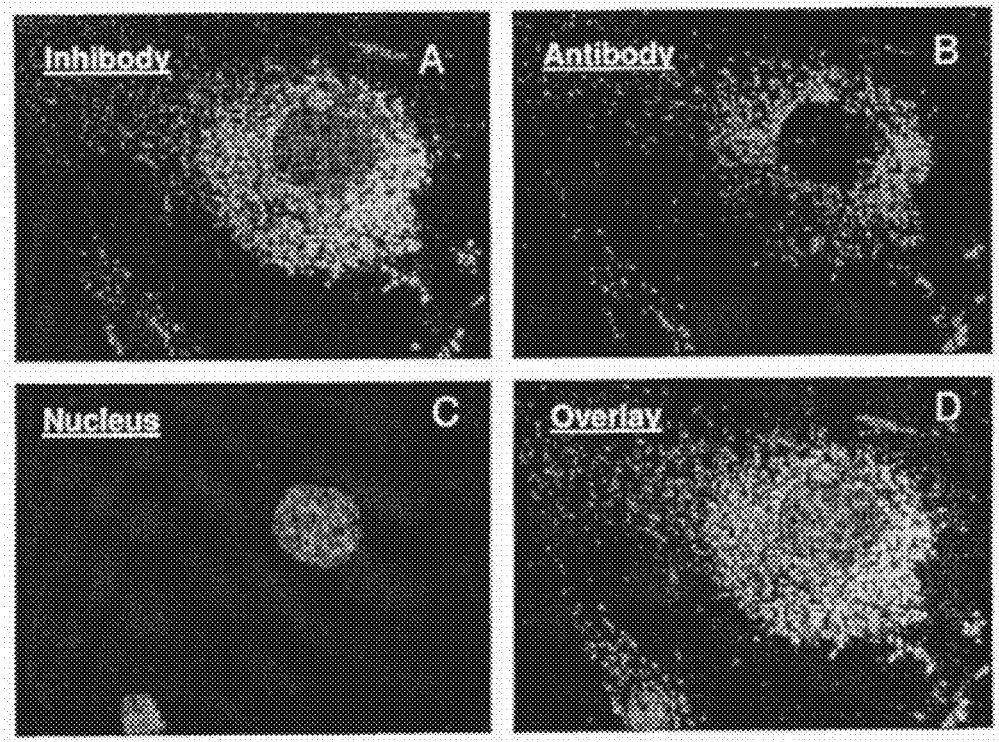

Moreover, the ABPs of the invention such as fluorophore-cyclophellitols can be used to label glycosidases and visualize them by fluorescence microscopy (FIG. 10), or FACS (FIG. 11) as illustrated for glucocerebrosidase. Using two distinctly fluorescent fluorophore-cyclophellitols, e.g. fluorophore 1-cyclophellitol being green fluorescent and fluorophore 2-cyclophellitol being red fluorescent, pulse-chase experiments can be conducted in living, cells, tissue, preferably isolated, or organisms, allowing assessment of life cycle and stability of glucocerebrosidase (FIG. 12) in vivo or in vitro.

Moreover, the ABPs of the invention such as fluorophore-cyclophellitols can be used for detection, in particular diagnostic purposes. Patients deficient in active glycosidases can be identified by incubation of cells with appropriate cyclophellitols. This is illustrated in FIG. 13 showing the visualization of glucocerebrosidase upon incubation of cells with fluorophore 1-cyclophellitol. The approach is more sensitive and convenient compared to Western blotting.

In another preferred embodiment, the ABPs of the invention such as fluorophore 1-cyclophellitol or fluorophore 2-cyclophellitol are likewise efficient, i.e., specific and sensitive, on living mice (FIG. 14). The ABPs of the present invention will allow, for example by intravenous or intrathecal administration to animals, the ultra-sensitive detection of active GBA in situ. The results allow to generate new insights for example in pathophysiology of storage disorders such as Gaucher disease and render insights for therapy improvement.

Figure 15:
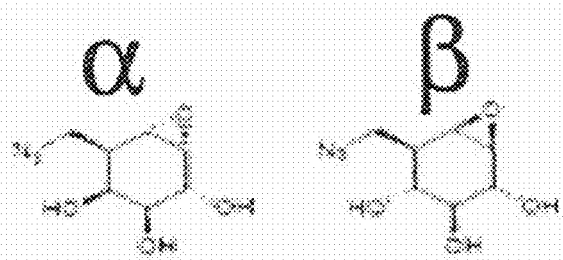

The approach of ABPs can be extended to other glycosidases such as lactase, amylase, chitinase, sucrase, maltase, neuraminidase, invertase, hyaluronidase, lysozyme etc. by variation of the glycosidase inhibitor to selectively label specific alfa- or beta-glycosidase (see FIG. 15 for an example). This variation is in particular in the sterio-isomeric carbons. The glycosidases are generally very specific for a certain sterio-isomeric sugar that is bound in the catalytic site. For instance, the fluorophore 1-cyclophellitol or fluorophore 2-cyclophellitol compounds depicted in FIG. 3, are very specific for the beta-glycosidase cerebrosidase. These inhibitors efficiently detect and inhibit only one other beta-glycosidase, i.e. lactase (lactase-phloridzin hydrolase). Moreover, the fluorophore can be varied allowing selective detection of labeled enzyme in a specific environment, e.g., a pH dependent fluorophore (see FIG. 16), which for example provides a signal at a specific pH, changes the colour at a specific pH, or changes the intensity of the fluorescence at a specific pH. Moreover to the fluorophore can be attached an additional functional moiety, for example biotin allowing purification of ABP-labeled protein by streptavidin pull downs (see FIGS. 16 and 17). The fluorophore is preferably a bodipy fluorophore, preferably a bopidy fluorophore according to FIG. 45. Bodipy (short for boron-dipyrromethene), is a class of fluorescent dyes that are very versatile. They are exhibit efficient fluorescent and are thus very bright, form a chemical group of compounds that are relatively similar to each other, while at the same time providing clearly distinguishable staining, or fluorescence patterns (see FIGS. 45 and 46). In another preferred embodiment said fluorophore is a far red or preferably infrared, and more preferably near infrared fluorophore. Examples of such fluorophores are the Alexa series sold by invitrogen. Their emission spectrum is provided in FIG. 46. The detection group can also comprise radiolabel. In cases wherein R2 comprises a hydrophobic group, preferably one or more aromatic groups, The radiolabel can be present on X, R1 or R2, preferably said radiolabel is present on R2.

Given the subtle and ultra-sensitive labeling of glycosidases by the ABPs of the invention, this can be exploited to monitor pre-labeled therapeutic glycosidases in living cells, e.g., cell samples, and living organisms, including patients. The principle of this is illustrated for glucocerebrosidase and Gaucher disease in FIGS. 18 and 19.

In a further embodiment, ABPs of the invention are used to visualize fusion proteins comprising an ABP-reactive glycosidase, i.e., a glycosidase binding to the glycosidase inhibitor of the ABP. The ABP-reactive glycosidase preferably represents a marker and tag, respectively, allowing the detection of the fusion protein. The glycosidase-fusion protein is preferably based on genetic modification for example expressed by a genetically modified expression vector Given the ultra-sensitive detection of glycosidases with the ABPs of the invention, a similar use to (E)GFP-fusion proteins is envisioned. Glycosidases with desired properties have to be selected for construction of fusion proteins. For example, a fusion protein containing glucocerebrosidase is only useful when the fusion protein resides in the endoplasmic reticulum, Golgi apparatus, endosomes, lysosomes, the plasma membrane or is a secretory protein since otherwise glucocerebrosidase will not acquire the N-linked glycans required for its enzymatic activity.

Figure 16:
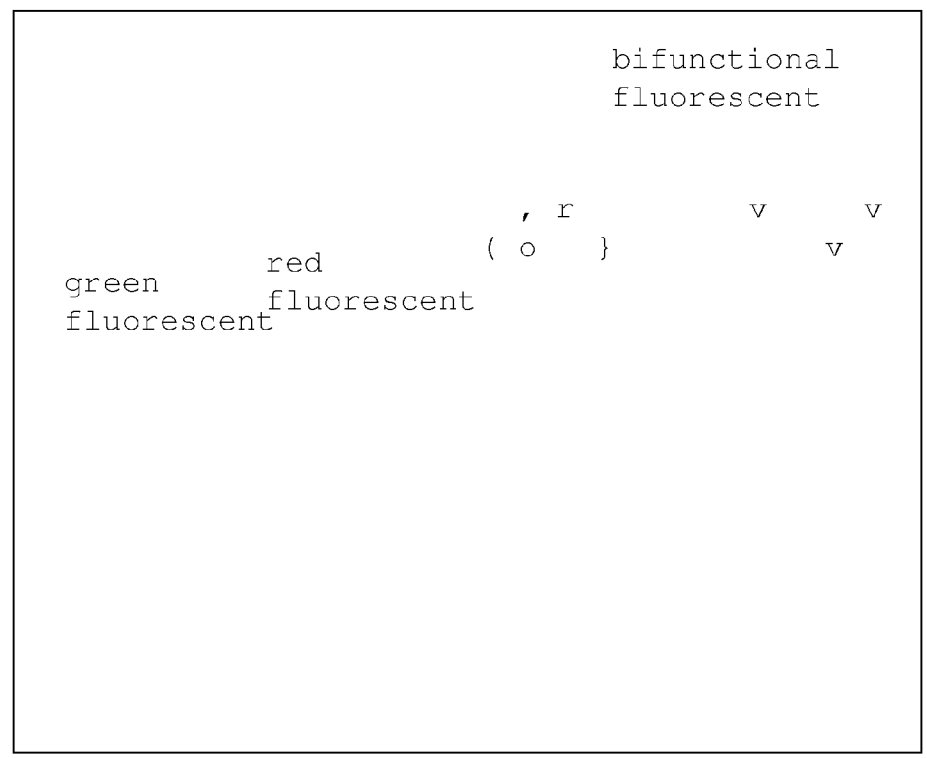

A major advantage of the present approach of an ABP and glycosidase fusion protein compared to the conventional EGFP fusion protein approach is the ability to fluorescently label the fusion protein at any desired moment and to select ABPs with special features such as fluorescence in the infra red (allowing more sensitive in vitro or in vivo molecular imaging) or dependent on the environment like pH or calcium concentration (FIG. 16). Moreover, pulse-chase experiments can be conducted employing different ABPs that allow in vitro or in vivo visualization of the life time of the fusion protein.

The ABPs are detectable by detecting the detection group that it comprises. The detection group for example a fluorophore or a biotine is connected to the glycosidase inhibitor, preferably the glucosidase inhibitor, before the binding to the enzyme and once the inhibitor is bound to the enzyme, the detection group is detected.

In one embodiment, the ABP comprises a cylophellitol, or a sterio-isomer thereof or analogue, which is selected from the group consisting of for example:

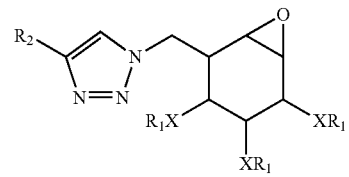

$R_1$=Hydrogen, Carbohydrate, Alkyl, Aromate, Amide, biotin, fluorophore
$R_2$=Alkyl, Aromate, Biotin, Fluorophore
X=O, N, S

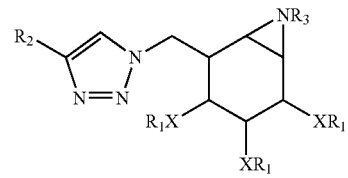

$R_1$=Hydrogen, Carbohydrate, Alkyl, Aromate, Amide, biotin, fluorophore
$R_2$=Alkyl, Aromate, Biotin, Fluorophore
$R_3$=Amide, Alkyl, or Fluorophore
X=O, N, S The azide/alkyne of the two-step probes can be clicked to a fluorophore, a biotin or both using Cu (I) catalyzed click-reaction. The "clicked" probes can be used to directly visualize glycosidase in vivo. Furthermore the azide of the two-step probes can be reduced with and subsequently condensed with an acid giving acetamide probes. The stereo-centers can have any configuration allowing labeling of the various glycosidases. R can be a carbohydrate, to label endo-glycosidases, alkyl and/or aromatic to enhance binding. X can be O, N, S; or

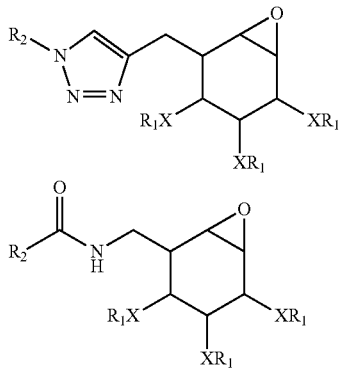

R₁=Hydrogen, Carbohydrate, Alkyl, Aromate, Amide, biotin, fluorophore
R₂=Alkyl, Aromate, Biotin, Fluorophore
X=O, N, S
an aziridine based probe:

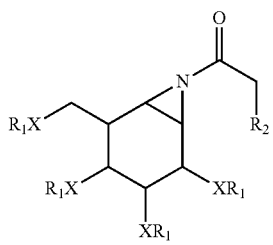

R₁=Hydrogen, Carbohydrate, Alkyl, Aromatic, Amide
R₂=alkyl, aromatic, Azide, alkyne, biotin, fluorophore
X=O, N, S

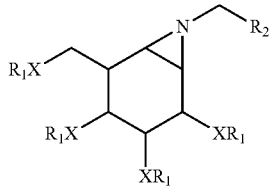

Figure 44:
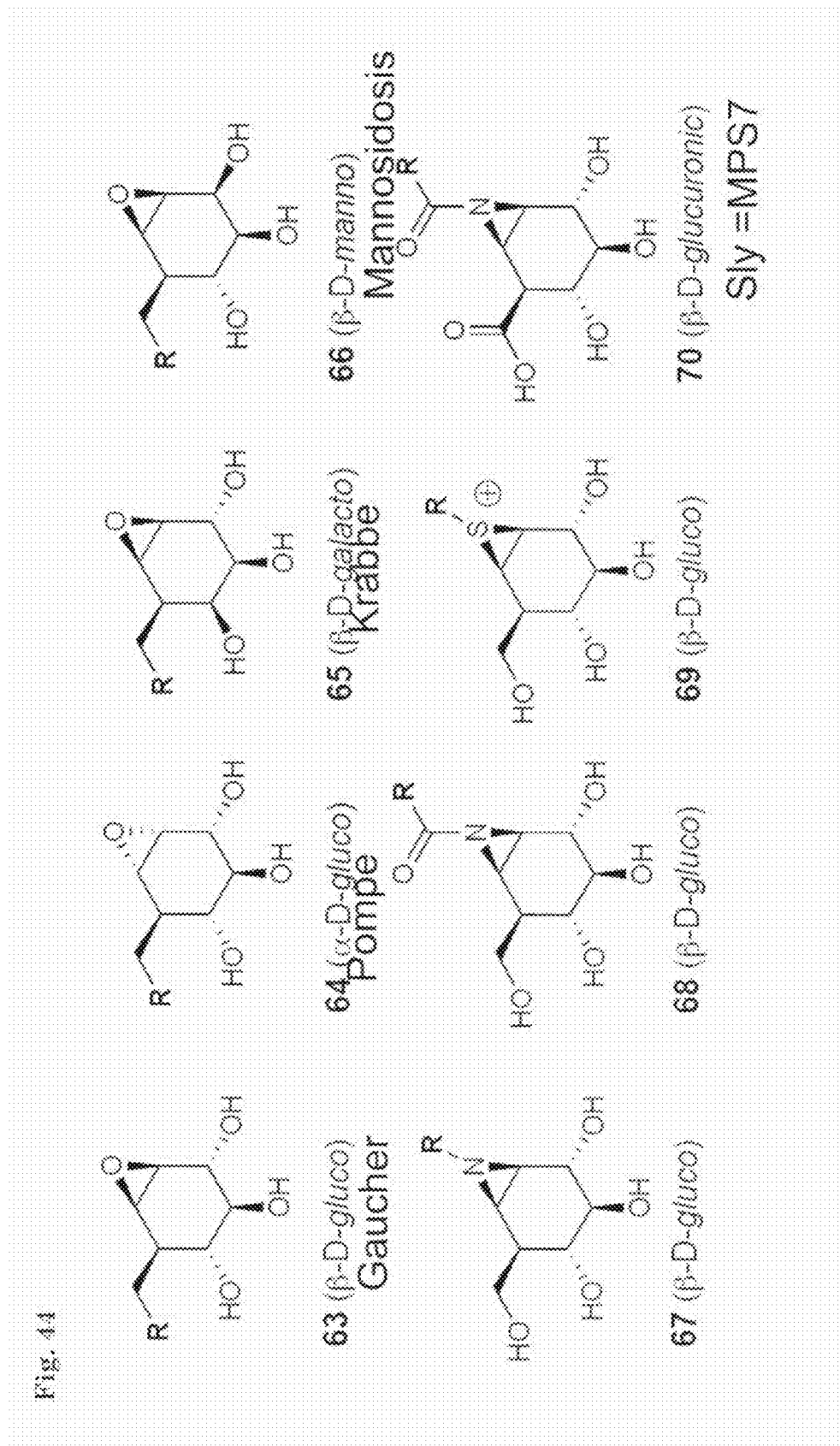

R₁=Hydrogen, Carbohydrate, Alkyl, Aromatic, Amide
R₂=alkyl, aromatic, azide, alkyne, biotin, fluorophore
X=O, N, S Aziridines can be functionalized with acetyl or alkyl equipped with an azide or alkyne (two-step labeling) or with biotin/fluorophore (direct labeling). The stereo-centers can have any configuration allowing labeling of the various glycosidases. R can be a carbohydrate, to label endo-glycosidases, alkyl and/or aromatic to enhance binding. X can be O, N, S;

As mentioned herein above, the cyclophellitol can have various sterio-isomeric configurations. Examples of such configurations are given in FIG. 44.

In a preferred embodiment the ABP is compound 5 or compound 6 of FIG. 23. In another preferred embodiment the ABP is compound 6 of FIG. 38.

Figure 47:
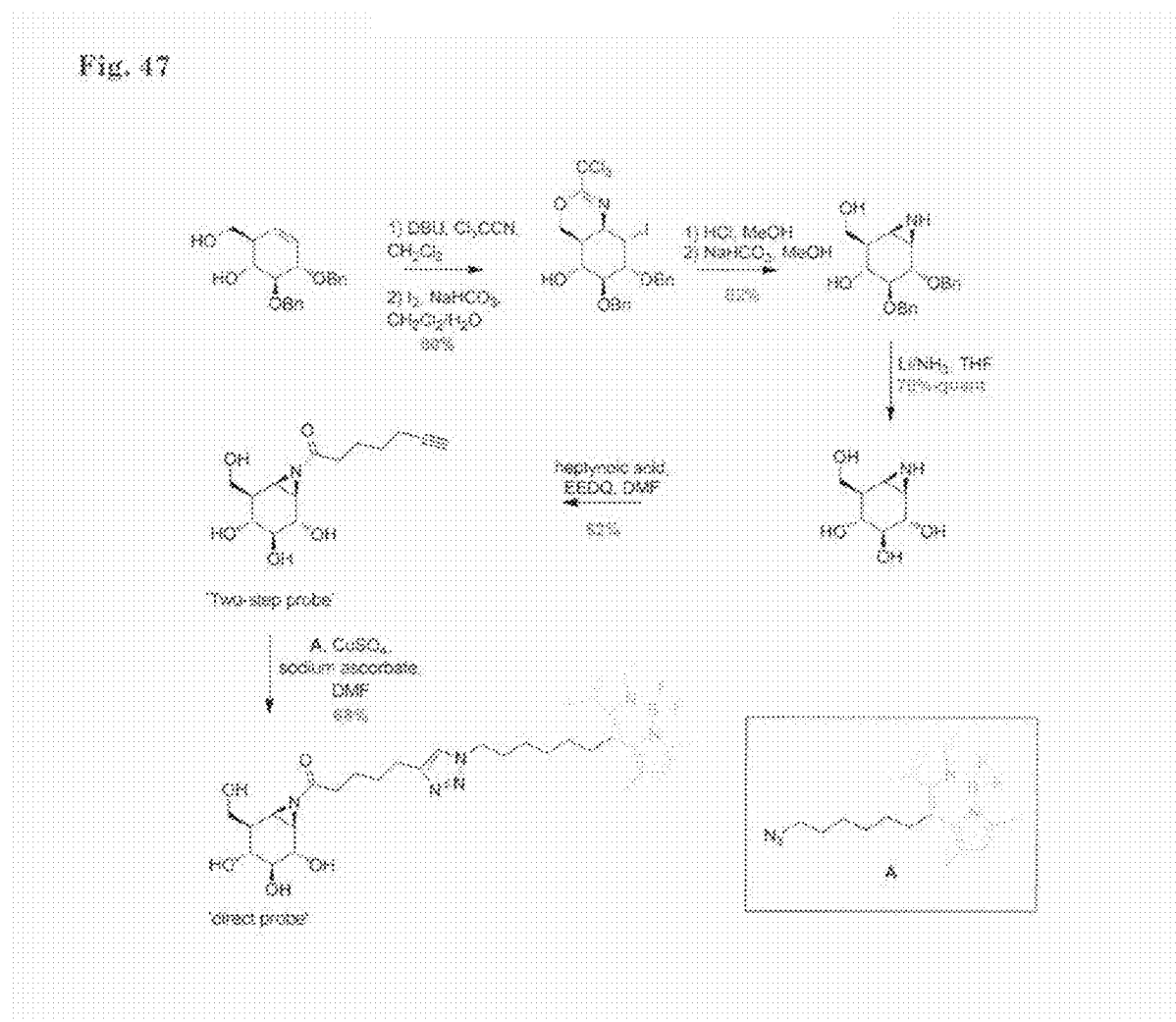

In a preferred embodiment the ABP is a compound marked "direct probe" of FIG. 47.

Figure 51:
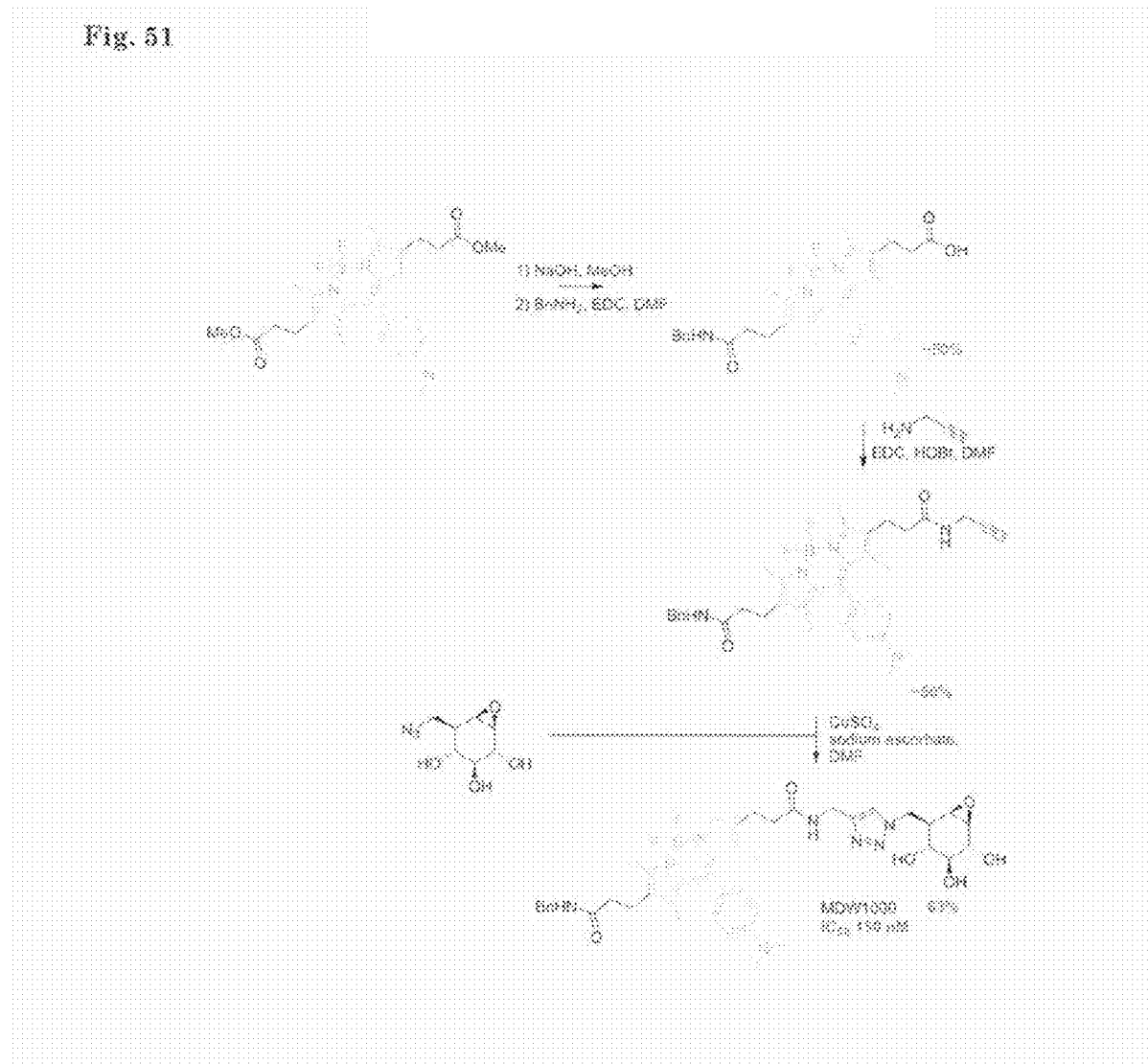

In a preferred embodiment the ABP is compound MDW1000 depicted in FIG. 51.

In a further embodiment, an ABP of the invention for example a fluorophore-cyclophellitol is used for diagnosing a storage disorder (see FIG. 13 for an example). Advantageously, one or more glycosidases are detectable using different glycosidase inhibitors, which are specific for each glycosidase. Alternatively, one glycosidase inhibitor inhibits one or more glycosidases, for example glucocerebrosidase and/or lactase-phloridzin hydrolase and/or sucrase. A storage disorder is tested for example on a body fluid, such as blood, serum, urine, liquor, or sputum, or any other isolated cells or tissue. Furthermore, ABPs of the present invention are able to monitor the targeting of enzyme therapeutics in patients suffering from a storage disorder for example a Gaucher patient, in particular due to the ability of these ABPs to penetrate various tissues, or the bone compartment (see FIG. 19).

In another embodiment, ABPs of the present inventions are used in screening of a compound for use in preventing and/or treating a storage disease, e.g., Gaucher disease. Such compound is preferably a chaperone, wherein a chaperone is any molecule, for example a protein, peptide, DNA, RNA, small molecule that assists a protein in achieving proper folding. The compound is screened either in vivo or in vitro. The detection of chaperones allows also monitoring the efficacy of chaperones in different environments, e.g., different parts of the human or animal body. FIG. 20 presents an example of screening with an ABP the efficacy of a tentative chaperone for mutant glucocerebrosidase in Gaucher disease patients.

In a further embodiment, ABPs are used to detect a catalytic site directed to inhibitors of glucocerebrosidase that act on living cells for example by screening such catalytic side in libraries. For the screening of living cells for example the cells are incubated with an ABP and lack of staining points to competition at the catalytic side. This screening assay is particularly useful as a first screening step.

In a further embodiment, ABPs are used in molecular imaging, i.e. to visualize fusion proteins containing an ABP-reactive glycosidase. Given the ultra-sensitive detection of glycosidases with the ABPs of the invention, a similar use to (E)GFP-fusion proteins is envisioned. The glycosidases with desired properties have to be selected for construction of glycosides fusion proteins. For example, a fusion protein containing glucocerebrosidase is only useful when the fusion protein resides in the endoplasmic reticulum, Golgi apparatus, endosomes, lysosomes, the plasma membrane or is a secretory protein since otherwise glucocerebrosidase will not acquire the N-linked glycans required for its enzymatic activity.

A major advantage of the innovative ABP and glycosidase fusion protein approach compared to the conventional (E)GFP fusion protein approach, is the ability to fluorescently label the fusion protein at any desired moment and to select ABPs with special features such as fluorescence detectable signal like fluorescence for example in the infra red or dependent on the environment like pH or calcium concentration (FIG. 16). Moreover, pulse-chase experiments can be conducted employing different ABPs that allow in vitro or in vivo visualization of the life time of the fusion protein.

Moreover, an embodiment refers to a method for producing an ABP wherein the glycosidase inhibitor is chemically modified and linked to a detection-group. The glycosidase inhibitor is preferably the irreversible glucosidase inhibitor cyclophellitol, which is modified with a fluorophore or biotine. Alternatively, the azido-cyclophellitol is linked to a fluorophore, fluorescent moiety, or biotine.

Figure 1:
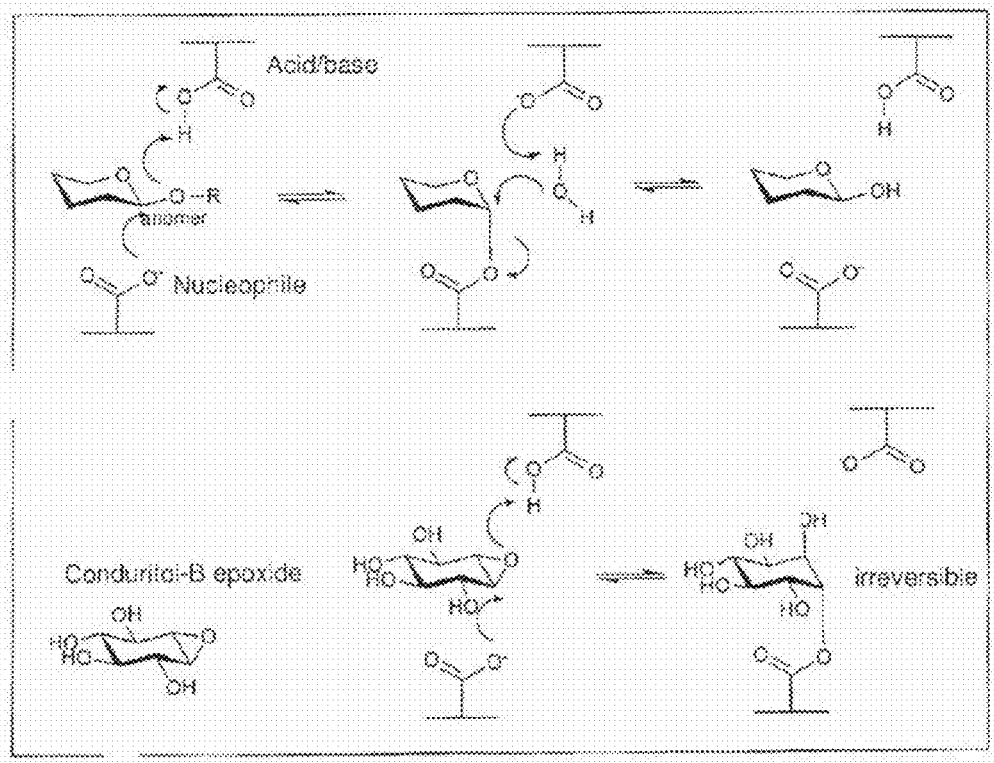
FIGS. 1-60 depict embodiments of the present invention as described herein.

The following figures illustrate, but do not limit the present invention:

FIG. 1 shows the reaction mechanism of glucocerebrosidase (GBA1) with natural substrate and conduritol B-epoxide (CBE), wherein CBE binds covalently to the nucleophile E340 in the catalytic pocket of GBA1.

Figure 2:
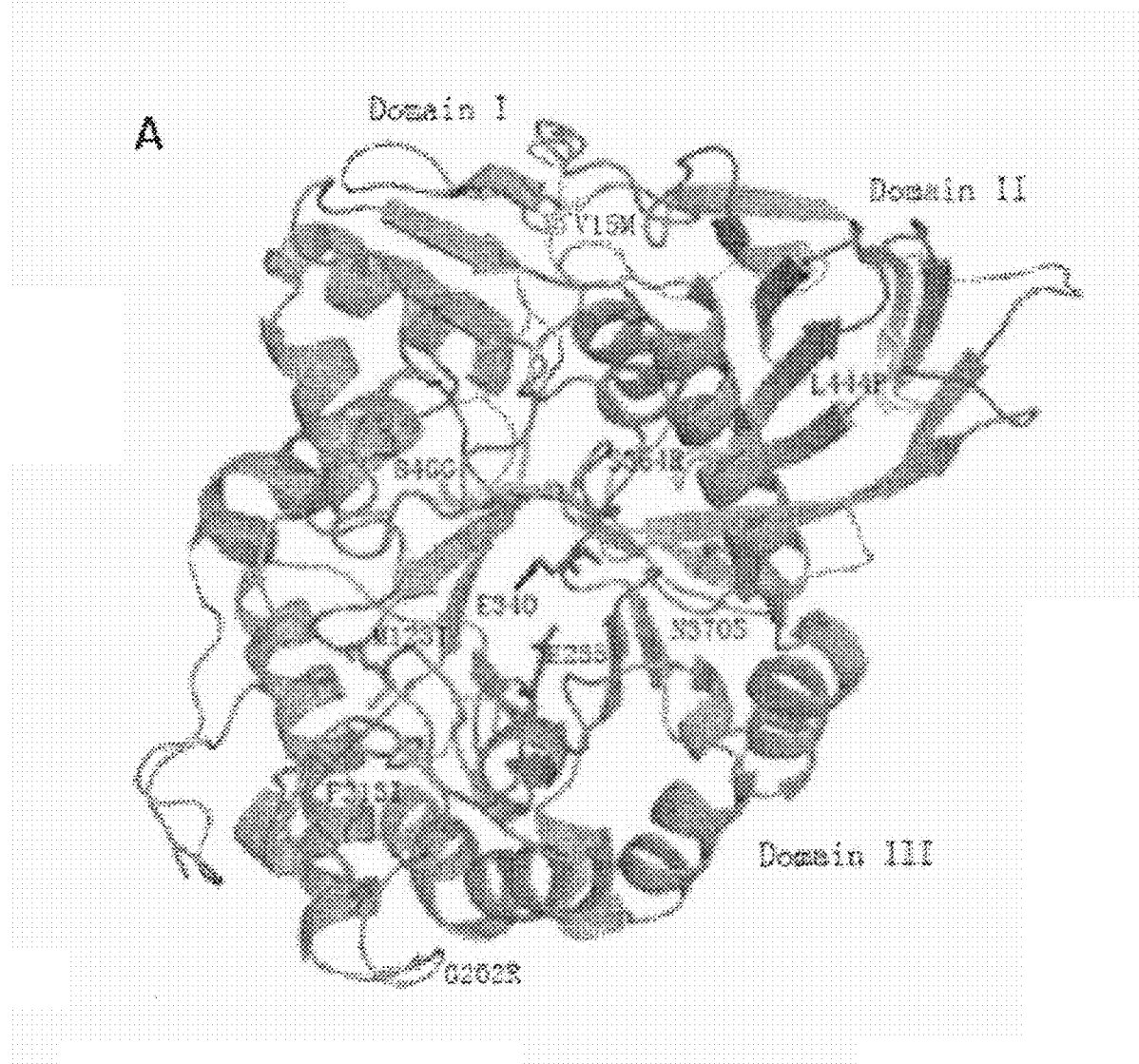

FIG. 2 shows the 3-dimensional structure of GBA1 based on crystallography, wherein E340 is catalytic nucleophil and E235 is acid/base.

FIG. 3 shows the chemical structures of CBE, cyclophellitol, and analogues of cyclophellitol. Fluorophore 1-cyclophellitol (Inhibody Green) is a green fluorescent, fluorophore 2-cyclophellitol (Inhibody Red) is red fluorescent.

FIG. 4 presents the Staudinger reaction allowing ligation of a fluorescent moiety to an azid.

Figure 5:
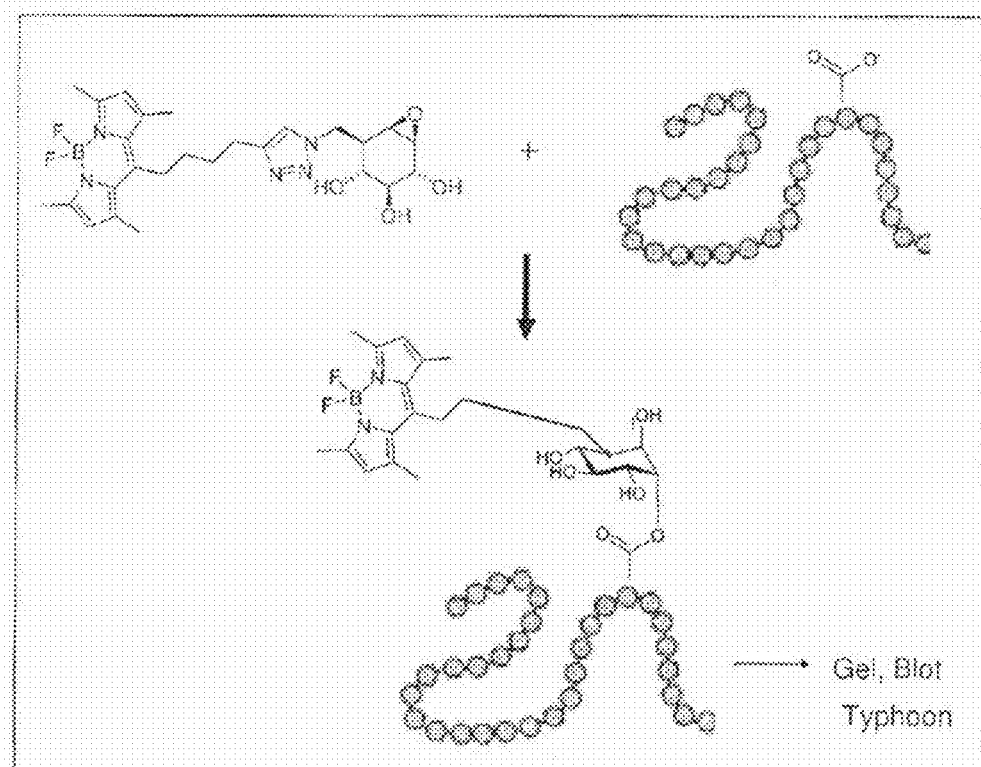

FIG. 5 shows schematically the reaction of an ABP with an enzyme and its detection on a gel or via a blot.

Figure 6A:
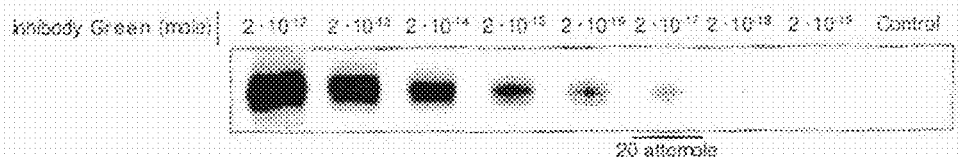

FIG. 6a shows the sensitivity of the detection of the ABP bound to GBA1. Pre-labeled GBA1 (10 nM ABP fluorophore 1-cyclophellitol, for example incubated for 30 min) was put on the gel in decreasing concentrations (total amounts applied per lane are indicated in FIG. 6a). The detection limit on the slab gel is in the low attomole range, visualized with fluorescence imaging.

Figure 6B:
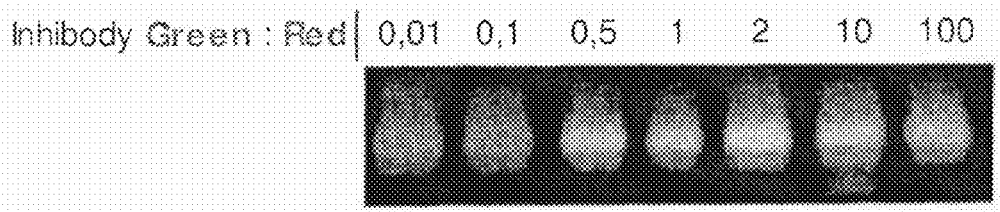

FIG. 6b shows the equipotent labeling of recombinant GBA1 with fluorophore 1-cyclophellitol (Inhibody Green, green fluorescent) and with fluorophore 2-cyclophellitol (Inhibody Red, red fluorescent) as visualized on slab gel with fluorescence imaging. The enzyme was incubated for 30 min. with different proportions of Inhibody Green and Inhibody Red, and the total inhibitor concentration was 10 nM.

FIG. 7 demonstrates the competition of the inventive ABP and azidocyclophellitol for binding to the catalytic centre of GBA1, wherein the binding of ABP is competed by the presence of azidocyclophellitol. In addition the figure shows that prior denatured GBA1 by heat-inactivation (for example 5 min.) is unable to bind the ABP, illustrating the specific labeling of active GBA1 molecules via their catalytic centre. The enzyme was incubated with 10 nM fluorescent probe (Inhibody Green) and 0, 0.1, 1, 10, 100, 1000 µM azidocyclophellitol.

FIG. 8 illustrates the specificity of GBA1 labeling with the inventive ABP. Lysates were prepared from various mouse tissues, i.e., jejunum, spleen, testis and liver, and incubated with 10 nM Fluorophore 1-cyclophellitol for example for 30 min. Labeled lysates were subjected to SDS-PAGE (10% acrylamide). Fluorescent proteins were visualized by fluorescence scanning. In all tissues only GBA1 is visualized with exception of intestinal fractions showing additional MW forms reflecting fragments of lactase and sucrase as identified by LC-MS/MS.

Figure 9:
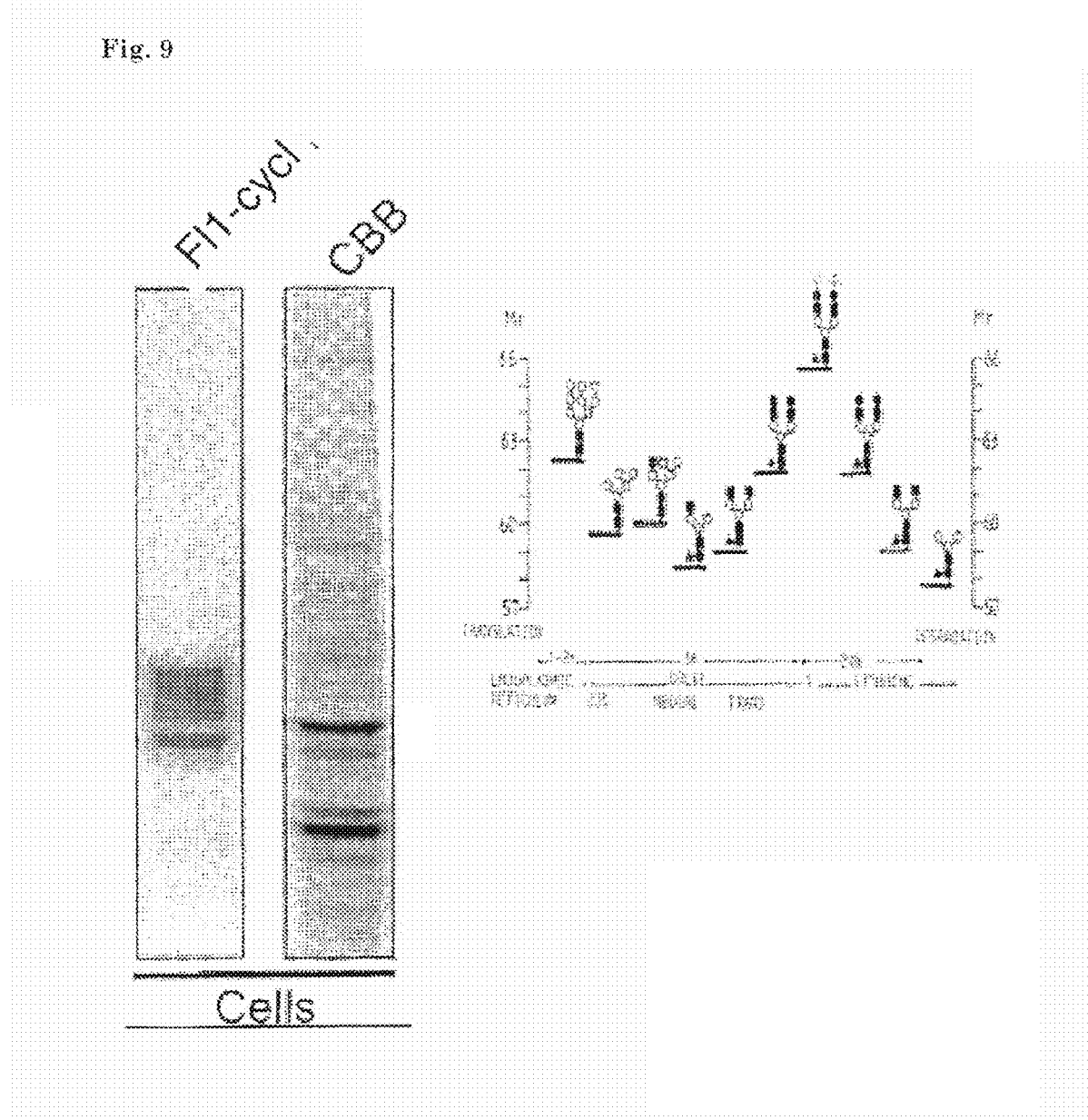

The scheme of FIG. 9 (right panel) shows the life cycle of GBA1 in living cells, i.e. in the endoplasmic reticulum (ER; 61 kDa), in the Golgi (63-66 kDa), and in the lysosomes (57-66 kDa). Fibroblasts contain notoriously a low rate of GBA1 (purification factor vs. total protein >200.000 x).

FIG. 9 (left panel) illustrates that labeling of GBA1 in intact, living cells is feasible and specific. Depicted as example are skin fibroblasts incubated with 100 nM fluorophore 1-cyclophellitol for 1 h. Next, a cell lysate was prepared and subjected onto the gel (0.1 mg cellular protein per lane), fluorescently labelled GBA1 is detected. At the same time almost no unspecific background based on staining of other proteins is detectable. Total protein is visualized by Coomassie brilliant blue (CBB) staining.

FIG. 10a shows fibroblasts labeled with an ABP of the invention in comparison to labeling with an antibody (FIG. 10b). Cultured skin fibroblasts were grown on glass slides, and incubated with 100 nM ABP for 1 hour and were washed afterwards. Cells were subsequently fixed and indirect immuno-fluorescence was performed using an anti-GBA1 monoclonal antibody (8E4). Depicted is the fluorescent staining by ABP (FIG. 10a), the fluorescent staining by the monoclonal anti-GBA1 antibody 8E4 (FIG. 10b), the staining of nuclei with DAPI (FIG. 10c) and the overlay of stains (FIG. 10d).

Figure 11:
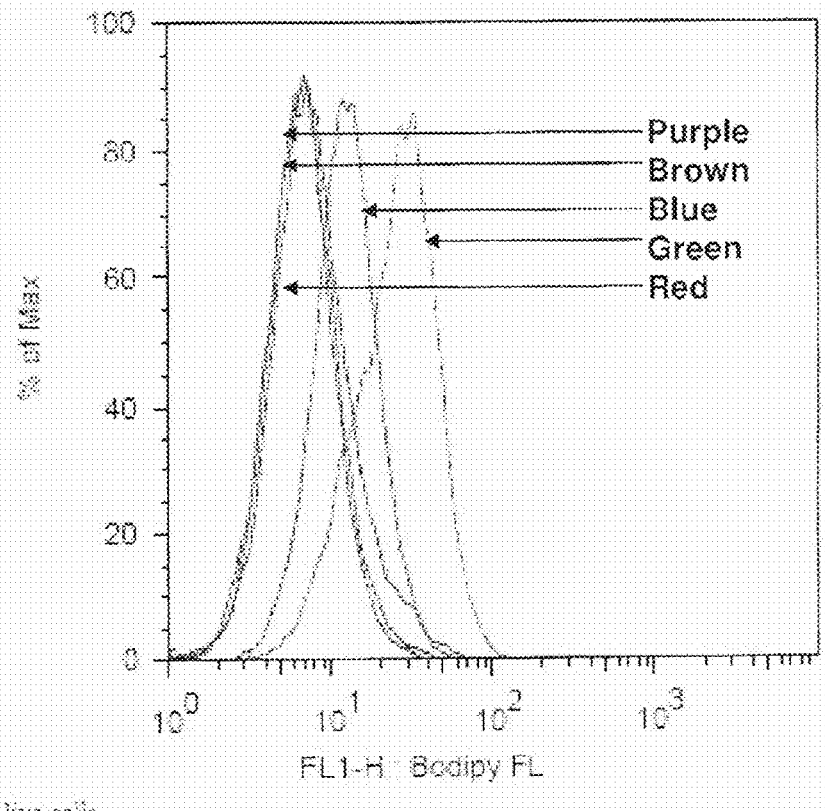
Figure 12:
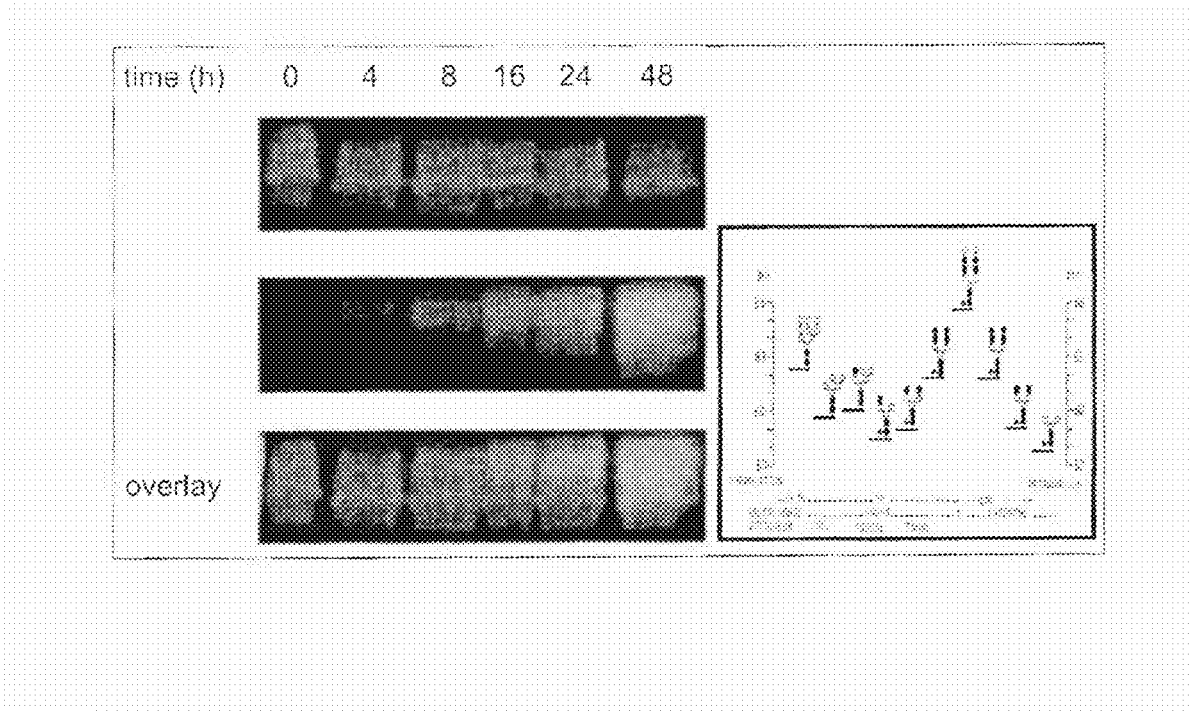

FIG. 11 shows results of FACS. Cultured suspended skin fibroblasts from healthy individuals were preincubated with 0 or 1 mM conduritol B-epoxide (CBE) for 30 min. Conditol-B-epoxide occupies the binding sites for the ABP. Next the cells were incubated with [0, 2 or 10 nM ABP for 1 h and cell-associated fluorescence was detected by =FACS (fluorescence activated cell sorter). The shift to the right indicates the amount of fluorescent per cell, being maximal in cells incubated with 10 nM ABP, and intermediate in cells incubated with 2 nM ABP. In cells pre-incubated with CBE the background fluorescence per cell was very low. Red: no fluorophore 1-cyclophellitol, purple: pre-incubation with CBE+10 nM fluorophore 1-cyclophellitol, brown: pre-incubated with CBE+2 nM fluorophore 1-cyclophellitol, green: pre-incubated without CBE+10 nM fluorophore 1-cyclophellitol, blue: pre-incubated without. CBE+2 nM fluorophore 1-cyclophellitol FIG. 12 shows an example of pulse-chase labeling of GBA1 using two distinctly fluorescent ABPs. Fibroblasts were firstly labeled with 100 nM Fluorophore 1-cyclophellitol (Inhibody Green) labeling all GBA1. Next cells were washed and labeled with 100 nM Fluorophore 2-cyclophellitol (Inhibody Red) labeling all newly formed GBA1 molecules. Cells were harvested at different time points and labeled GBA1 was visualized by SDS-PAGE. The approach allows visualization of life cycle and stability of GBA1 in living cell.

FIG. 13 illustrates the diagnostic application of ABPs for Gaucher disease. Cultured fibroblasts from normal subject, a mildly affected Gaucher patient homozygous for N370S GBA1, a neurologically affected patient homozygous for L444P GBA1 and an extremely severely affected patient completely lacking GBA1 (colloidon baby) were labeled with 100 nM fluorophore 1-cyclophellitol (Inhibody Green) for 1 hour, harvested and lysate subjected SDS-PAGE. The lower panel shows subsequent Western-blot on which GBA1 was visualized using anti-GBA1 monoclonal antibody 8E4. The ABP labeling allows superior and more convenient detection of the GBA1 abnormality.

FIG. 14 demonstrates the feasibility of ABP labeling of GBA1 in living mice. 10 nmoles of fluorophore 1-cyclophellitol were infused into mice intravenously. Animals were sacrificed after 2 hours and tissues were examined on fluorescent GBA1 by microscopy and by preparation of tissue lysate that was next subjected to SDS-PAGE.

Figure 14A:
Figure 14B:
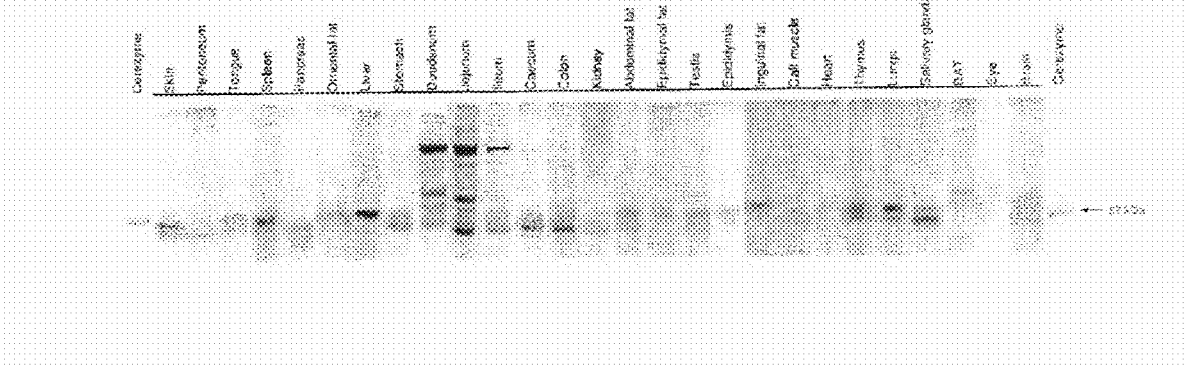

FIG. 14a shows an example of the labeled kidney as visualized by fluorescence microscopy. FIG. 14b shows an example of labeled GBA1 in various tissues, visualized after SDS-PAGE. Note the labeling of additional proteins in the intestinal fractions (sucrase and lactase).

FIG. 15 presents the ABP azido-cyclophellitol in α- and β-conformation.

FIG. 16 shows additional ABPs designed for GBA1. From left to right: Fluorophore 1-cyclophellitol (Inhibody Green)

IC50=2 nM; fluorophore 2-cyclophellitol (Inhibody Red) IC50=2 nM; Fluorophore 3-cyclophelitol (only fluorescent at pH<5.5) IC50=100 nM; Fluorophore 4-cyclophellitol ("BOCLICKY": containing additional biotin moiety allowing capture by streptavidin) IC50=10 nM.

Figure 17:
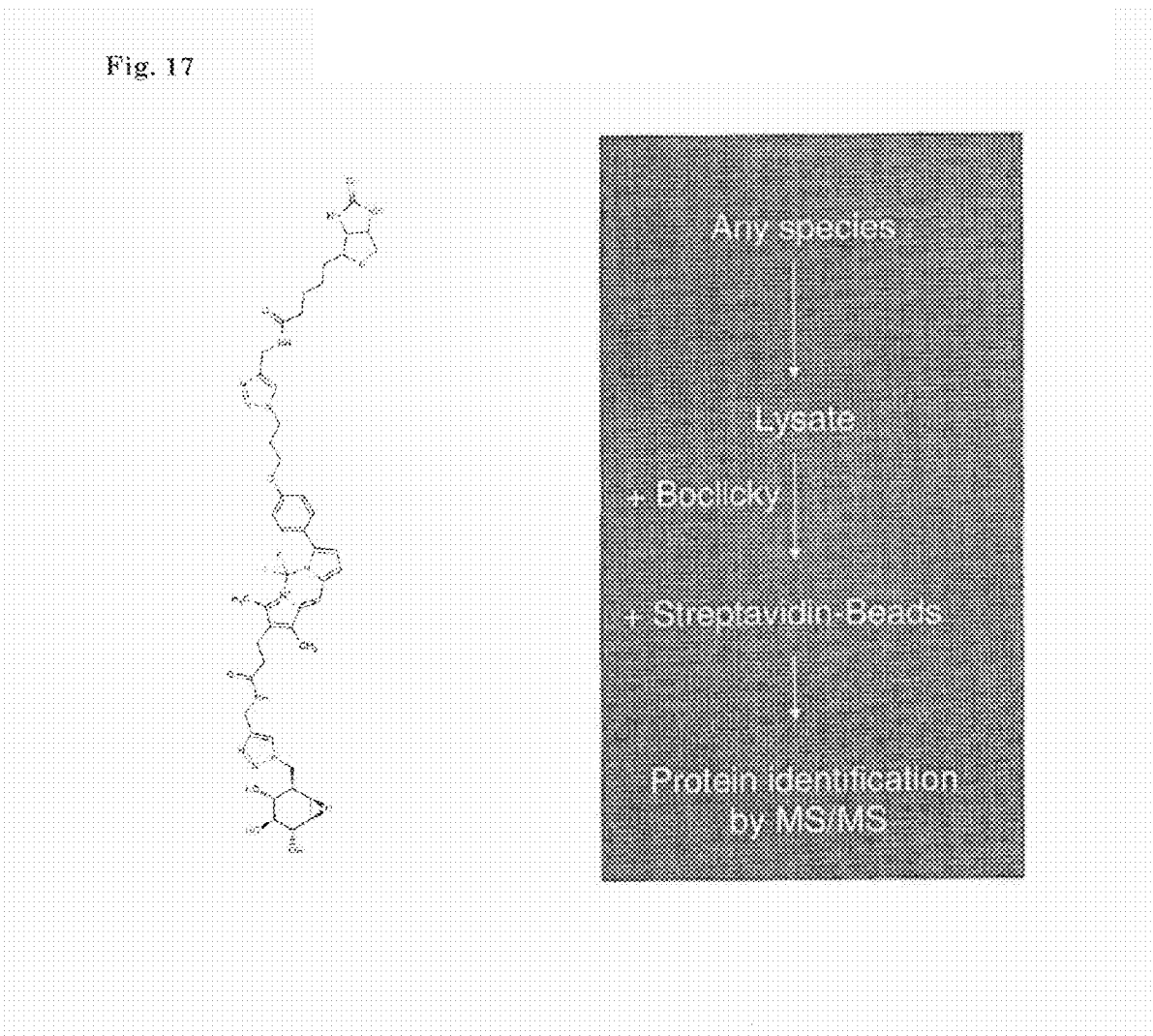

FIG. 17 illustrates schematically the use of the bifunctional ABP containing biotin.

Figure 18:
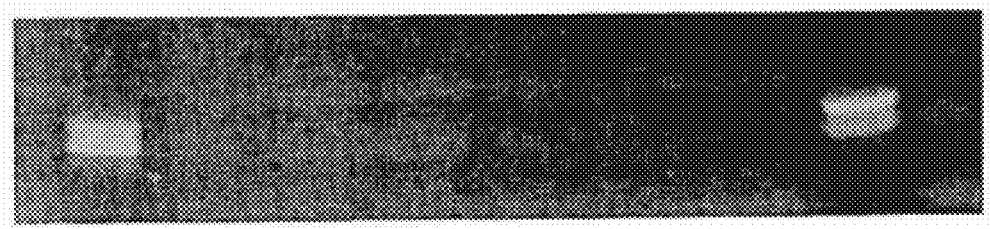

FIG. 18 demonstrates the ABP labeling of recombinant therapeutic GBA1 molecules: Cerezyme (Genzyme Corp.) and Velaglucerase (Shire TKT Corp.), wherein Cerezyme has a smaller MW on SDS-PAGE as Velaglucerase due to difference in N-linked glycan composition. Left lane: Velaglucerase-red labeled with fluorophore 2-cyclophellitol, Cerezyme-green labeled with fluorophore 1-cyclophellitol. Right lane: Cerezyme-red labeled with fluorophore 2-cyclophellitol, Velaglucerase-green labeled with fluorophore 1-cyclophellitol.

Figure 19:
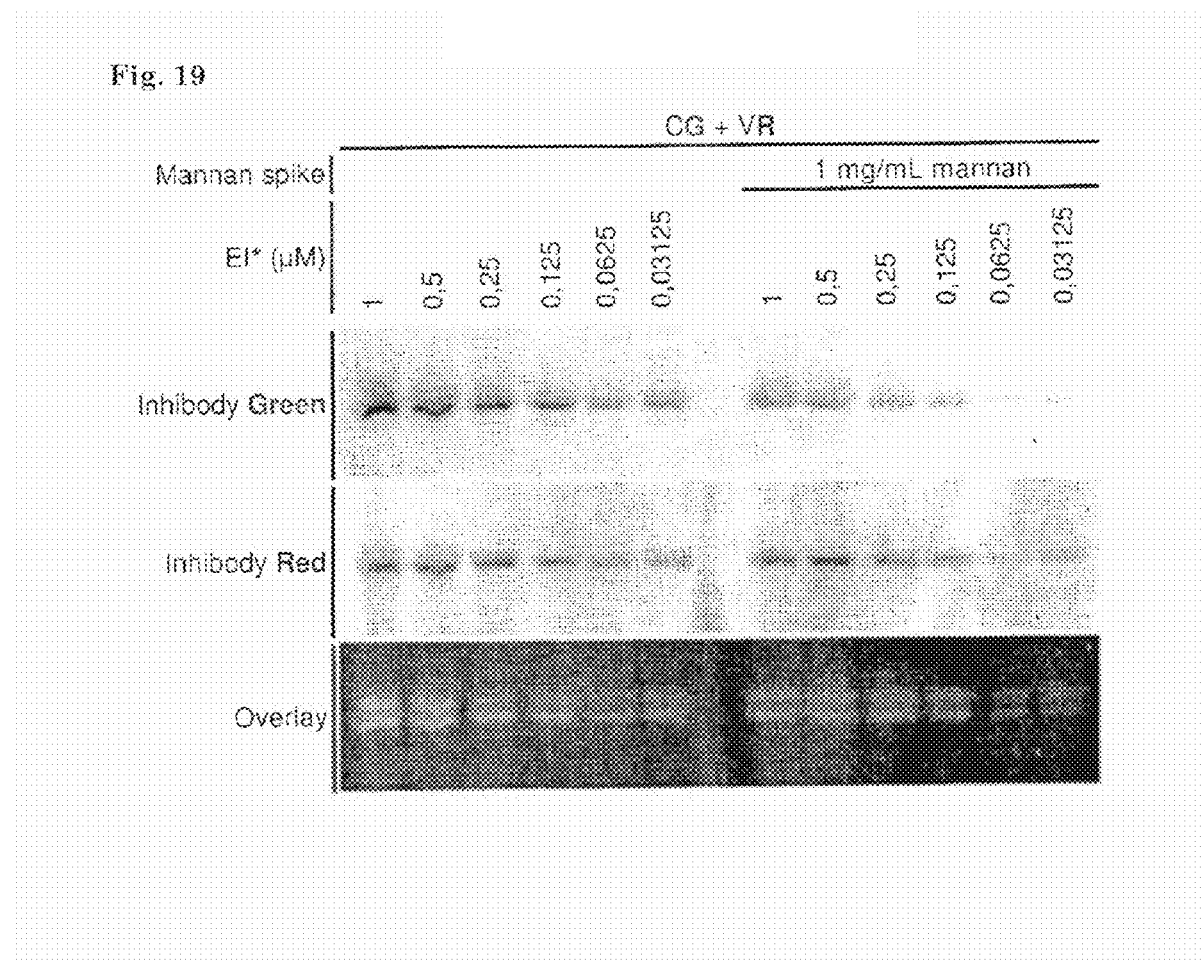

FIG. 19 renders an example of use of ABP-labeling of therapeutic enzymes. Cultured human macrophages were incubated with 1:1 mixture of distinctly pre-labeled therapeutic enzymes in the absence or presence of mannan. The experiment allows comparative analysis of mannose-receptor medicated uptake of Velaglucerase and Cerezyme.

Figure 20A:
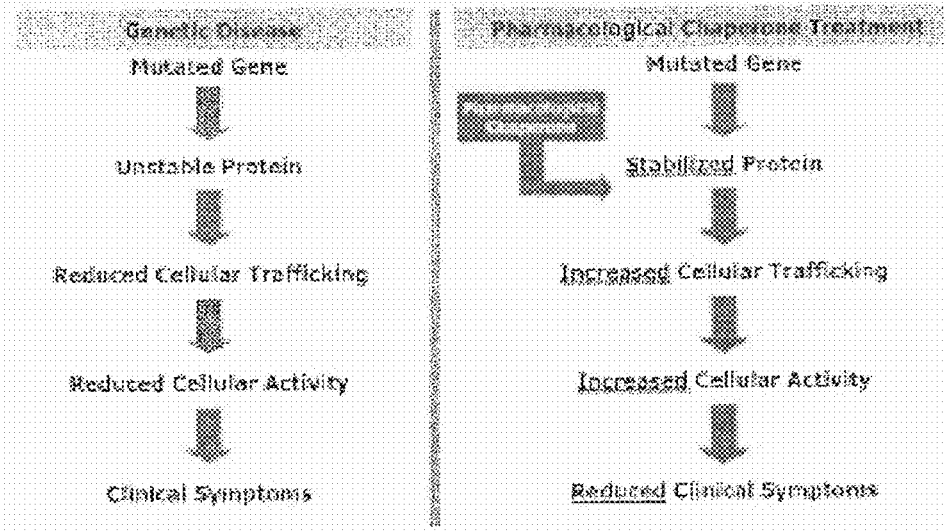
Figure 20B:
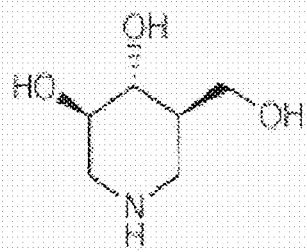
Figure 20C:
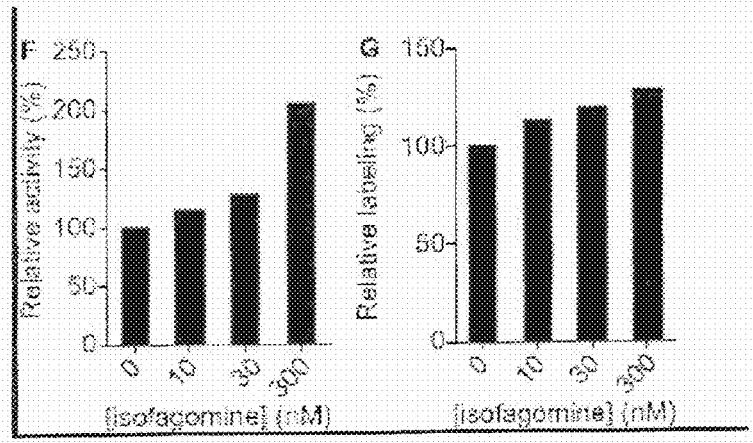

FIG. 20 presents a schematic illustration of Gaucher treatment (FIG. 20a) via the chaperone isofagimine, whose structure is separately shown in FIG. 20b. FIG. 20c presents the results of fibroblasts of Gaucher patients (N370S GBA1 homozygote), which were grown for 3 days in the presence of the indicated concentration of isofagomine. The fibroblasts were labeled with Fluorophore 1-cyclophellitol (for example 20 nM for 1 hour), wherein about 50% of cellular GBA1 was labeled. The labeled fibroblasts were harvested and lysed: Left panel F shows the enzymatic activity in the lysate, which was measured with 4-methylumbelliferyl-beta-glucosidase as substrate reflecting total GBA1. Right panel G shows the amount of in vivo fluorescently labeled GBA1, which was determined by SDS-PAGE and fluorescence imaging. The results indicate that in vivo high concentrations of isofagomine inhibit GBA1 as shown by the reduced labeling with ABP.

Figure 21A:
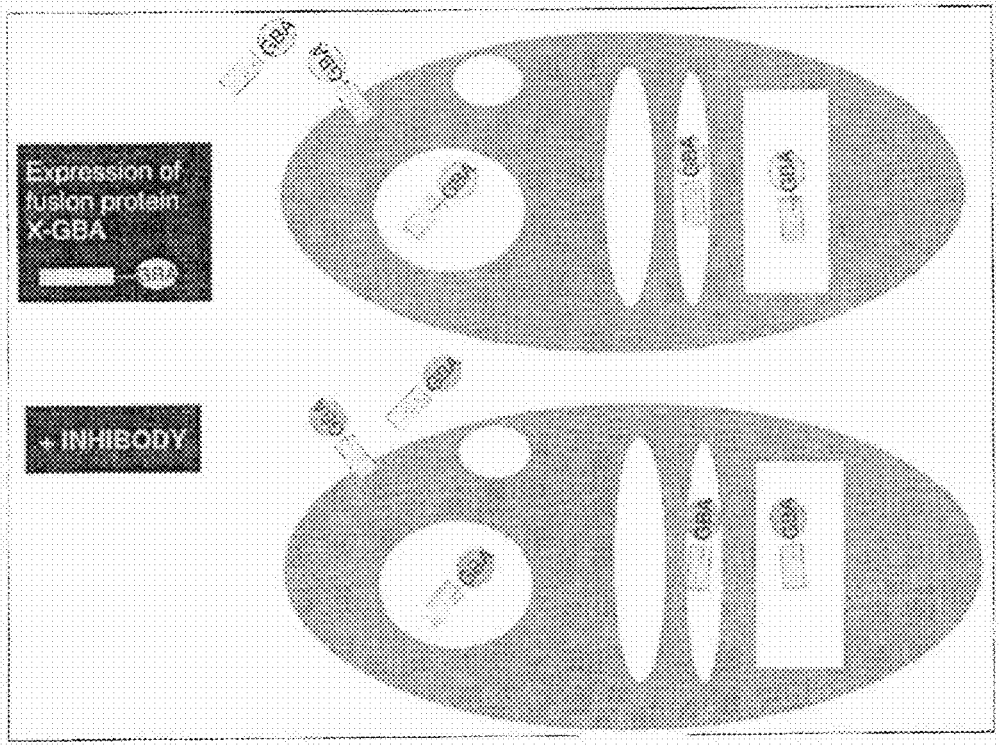
Figure 21B:
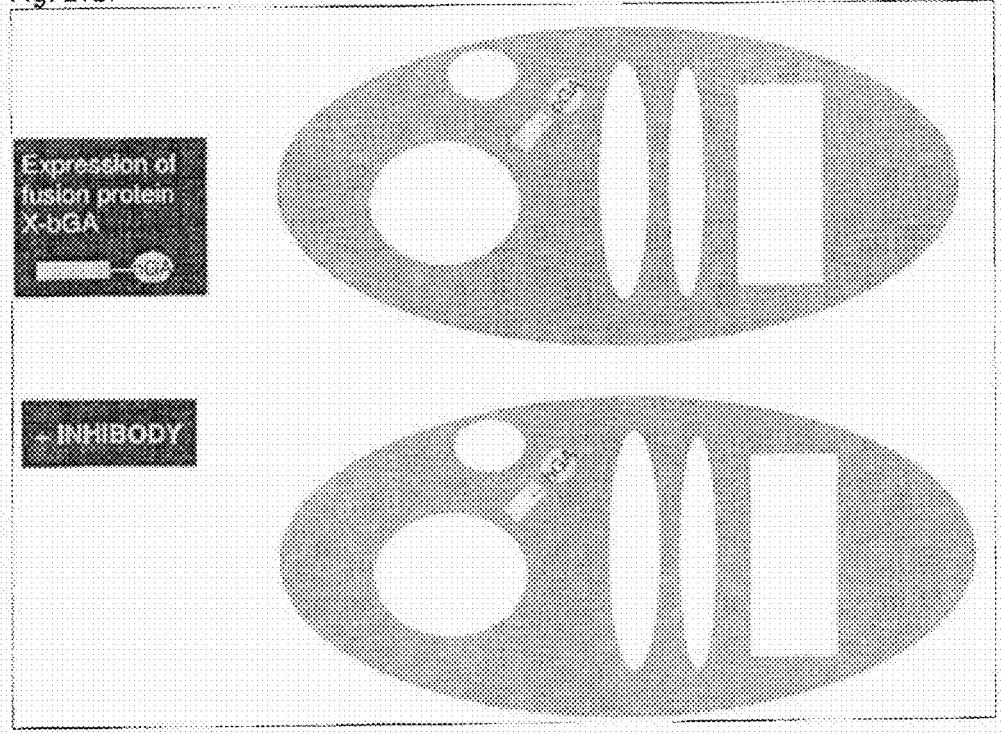

FIG. 21 describes the use of ABPs to visualize glucosidase-fusion proteins in living organism, isolated tissue or cells. A fusion protein with GBA1 (to be used for example for proteins with signal peptide that reside in ER, Golgi, endosomes, lysosomes, plasma membrane or are secreted, FIG. 21a), and a fusion protein with an appropriate glycosidase (bGA) (to be used for proteins without signal peptide that reside in cytosol, mitochondria, peroxisomes, FIG. 21b.

FIG. 22 Compounds for example 3

FIG. 23 Structures of isofagomine, CBE, cyclophellitol, KY170, MDW933 and MDW941.

FIG. 24 In vitro labeling of GBA with MDW933 and MDW941. (a) Labeling of recombinant GBA (Cerezyme) with mixtures of MDW933 and MDW941 detected on slab gel. Left: labeling with the indicated amount of MDW933 in the presence of 100 nM MDW941. Right: labeling with the indicated amount of MDW941 in the presence of 100 nM MDW933. (b)

Sensitivity of detection and labeling. Upper panel: Cerezyme (2 pmol) was incubated with an excess of MDW933 (1 mM) and dilutions applied on gel. Lower panel: Cerezyme (2 μmol) was incubated with a decreasing amount of MDW933. (c) Activity of Cerezyme (2 μmol) was blocked by incubating with CBE (2 mM) or AMP-DNM (2 mM) or by boiling in 1% (w/v) SDS before labeling with MDW933. (d) Effect of the pH on inhibition and enzymatic activity. The activity of GBA was determined at various pH values, normalized for the activity at pH 5.2 and plotted (circles). Inhibition by MDW933 was examined at the same pH ranges (open squares). Data represent mean values±s.d. (e) Fluorescent labeling of GBA in homogenates of RAW cells using MDW933 (100 nM) (7.5% SDS-PAGE gel). Proteins were detected by fluorescence imaging (left lane) and Coomassie Brilliant Blue (CBB) staining (right lane). (f) Fluorescent labeling of mouse tissue lysates exposed to MDW933 (100 nM) (10% SDS-PAGE gel). Arrows indicate the molecular weight of Cerezyme. For uncut gels, see FIG. 40.

Figure 25:
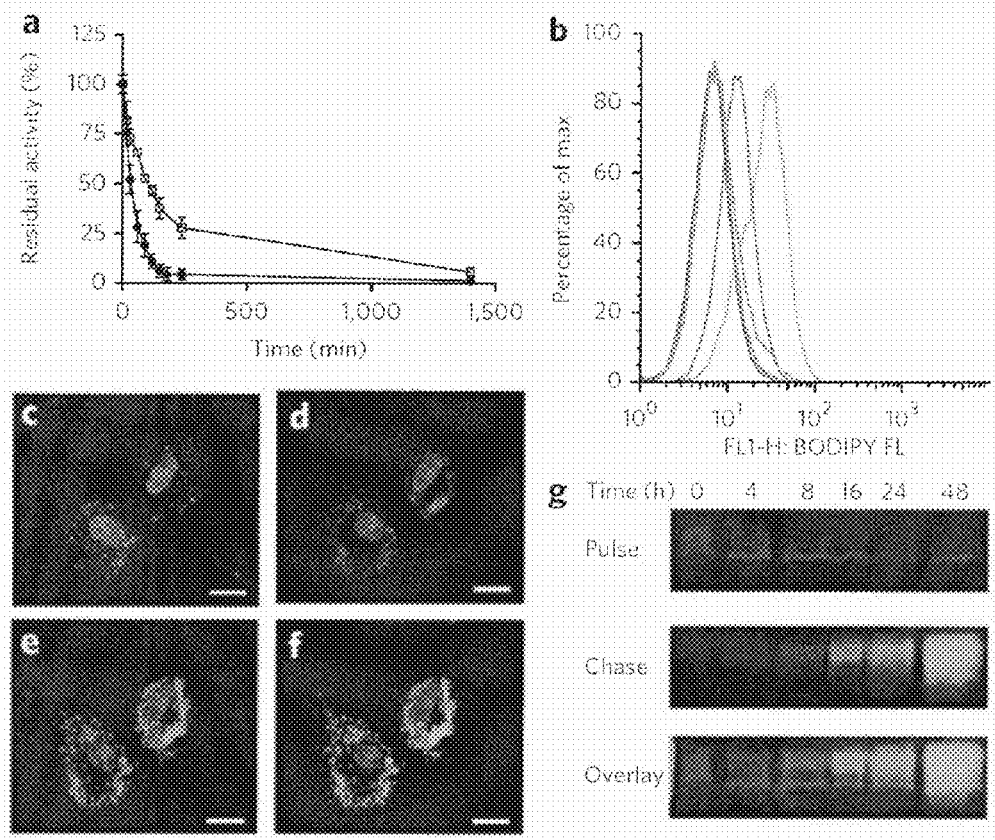

FIG. 25 In situ labeling of glucocerebrosidase. (a) Inactivation of GBA by MDW933 (squares) and MDW941 (circles) in situ. Fibroblasts incubated with the probes (5 nM) for the indicated time were homogenized, and residual activity was determined with 4-methylumbelliferyl β-D-glucopyranoside. Data represent mean values±s.d. (b) FACS analysis. Cells were treated with 0 nM (red line), 2 nM (blue line) and 10 nM (green line) MDW933 for 300 min. Control cells were pretreated with CBE (0.3 mM) and incubated with 2 nM (brown line) and 10 nM (purple line) MDW933. (c-f) Representative spectral imaging micrographs of cells labeled with MDW941. (c) Autofluorescence (white). (d) MDW941 BODIPY fluorescence of GBA (red). (e) AlexaFluor488 fluorescence of GBA visualized with monoclonal Ab 8E4 (green). (f) Overlay of d and e. In all pictures, nuclei are stained with DAPI (blue). Scale bar represents 20 μm. (g) Pulse-chase experiment. Cells were incubated overnight with 10 nM MDW941 (pulse, upper panel) and then with 10 nM MDW933 for the indicated time (chase, middle panel). Lower panel: overlay of the pulse and the chase. Because of the use of low concentration of MDW933 during the first 8 h of the chase, incomplete labeling of newly formed GBA molecules was accomplished. For uncut gels see FIG. 41.

Figure 26:
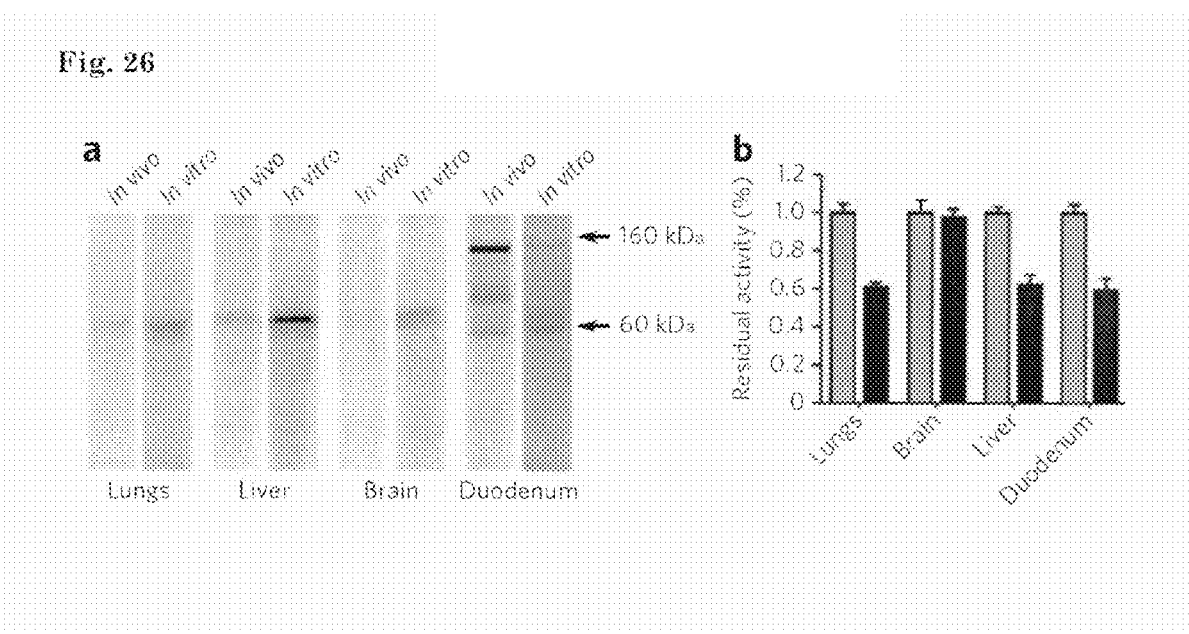

FIG. 26 Labeling of glucocerebrosidase in mice. Adult mice received intravenously 100 pmol green fluorescent MDW933 and were killed after 2 h. (a) Tissue lysates were incubated with excess (100 nM) red fluorescent MDW941 for 30 min to label unreacted GBA. In vivo labeled GBA (left panels) and in vitro labeled GBA (right panels) were visualized separately. For uncut gels, see FIG. 42. (b) Residual enzymatic activity in tissues of treated mice (black) was determined with 4-methylumbelliferyl β-D-glucopyranoside substrate and expressed as percentage of the matched control animal (gray). Data represent mean values±s.d.

Figure 27:
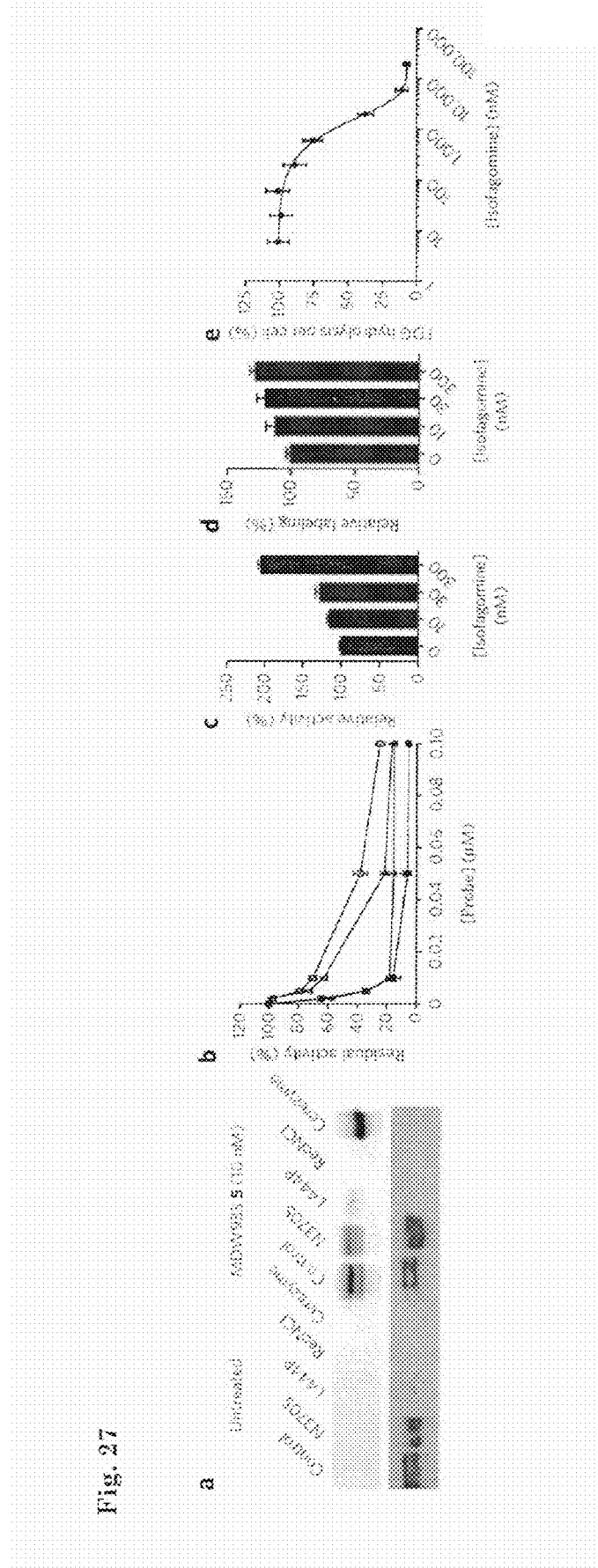

FIG. 27 Labeling of mutant forms of glucocerebrosidase. (a) Detection of GBA in Gaucher fibroblasts by labeling of wild-type and homozygous N370S, L444P and RecNCI collodion fibroblast with 10 nM MDW933 for 60 min. GBA was visualized by in-gel fluorescent scanning (top panel) and by western blotting with 8E4 antibody. For uncut gels, see FIG. 43. (b) Inactivation curves of MDW933 (open symbol) and MDW941 (solid symbols) in N370S (triangles) and control fibroblasts (squares). Residual activity was determined with 4-methylumbelliferyl β-D-glucopyranoside. Data represent mean values±s.d. (c,d) Impact of isofagomine on N370S GBA. In a typical experiment, fibroblasts from the N370S GBA homozygote were incubated with various isofagomine concentrations for 1 week. Data represent mean values±s.d. (c) Relative GBA activity in cell lysates observed with 4-methylumbelliferyl β-D-glucopyranoside assay after incubating. (d) Quantification of the fluorescent readout of in situ MDW941-labeled GBA activity. (e) Relative lysosomal GBA activity observed as hydrolysis of FDG per cell. Fibroblasts were first treated for 20 min with noted concentrations of isofagomine and subsequently incubated with FDG substrate. FDG fluorescence was assessed by FACS analysis. Data represent mean values±s.d.

Figure 28:
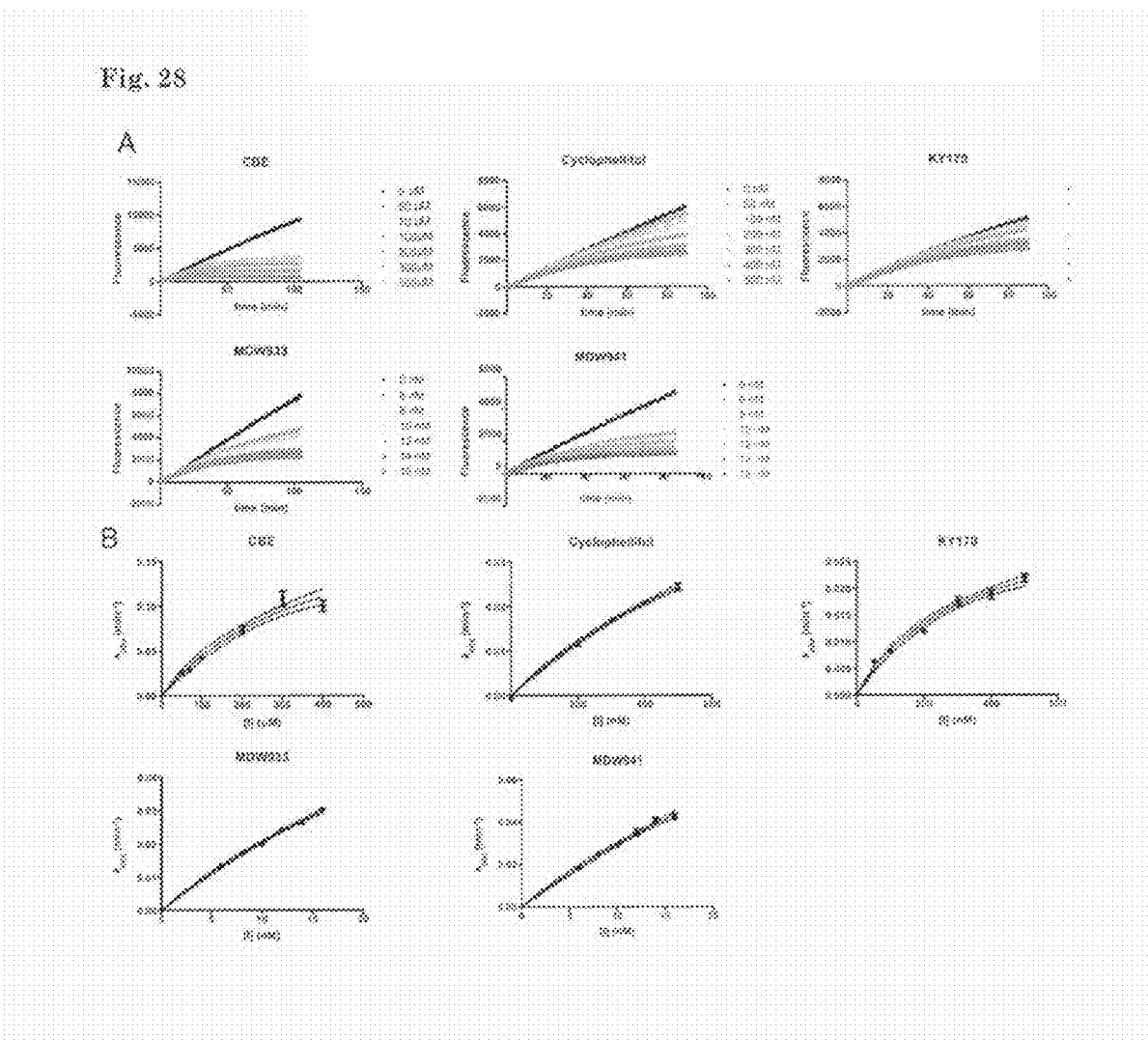

FIG. 28 Inhibition of GBA by probes. (A) Progress curves. An average of three individual measurements which is corrected for the blank and corrected to zero is represented. (B) k' versus [I]$_0$ plots. Data points represent mean of nine individual k'±s.e.m. Solid lines represent best fit according to the described equitation. Dashed lines represent 95% intervals.

FIG. 29 Molecular docking of MDW933 and MDW941. Lowest energy conformers with rotatable bonds docked on crystal structure of glucocerebrosidase (pdb 2VE3).

Inhibitor molecule is shown as sticks, GBA as semi-transparent space-filling model, and active-site residues E235 and E340 as dark-blue sticks (left and right, respectively) (A). Docking of MDW933 shows two common docking conformations (C, D) of −8.2 and −8.1 kcal/mol, docking of MDW941 resulted in −9.6 kcal/mol binding affinity (B). (E-H) Docking comparison with CBE-bound GBA (2VT0). Top (E) and side (G) view of CBE docked on crystal structure 2V3E (E340, dark red; E235, dark blue; CBE, dark green) on top of covalent-bound CBE crystal structure 2VT0 (E340, pink; E235, light blue; CBE, pale green). Top (F) and side (H) view of an overlay of MDW933 (bright green).

Figure 30:
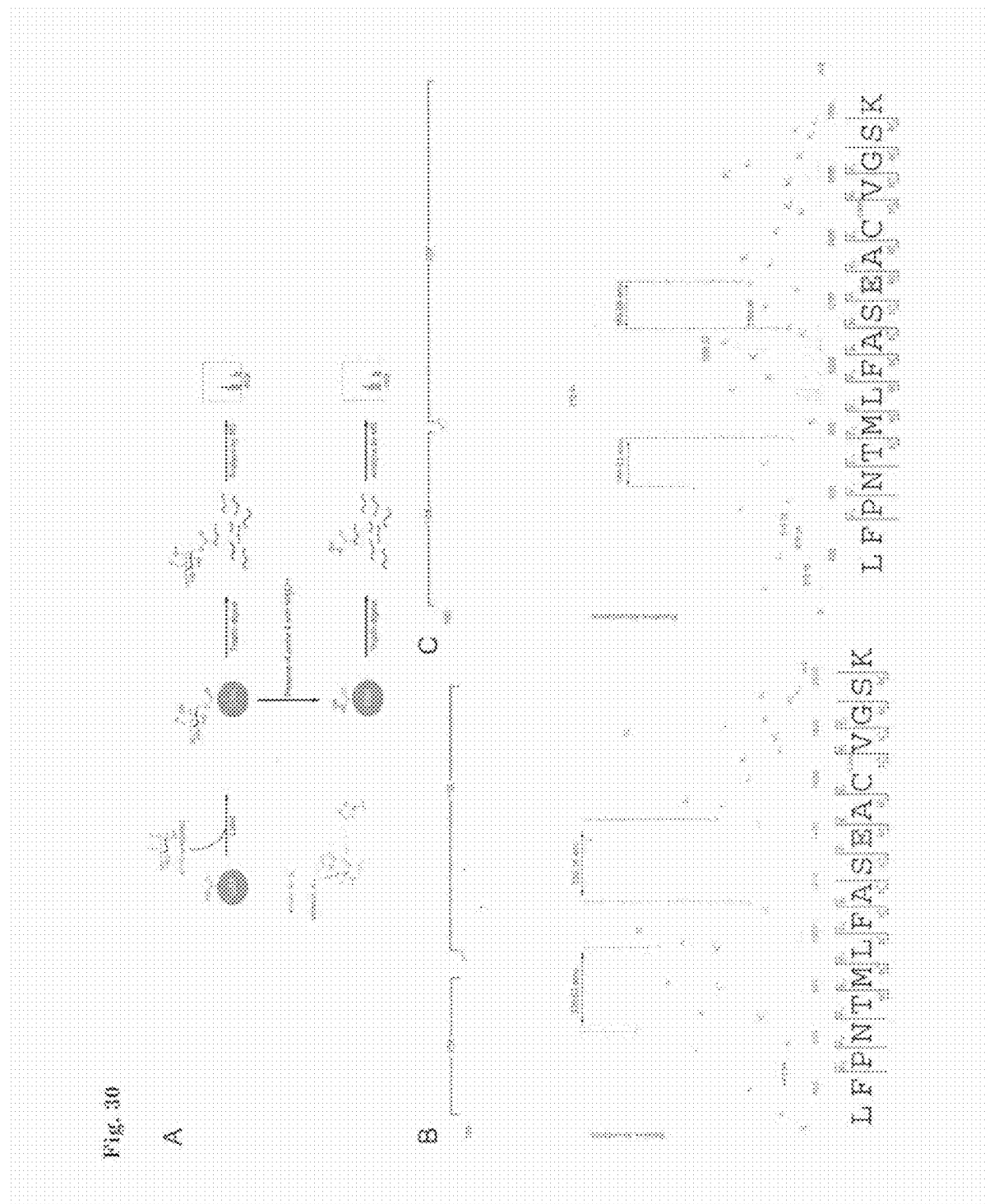

FIG. 30 Mass spectrometric analysis of covalently labeled GBA. (A) Schematic representation of the experiment. Recombinant GBA labeled with KY170 4 is digested with trypsin and analyzed by LC tandem MS (upper path). To release the label and to install the hydroxamic acid residue, GBA labeled with MDW933 5 is treated with hydroxylamine prior to tryptic digestion and analysis by LC-MS/MS (lower path). KY170 4 (B) and MDW933 5 (C) are covalently linked to E340 in recombinant GBA. One peptide that was selected for fragmentation in the tryptic digest of GBA labeled with 4 had a parent mass (2071.99 amu) and one peptide that was selected for fragmentation in the tryptic digest of GBA labeled with 5 and treated with hydroxylamine had a parent mass (1885.92 amu). The mass of these peptides was 201.09 amu and 15.02 amu increased compared to the theoretic mass (1870.90 amu) of the sequence of the tryptic peptide containing residue E340 (shown in bold red). This is in accordance with the addition of the mass of respectively KY170 4 (201.08 amu) and hydroxylamine (15.01 amu). Furthermore it is clear from the tandem mass spectra shown, that the adduct mass is localized at the glutamic acid residue of the peptide resulting in a delta-mass of 329.03 amu between y6, y7 and 330.14 amu between b10, b11, and a delta-mass of 144.03 amu between y6, y7 and 143.98 amu between b10, b11 for respectively KY170 4 (B) and MDW933 5 (C). This is consistent with the mass of glutamic acid covalently linked to KY170 4 (330.12 amu) and hydroxylamine (144.05 amu) at that site. Ccam, cysteine residue with carbamidomethyl modification.

Figure 31:
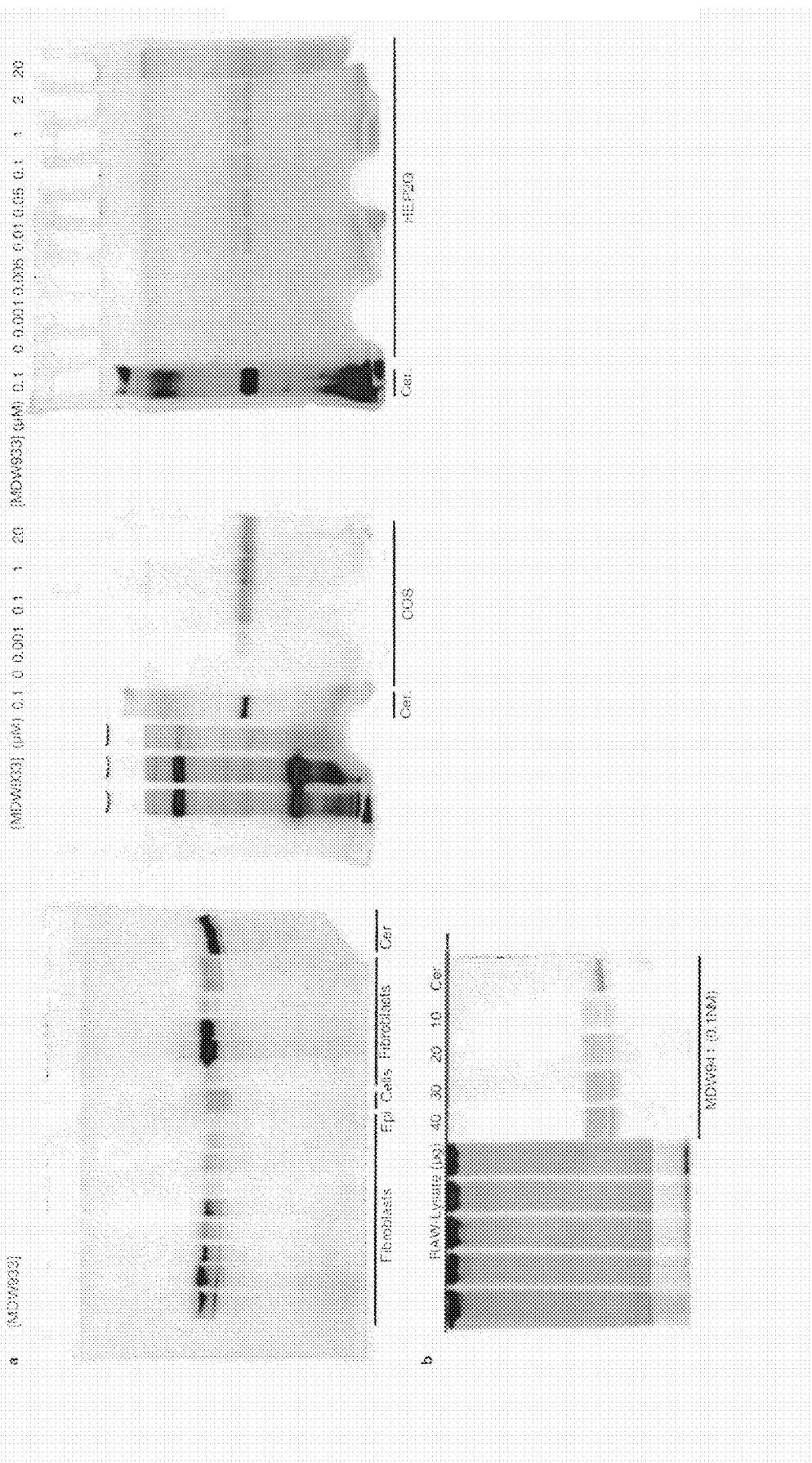

FIG. 31 Labeling of GBA in cell lysates. (a) MDW933 5 (1 nM to 10 µM) selectively labeled GBA in fibroblast (left), COS cell lysate (middle) and HEP2G cell lysate (right). (b) Selective labeling of GBA in RAW-lysates (10-40 µg) using MDW941 6 (0.1 µM).

Figure 32:
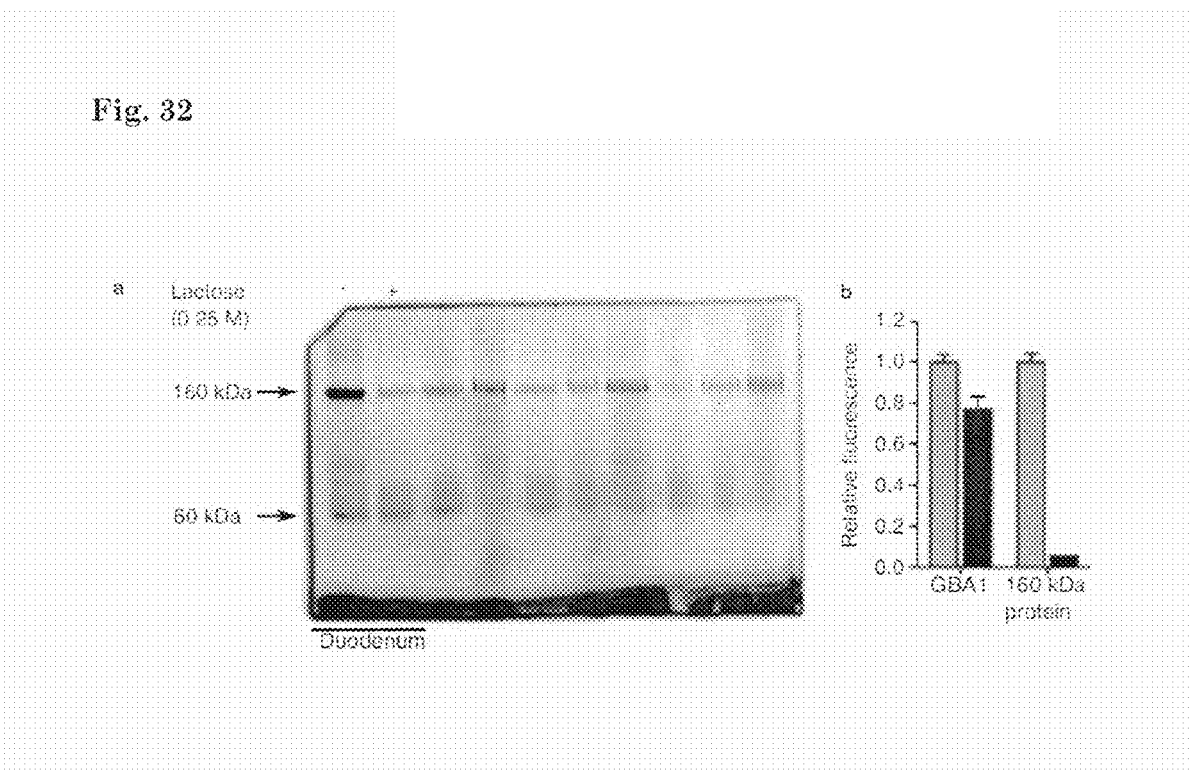

FIG. 32 Indenfication of the 160 kDa protein. (a) Labeling of lactase by MDW933 5 in homogenates of the duodenum of mice in the presence or absence of lactose (250 mM). (b) Quantification of the observed fluorescent signal. Data represent mean values±s.d.

Figure 33:
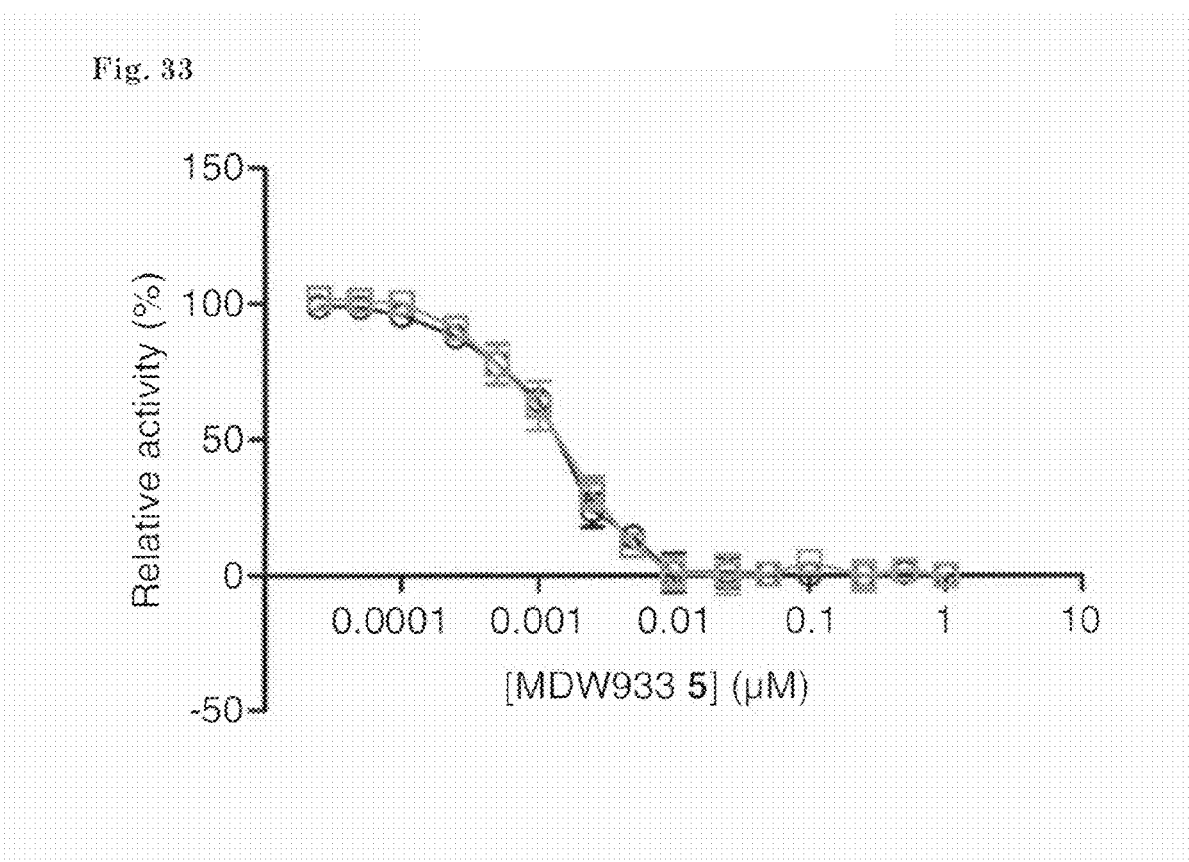

FIG. 33 In situ inhibition of GBA by MDW933 5 at 18° C. (black line/circles) and 37° C. (red line/squares). Data represent mean values±s.d.

Figure 34:
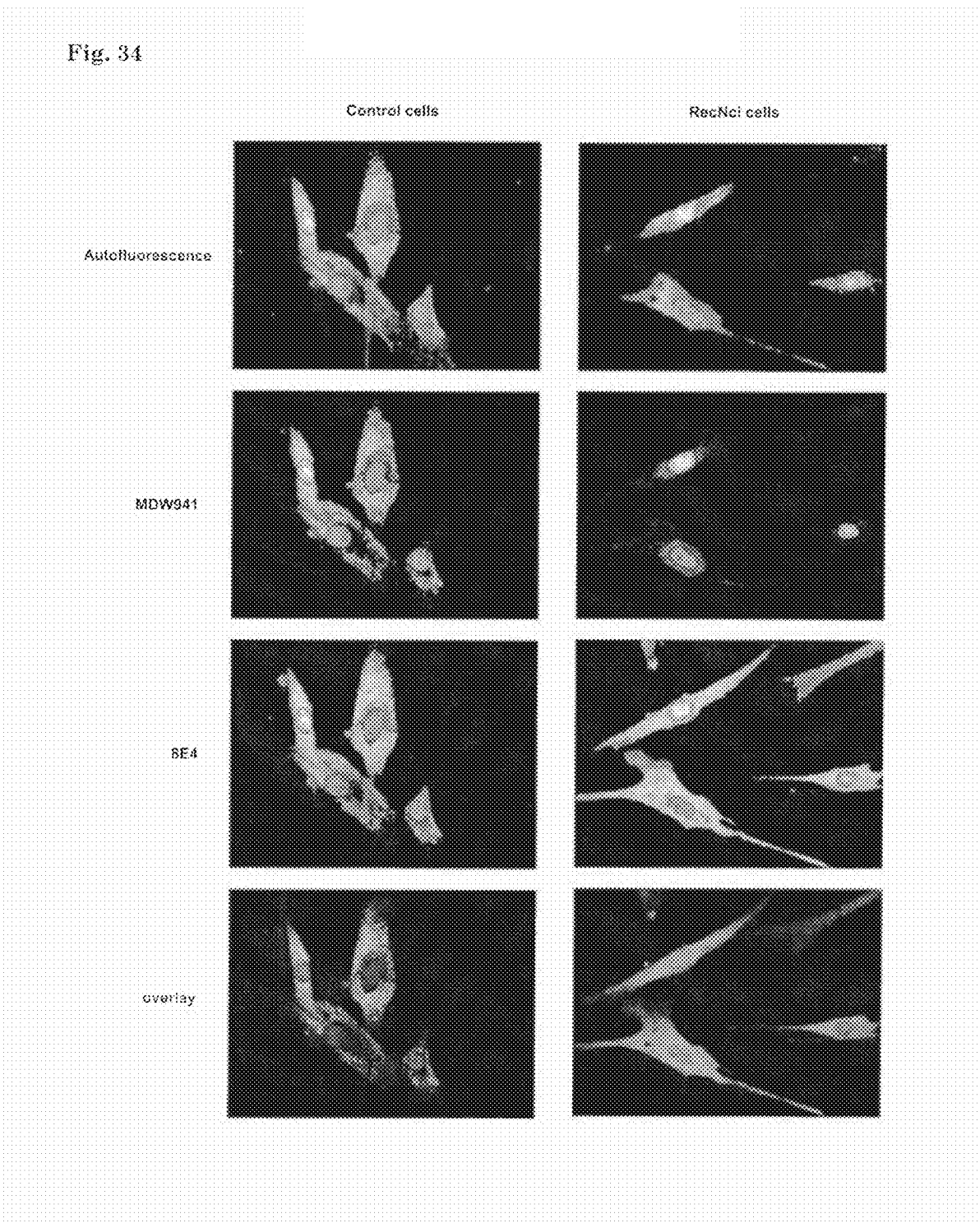

FIG. 34 Representative spectral imaging micrographs of control (left column) and gaucher (right column) cells labeled with MDW941 6. First row of panels represent a heat map of the autofluorescence. The second row of panels show a heat map of the observed BODIPY-fluorescence of GBA labeled with MDW941 6 (unmixed and separated from the autofuorescence). The third row shows a heat map of the Alexa488-fluorescence of GBA visualized with monoclonal Ab 8E4 (unmixed and separated from the autofuorescence). In the fourth row an overlay of the unmixed and corrected signals of BODIPY and Alexa488 fluorescence is shown. Scale bar represents 20 µM.

Figure 35:
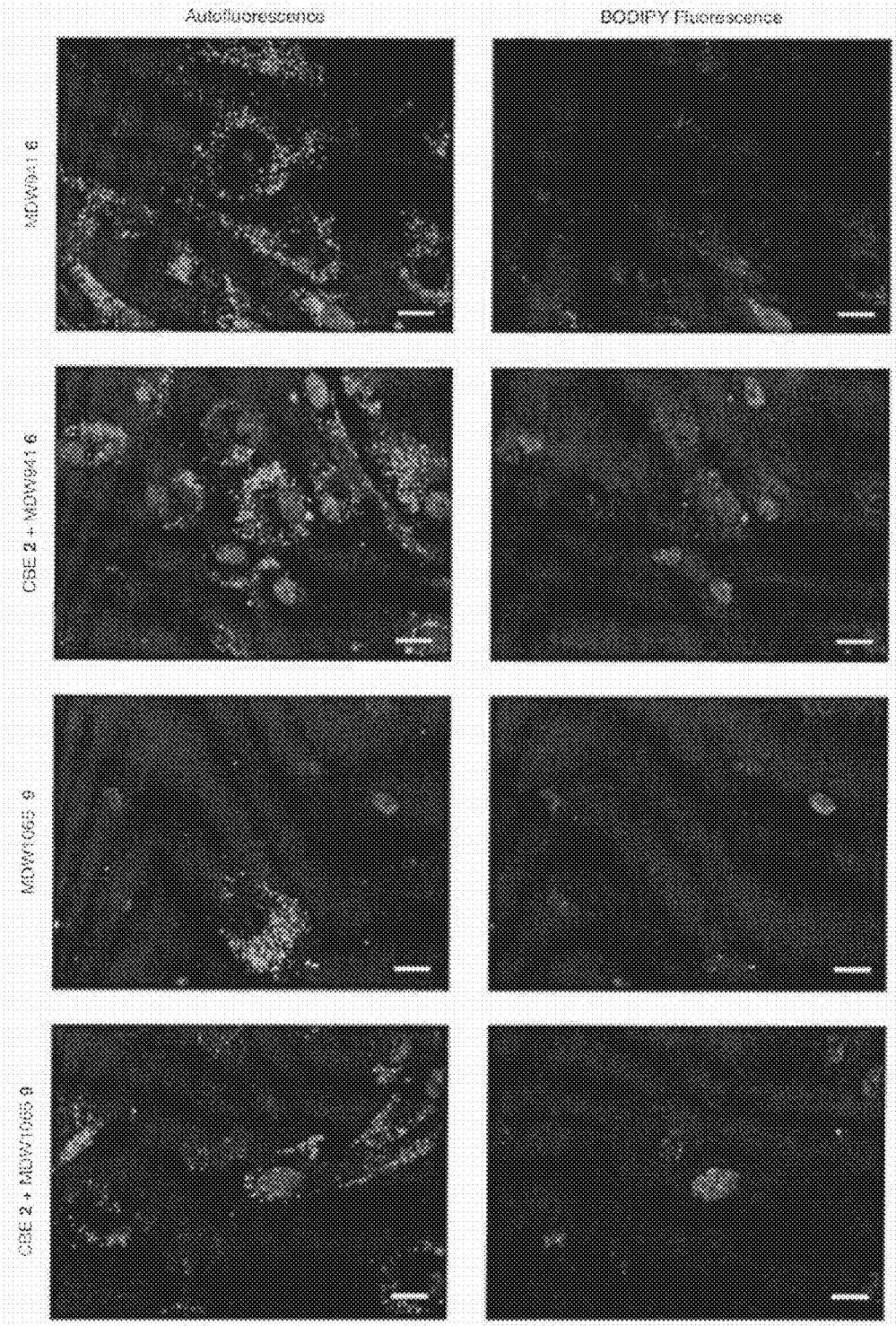

FIG. 35 Representative spectral imaging micrographs of cells labelled with MDW941 6 or control probe MDW1065 9 in the presence or absence of CBE 2. The left column shows the autofluorescence and the right column shows the unmixed BODIPY fluorescence signal. Upper row, micrographs of cells treated with MDW941 6 in the absence of CBE 2 are shown. The second row of micrographs shows the cells treated with MDW941 6 in the presence of CBE 2 (3 mM). The third row shows micrographs obtained after labelling cells with the non-reactive control probe MDW1065 9. In the final row, micrographs of cells treated with a combination of MDW1065 9 and CBE 2 is shown. Scale bar represents 20 µM.

Figure 36:
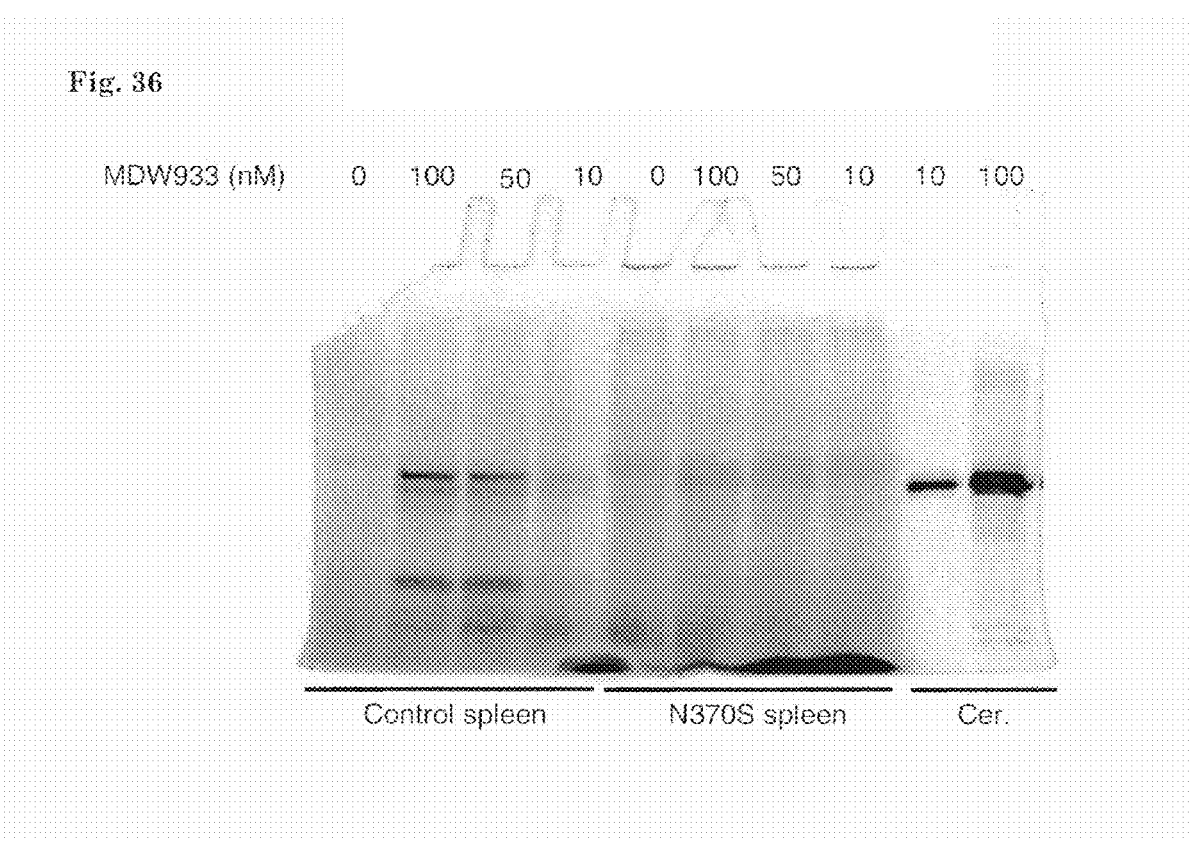

FIG. 36 Labeling of GBA in Gaucher and control spleen. Tissue homogenates were treated with 0, 10, 50 and 100 nM MDW933 5 for 60 min.

Figure 37:
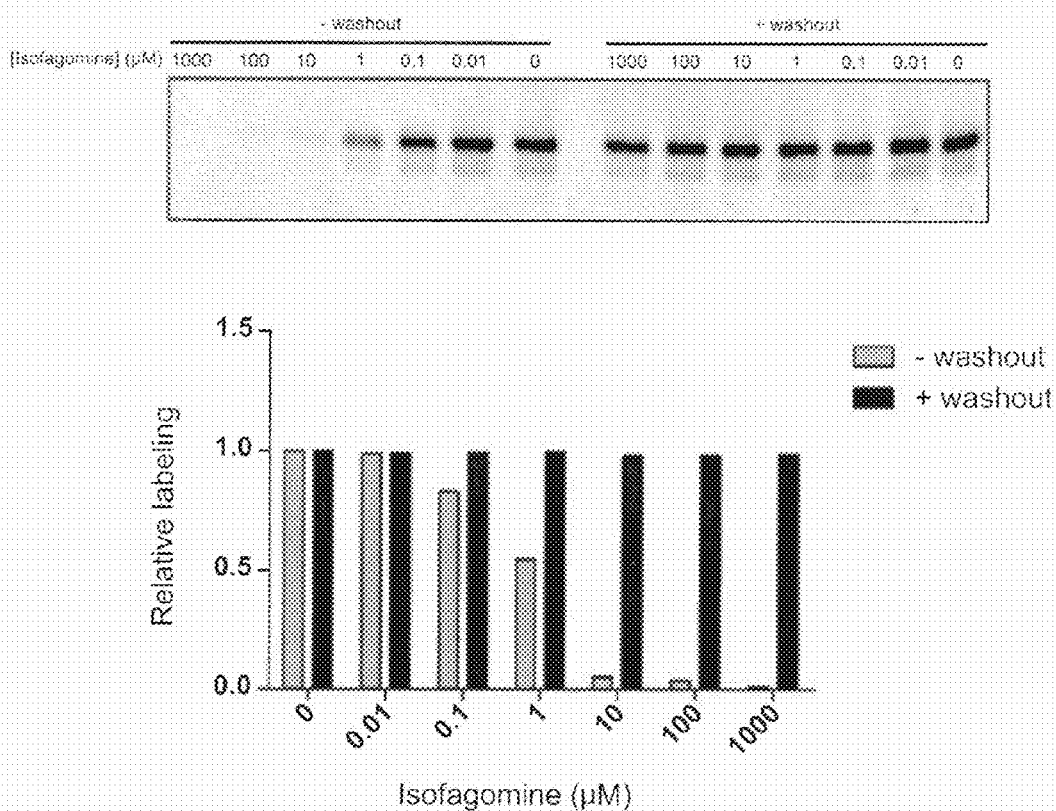

FIG. 37 The reversibility of isofagomine inhibition. Recombinant GBA attached to monoclonal antibody 8E4 immobilized to Sepharose beads was pre-incubated for 15 min with increasing concentrations of isofagomine at pH 5.2 in the presence of taurocholate (0.2% w/v) and Triton X-100 (0.1% v/v). The bead suspension was washed with the same buffer or not and subsequently incubated for 15 min with 10 nM MDW933 5.

Figure 38:
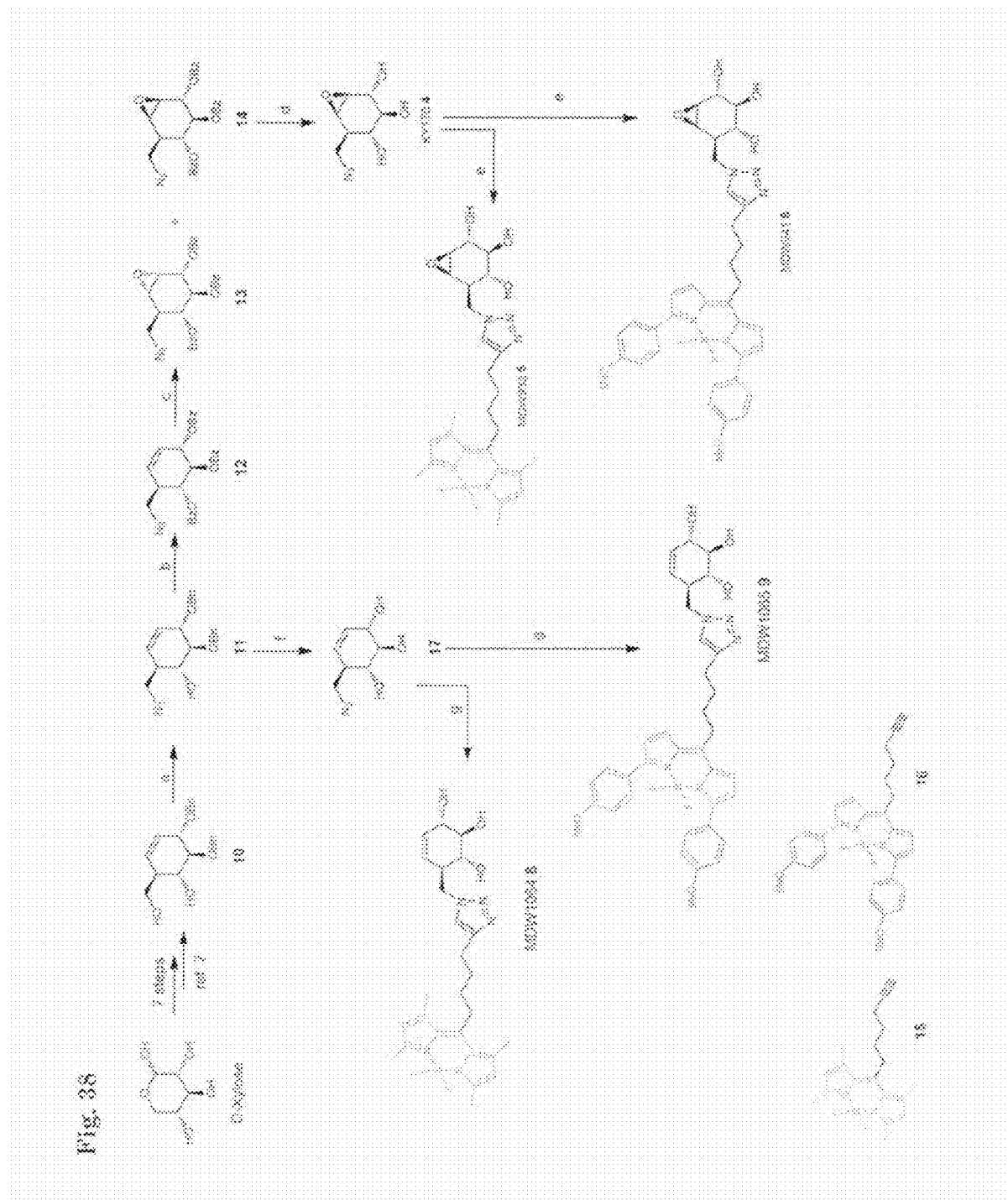

FIG. 38 Scheme 1. Synthesis of KY170 4, MDW933 5 and MDW941 6. Reagents and conditions: (a) i) p-TosCl, Et$_3$N, CH$_2$Cl$_2$, 0° C.; ii) NaN$_3$, DMF, 60° C., 71%; (b) i) BCl$_3$, CH$_2$Cl$_2$, −78° C., ii) BzCl, pyridine, 70%; (c) CF$_3$COCH$_3$, Oxone, NaHCO$_3$, MeCN/H$_2$O, 13: 49%, 14: 20%; (d) NaOMe, MeOH, 75%; (e) 15 or 16, CuSO$_4$ (10 mol %), sodium ascorbate (15 mol %), Tol/tert-BuOH/H$_2$O, 90° C., MDW933 5: 56%, MDW941 6: 77%; (f) BCl$_3$, CH$_2$Cl$_2$, −78° C.; (g) 15 or 16, CuSO$_4$ (10 mol %), sodium ascorbate (15 mol %), DMF, MDW1064 8: 72%, MDW1065 9: 70%.

Figure 39:
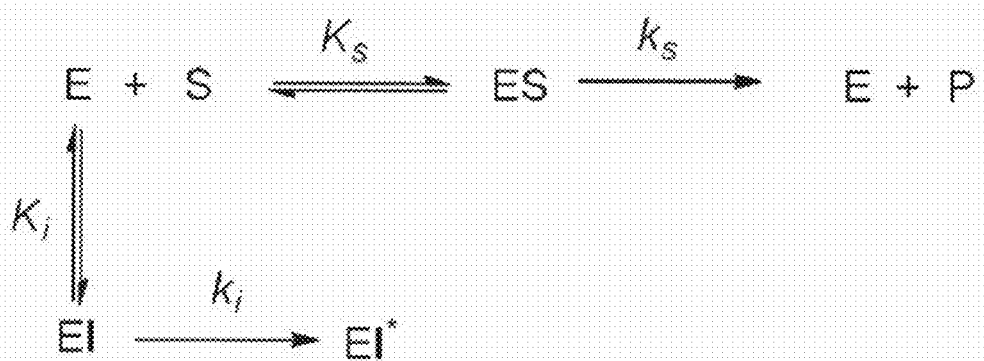

FIG. 39 Scheme 2. Schematic representation of the process occurring during a continuous substrate assay.

Figure 40:
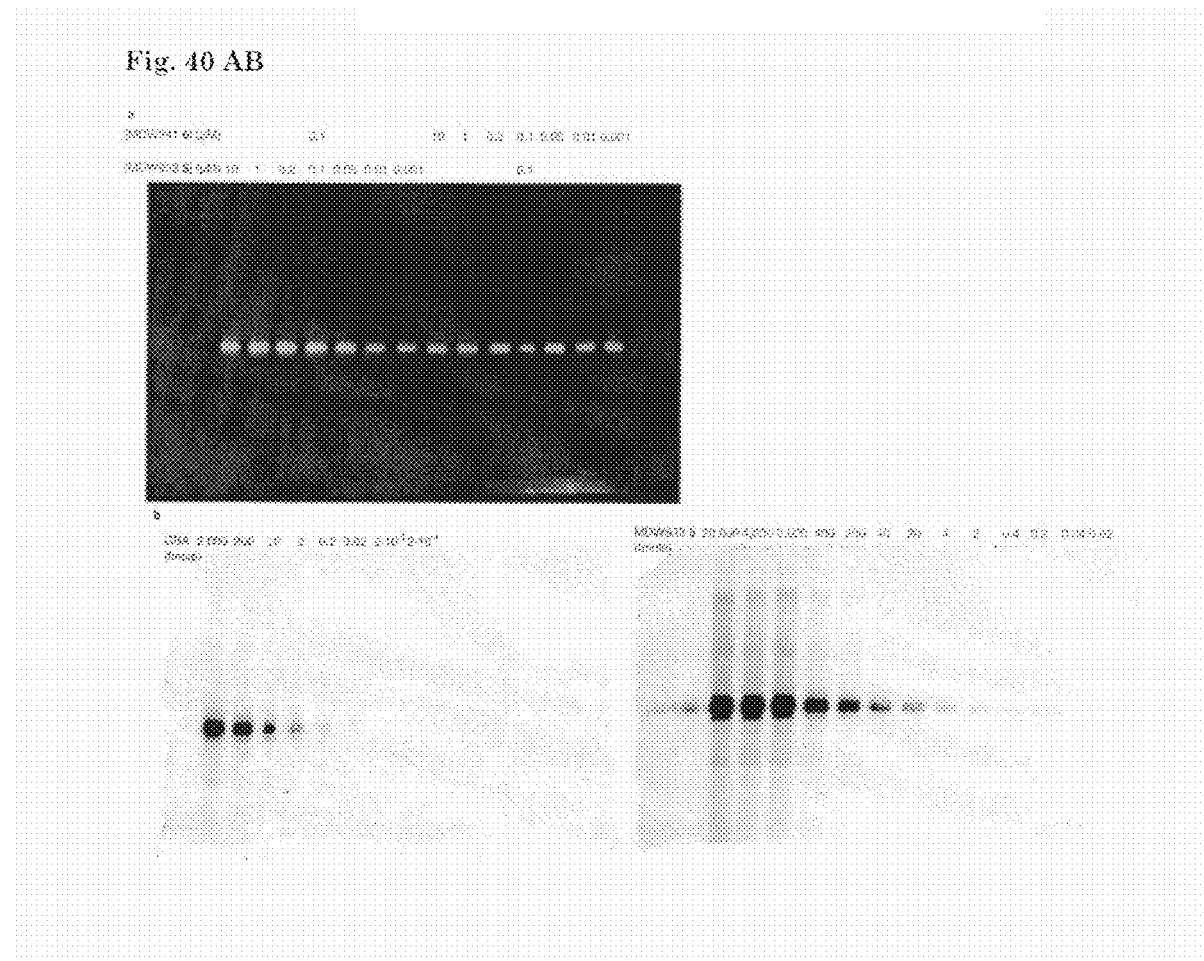

FIG. 40 Uncut gel images of FIGS. 24a, 24b, 24c, 24e and 24f are shown as respectively a, b, c, d, e.

Figure 41:
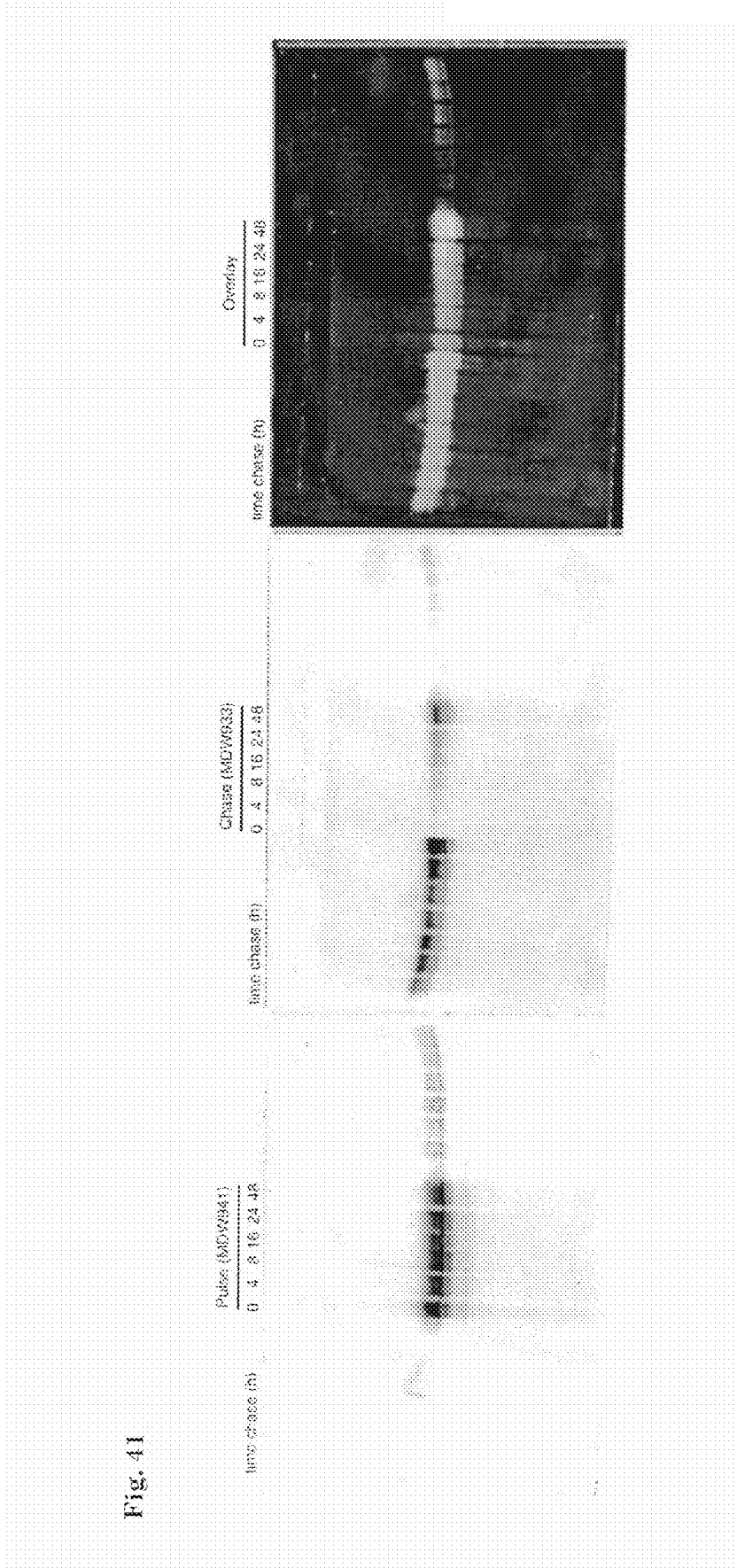

FIG. 41 Uncut gel images of FIG. 25d are shown.

Figure 42:
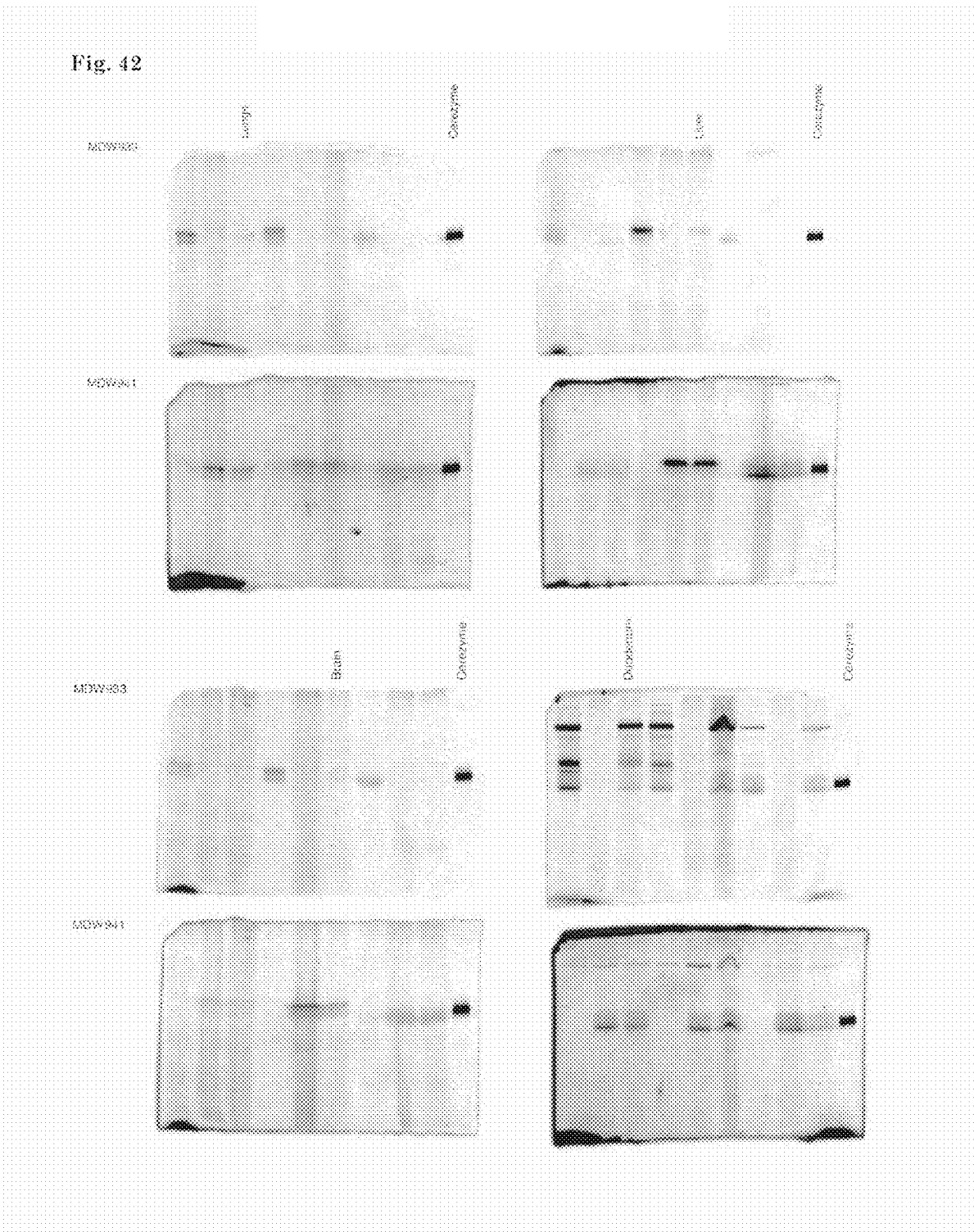

FIG. 42 Uncut gel images of FIG. 26a are shown.

Figure 43:
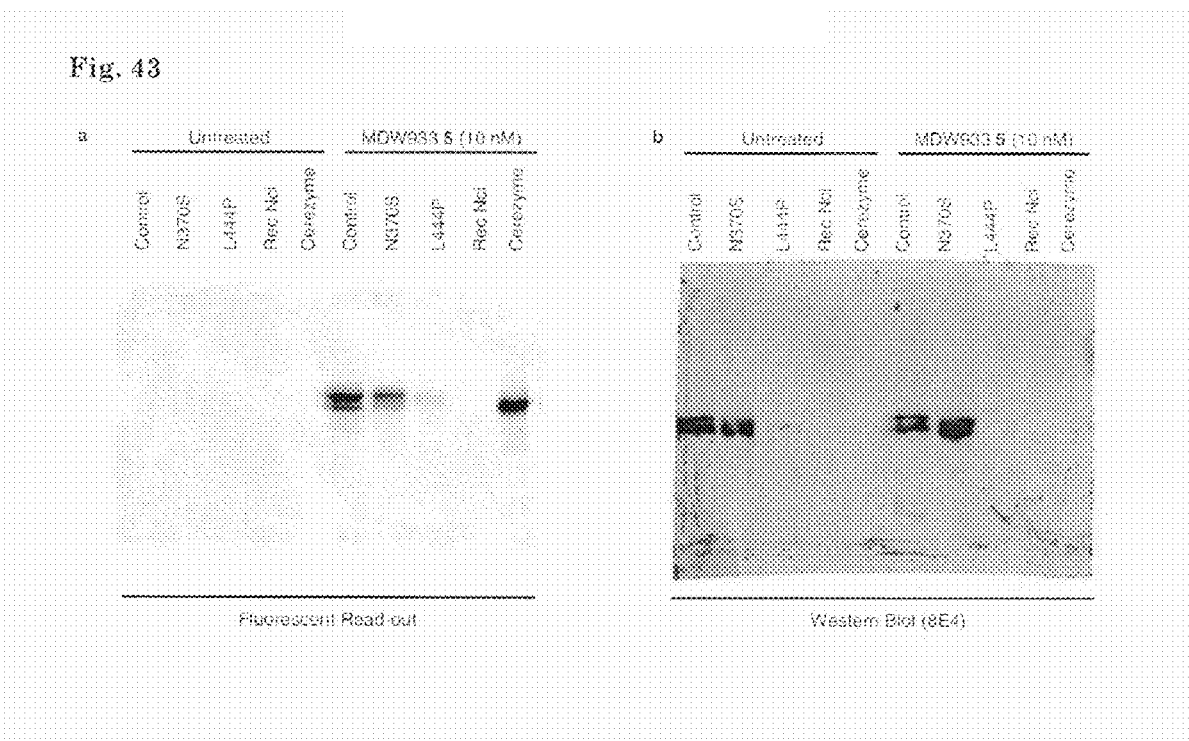

FIG. 43 Uncut gel images of FIG. 27a. Left: fluorescent read-out. Right: GBA is visualized using Western blotting FIG. 44 Generation of novel probes for other glycosidases.

Figure 45:
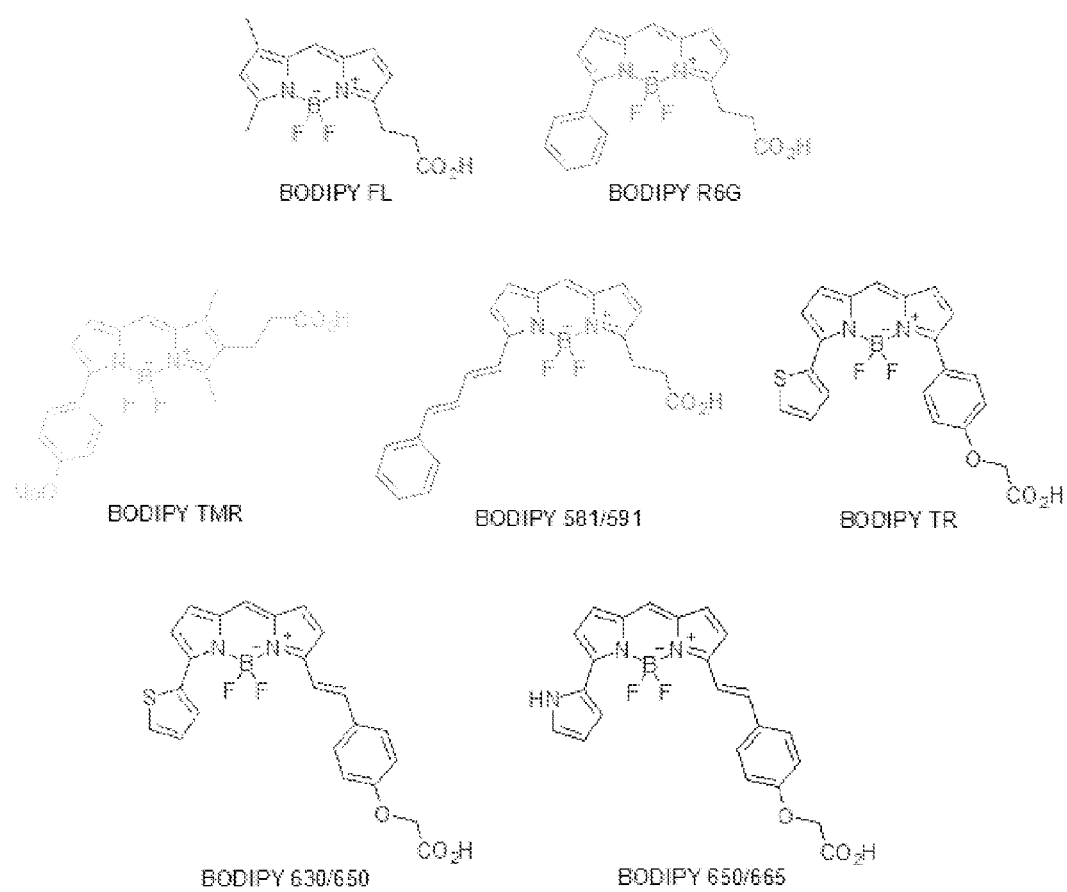

FIG. 45 Examples of preferred fluorophores

FIG. 46 Alexa Fluor emission spectrum and Bodipy emission spectrum.

FIG. 47 Synthesis of an anybody wherein a Bodipy fluorophore is linked to a cyclophellitol wherein the epoxide group is replaced with an azarine group.

Figure 48A:
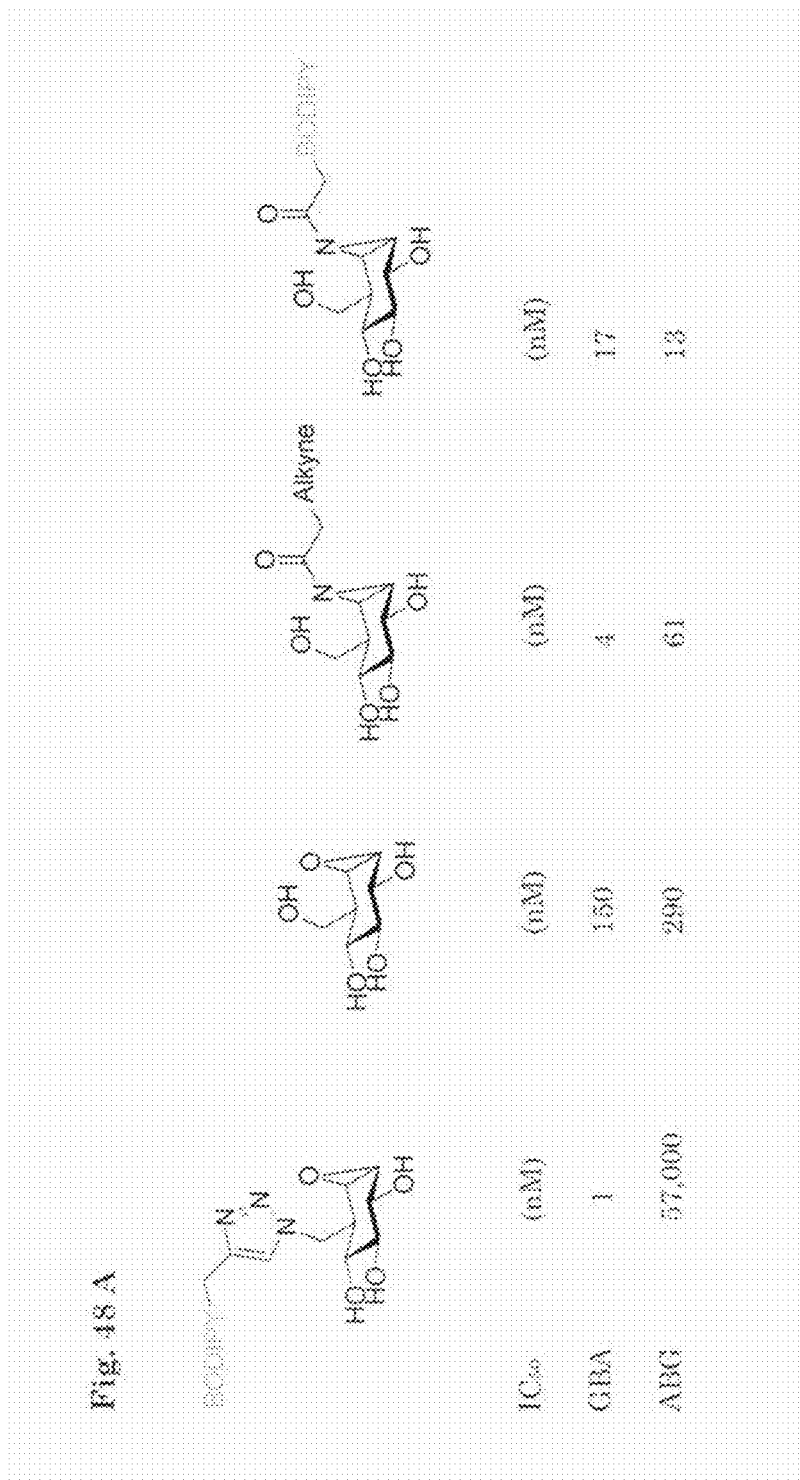
Figure 48:
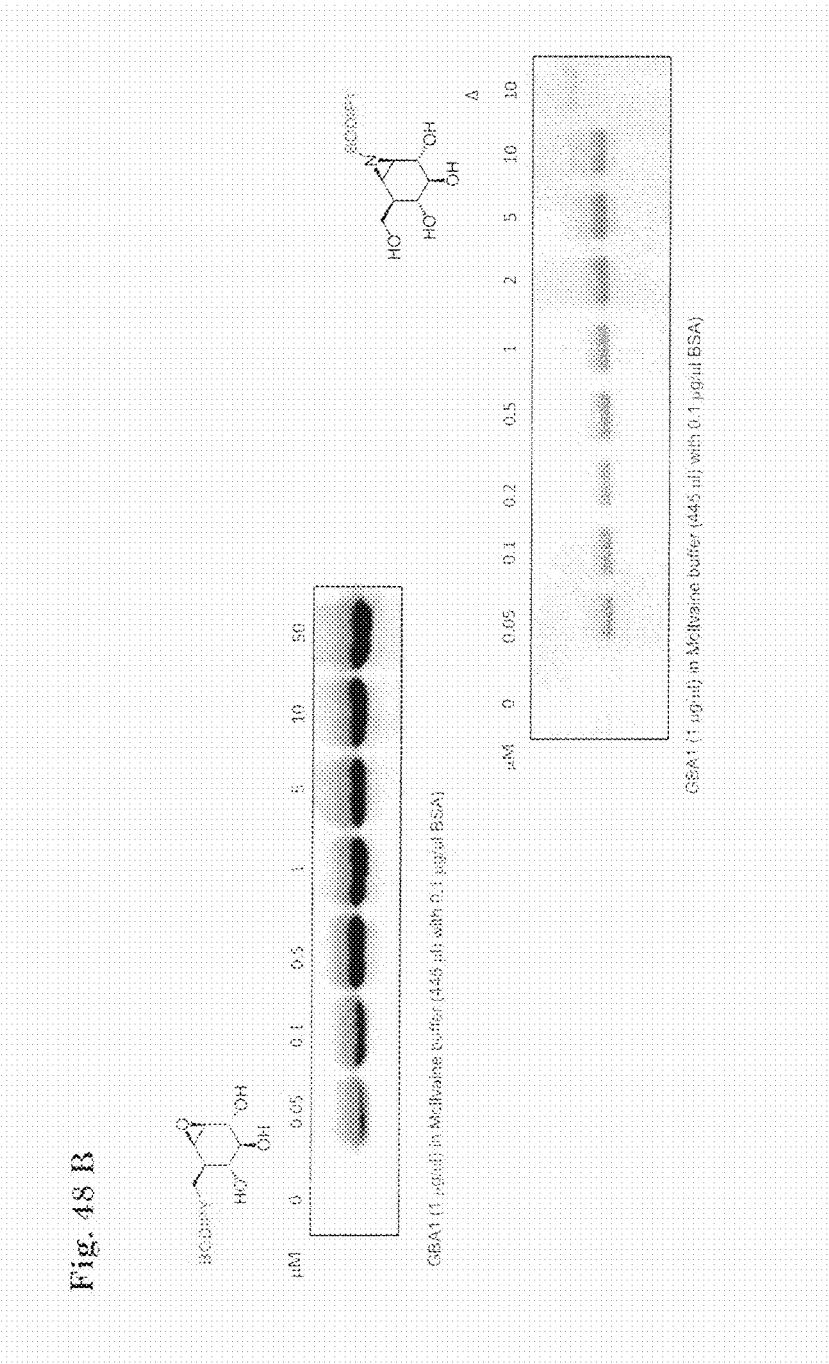

FIG. 48 (A) IC$_{50}$ values of the indicated compounds (the left most compound is Fluorophore 1-cyclophellitol and the right most is compound MDW1044) on GBA1 and ABG (almond beta glucosidase). (B) Left panel fluorescence detected with a fixed amount of GBA1 and increasing amounts of Fluorophore 1-cyclophellitol. Right panel, the same but now for compound MDW1044. (C) The same as panel B but now for ABG (almond beta glucosidase instead of GBA1).

Figure 49:
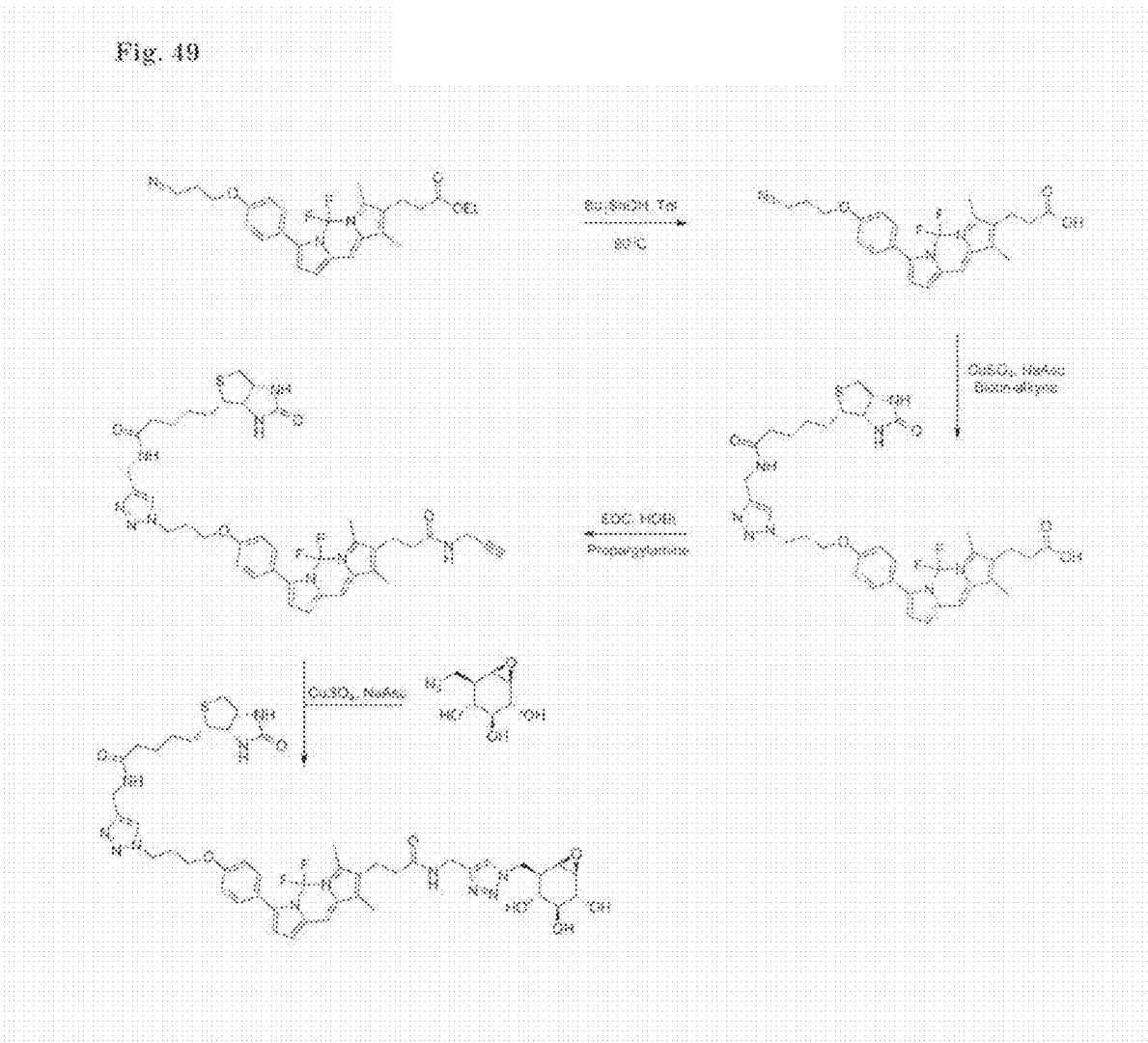

FIG. 49 Synthese of a Fluorophore 1-cyclophellitol with linked thereto a biotin-moiety. The compound can be used in combined detection and pull-down experiments with streptavidin. The final compound is compound MDW971.

Figure 50:
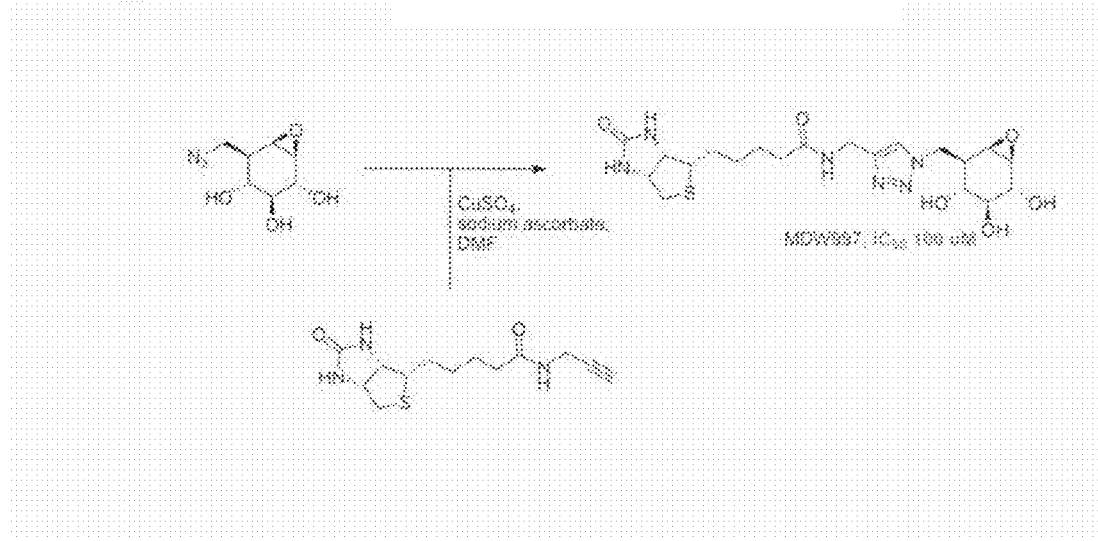

FIG. 50 Synthesis of compound MDW997.

FIG. 51 Synthesis of an inhibody green variant with pH-sensitive fluorescence. The compound exhibits enhanced fluorescence at lower pH values.

Figure 52:
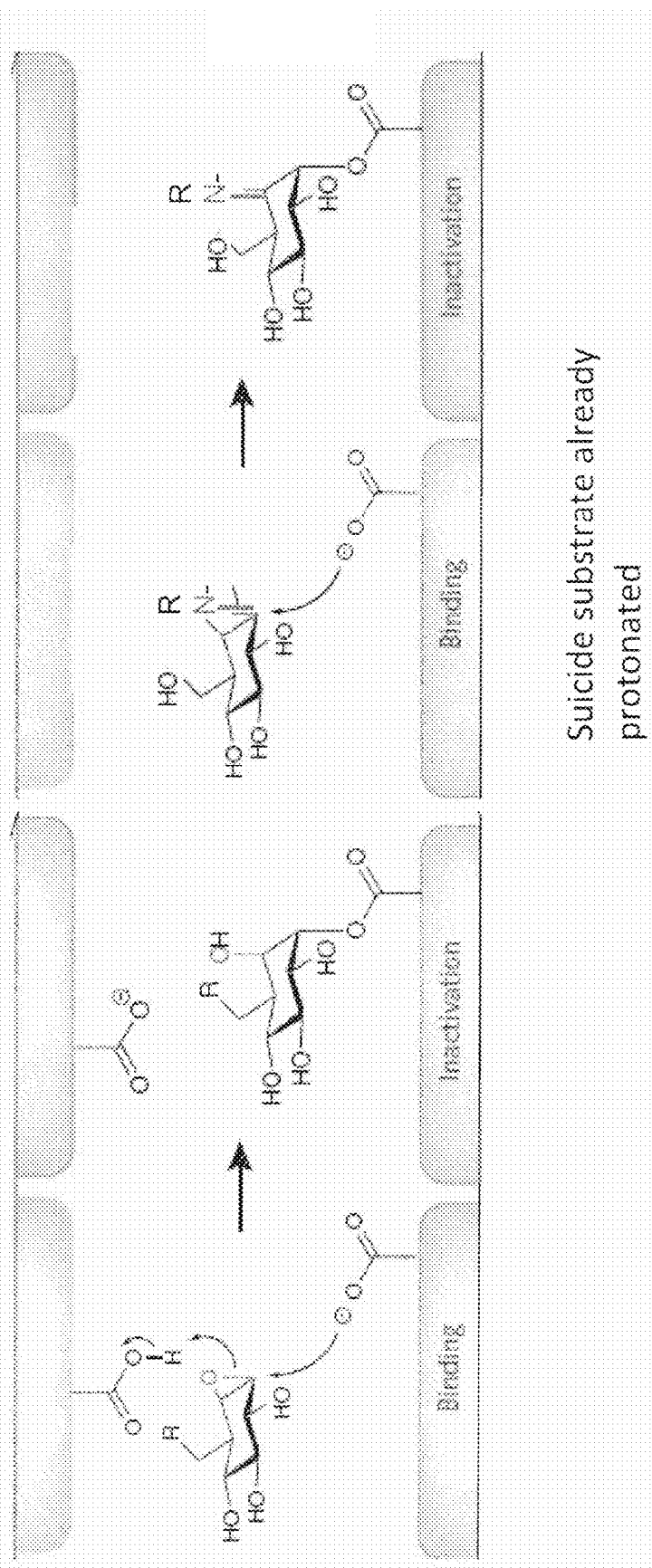

FIG. 52 Schematic representation of the reaction scheme of an inhibody and of a so-called anybody comprising a fluorophore group linked to the N of the azarine group that replaces the epoxide group in cyclophellitol. One explanation for the surprising pH-insensitivity of the suicide reaction is that the N-atom in this group is already protonated and thus at least partially independent on the presence of a proton on the proton donation carboxyl in the reactive site of the enzyme.

FIG. 53 COS cell lysate labelled with an inhibody (Fluorophore 2-cyclophellitol) or compound MDW1044. Top panel shows the relative labelling at different pH values for the respective compounds. The lower panels show the gels on which the results of the top panel are based.

Figure 54:
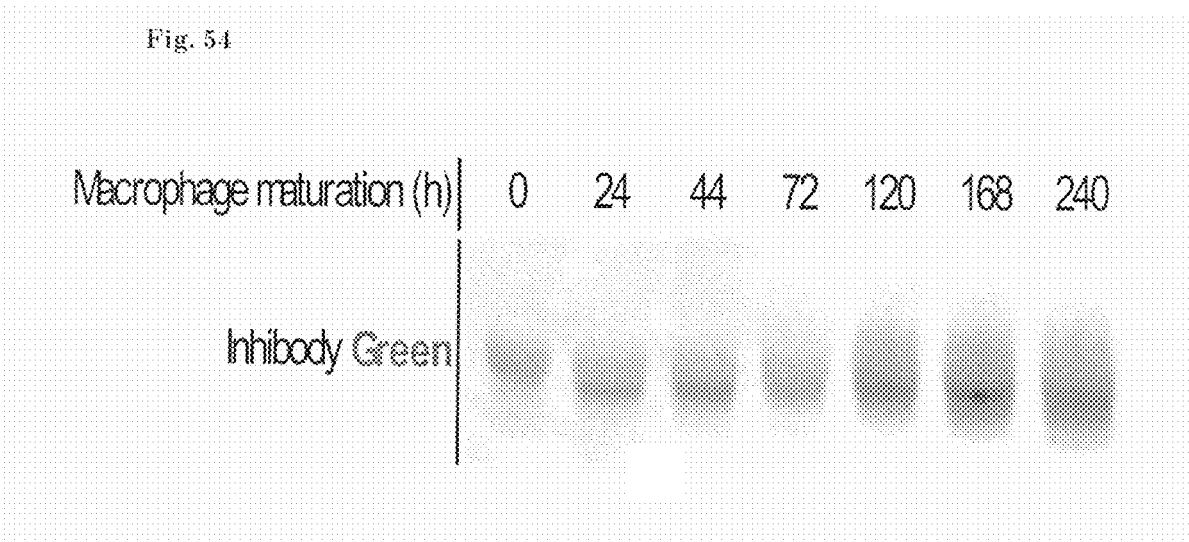

FIG. 54 In situ labelling of monoctes→macrophages

Peripheral blood monocytes cultured with human serum.

Cells were labeled at indicated time points for 2 h with excess Inhibody Green and next harvested. Analysis by SDS-PAGE and fluorescence scan.

Figure 55:
Figure 59:
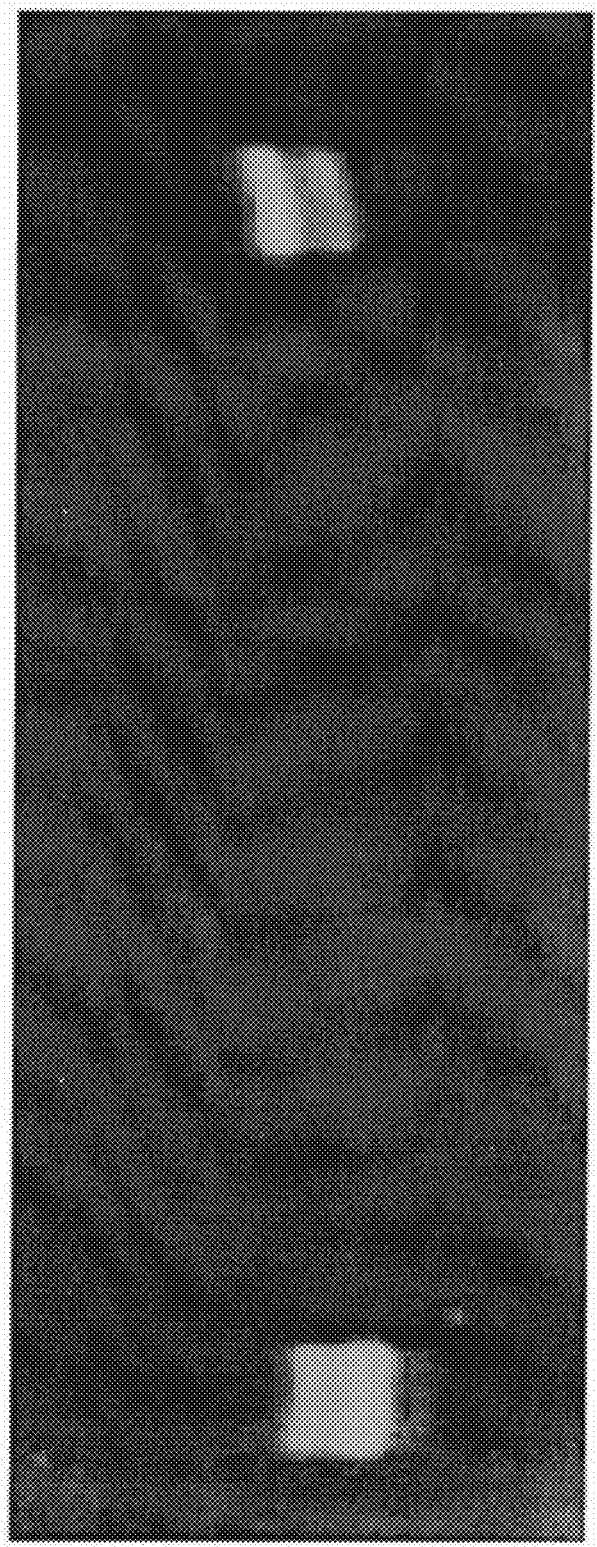

FIG. 55 InhibodyGreen and Red compete equally for binding to GBA. Cerezyme incubated with different ratio's of two Inhibodies SDS-PAGE→Fluorescence scanning FIG. 59 Therapeutic enzymes: Velaglucerase (Vpriv) vs Cerezyme.

Figure 60:
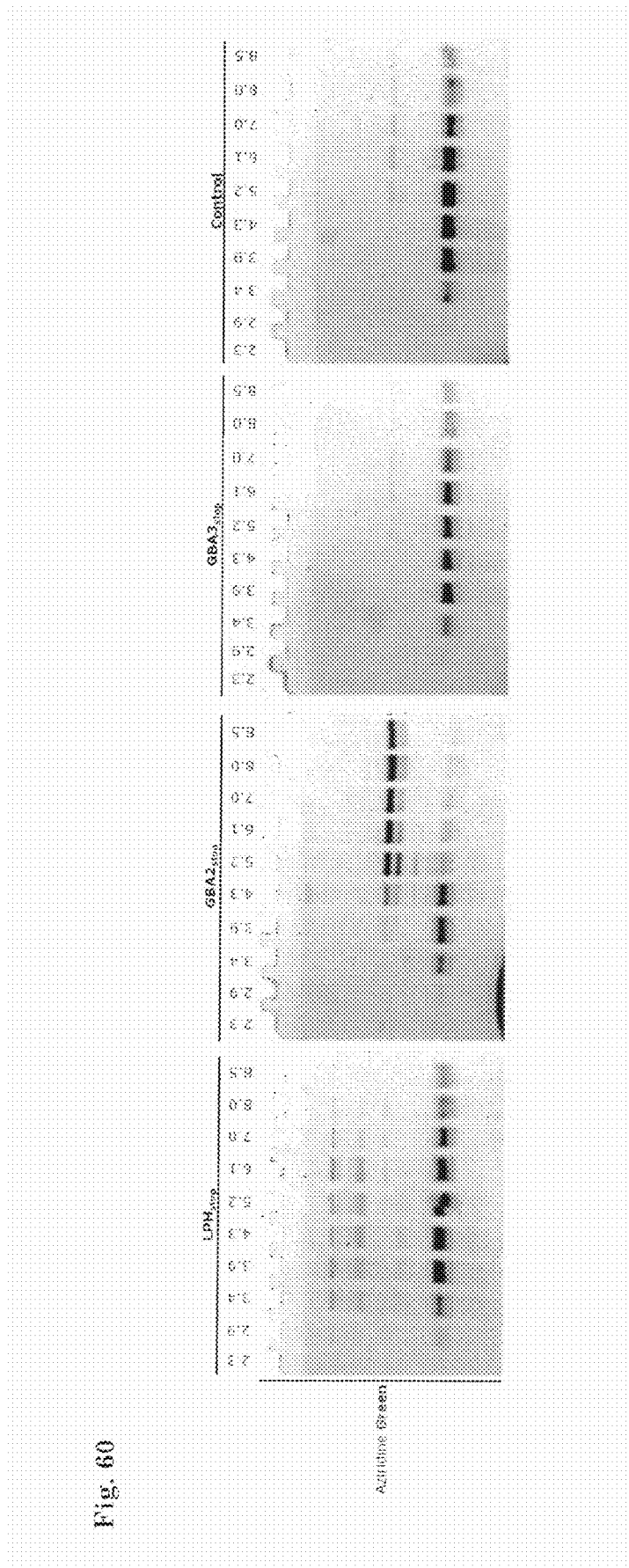

FIG. 60 AnybodyGreen: labelling multiple beta-glucosidases

The following examples represent specific embodiments, which do not limit the present invention to the examples. All numbers in brackets refer to scheme 1.

Example 1

Synthesis of Azido-Cyclophellitol

For producing azido-cyclophellitol connected to a fluorophore or biotine, the epoxide of cyclophellitol (2) is protonated in the active site by a carboxylic residue. Subsequent ring-opening by the nucleophilic residue in catalytic side results in an inhibitor-enzyme. In contrast to the fluorinated glycosides, the glycosyl epoxides (2 and 3 in scheme 1) lack an endo-cyclic oxygen and therefore form highly stable adducts making them good leads for ABPs. Based on the glucosidase inhibitor cyclophellitol (2) and its synthetic diastereomer epi-cyclophellitol (4), a new set of activity based probes was designed, which are applied as glucosidase labels. Modification of the C6-position of cyclophellitol (2) and epi-cyclophellitol (4) with an azide allows visualization of inhibitor-enzyme adducts by Staudinger-Bertozzi ligation or Cu'-catalyzed click reaction. To this end, azido-cyclophellitol (5) and azido-epicyclophellitol (6) were synthesized as depicted in scheme 1.

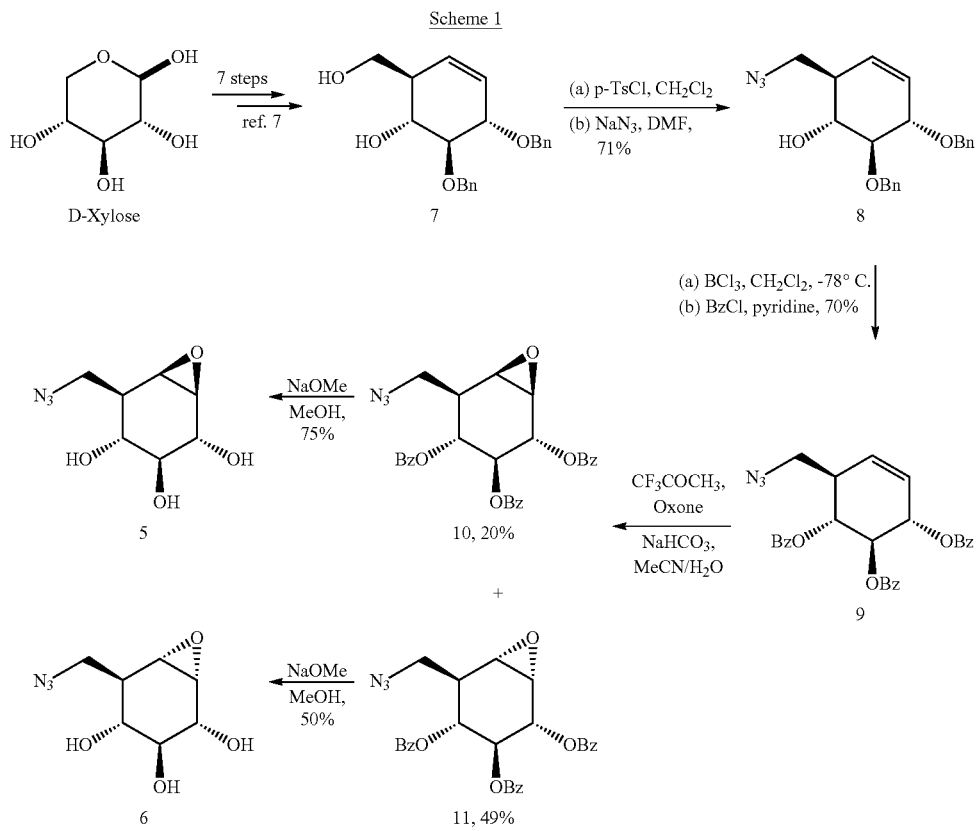

Scheme 1

Figure 56:
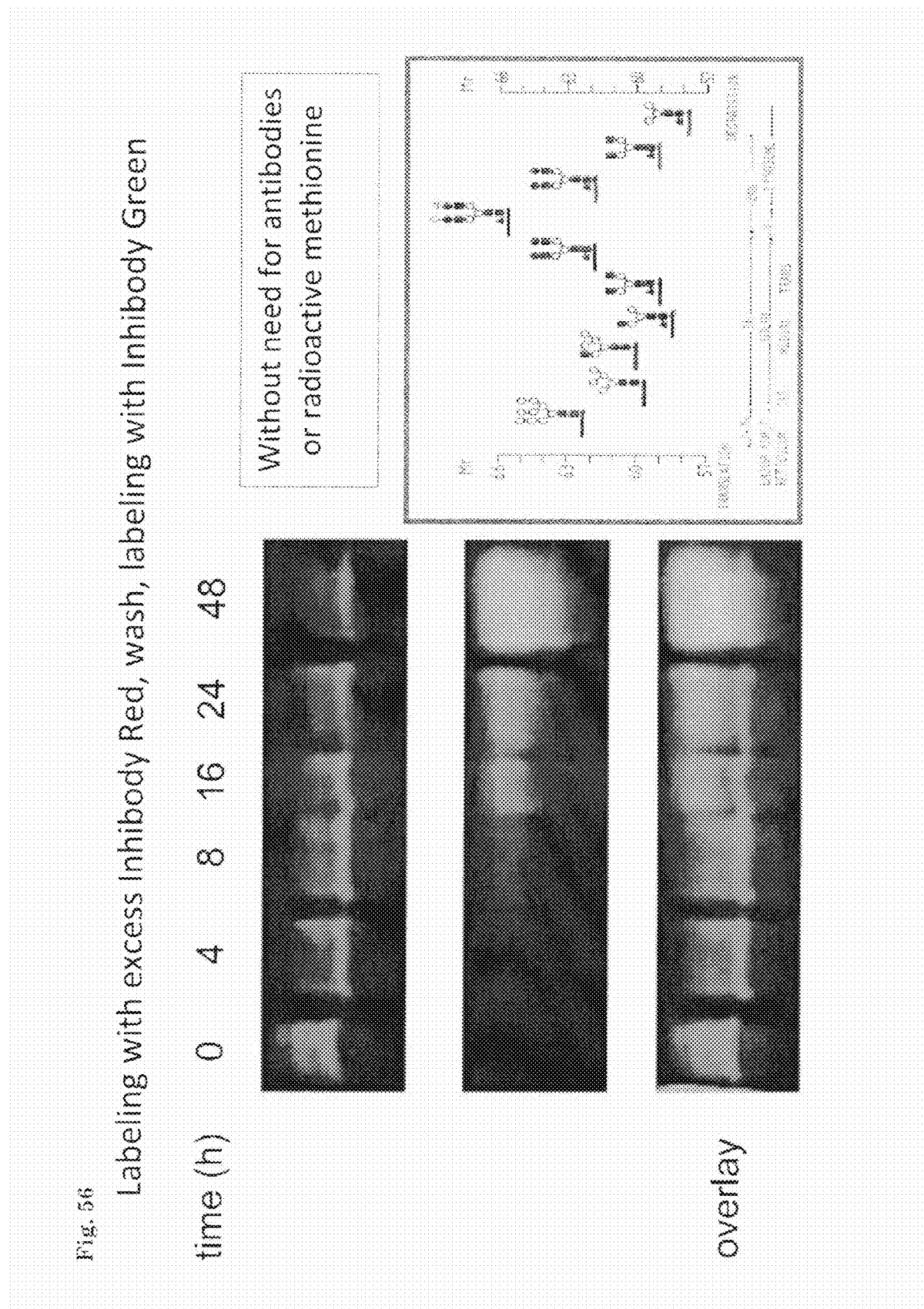
Figure 57:
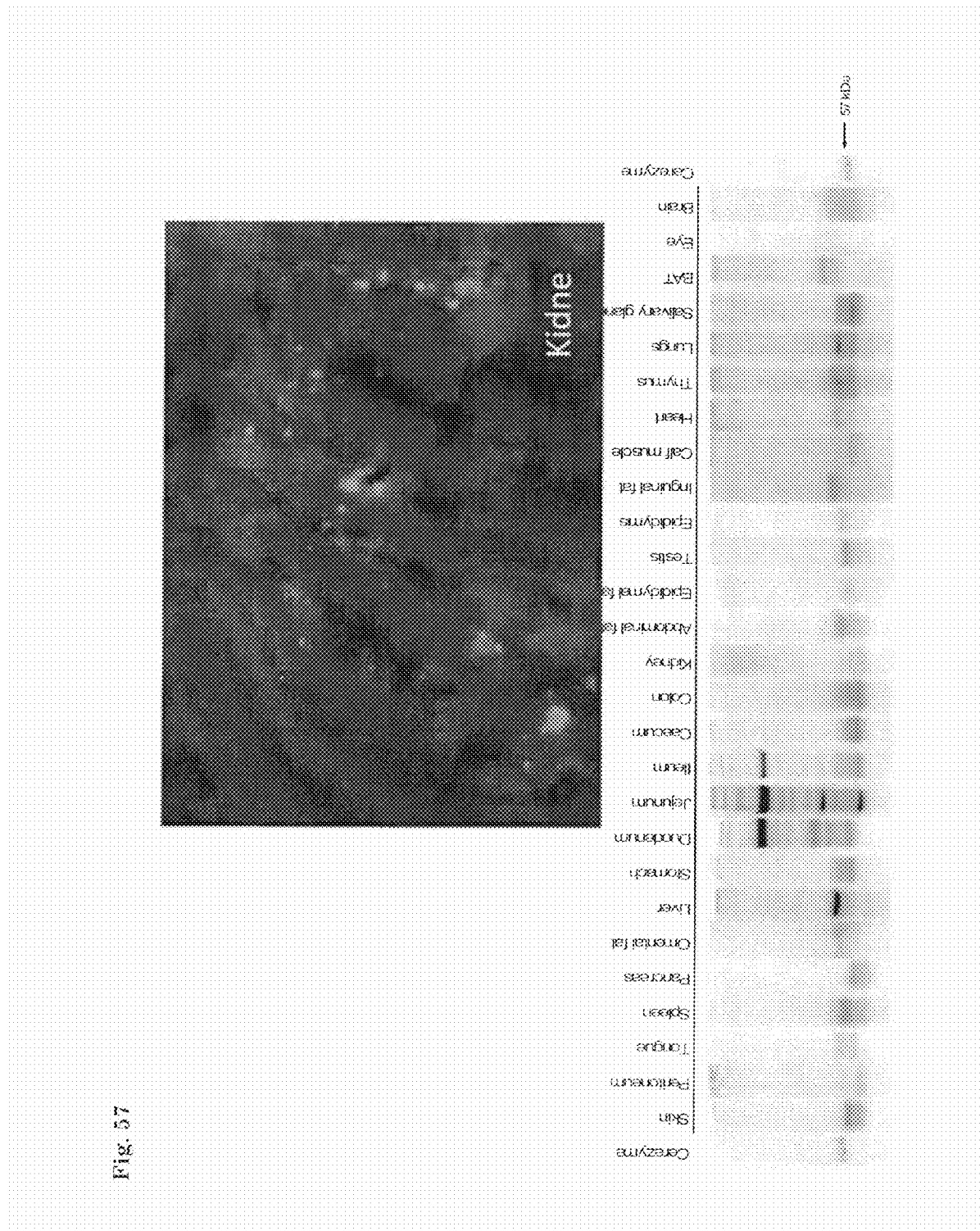
Figure 58:
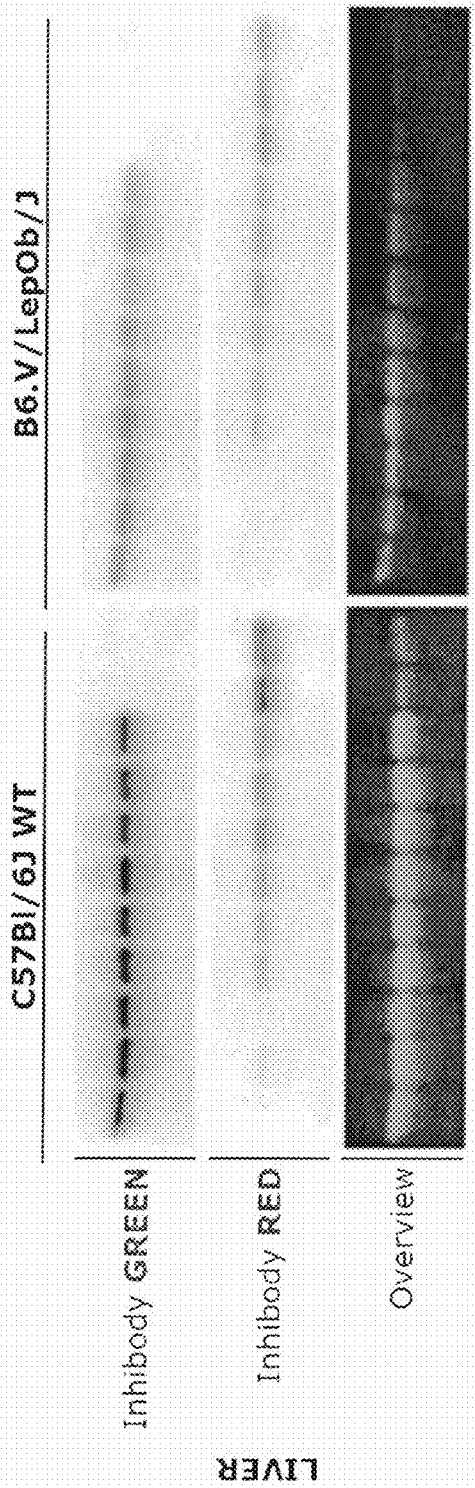

FIG. 56 Pulse-chase experiment in fibroblasts FIG. 57 In situ inhibody labelling of whole animal FIG. 58 Pulse-chase experiment in mouse.

The core carbocycle (7) was synthesized in 7 steps from D-xylose as described by Madsen and coworkers. Selective tosylation of the primary alcohol in (7) by treatment withp-toluenesulfonyl chloride in $CH_2Cl_2$ followed by substitution of the tosylate with sodium azide afforded azido alcohol (8) in 72%. It is important to note that purification of the tosyl-intermediate by silica gel column prior to azidation resulted in a dramatic drop in the yield (42%) Epoxidation of (8) with m-chloroperbenzoic acid (m-CPBA) followed by deprotection with boron trichloride was unsuccessful. Therefore, the benzyl groups in (8) were removed under the agency of $BCl_3$ prior to epoxidation. The resulting free hydroxyls were protected as the corresponding benzoyl protective groups using benzoyl chloride in pyridine. Epoxidation of cyclohexene (9) using in situally formed trifluoro dimethyldioxirane gave epoxides (10) and (11) as a separable mixture. Deprotection with sodium methoxide in methanol gave azidocyclophellitol (5) and epi-azidocyclophellitol (6).

Example 2

Deficiency of glucocerebrosidase (GBA) underlies Gaucher disease, a common lysosomal storage disorder. Carriership for Gaucher disease has recently been identified as major risk for parkinsonism. Presently, no method exists to visualize active GBA molecules in situ. We here report the design, synthesis and application of two fluorescent activity-based probes allowing highly specific labeling of active GBA molecules in vitro and in cultured cells and mice in vivo. Detection of in vitro labeled recombinant GBA on slab gels after electrophoresis is in the low attomolar range. Using cell or tissue lysates, we obtained exclusive labeling of GBA molecules. We present evidence from fluorescence-activated cell sorting analysis, fluorescence microscopy and pulse-chase experiments of highly efficient labeling of GBA molecules in intact cells as well as tissues of mice. In addition, we illustrate the use of the fluorescent probes to study inhibitors and tentative chaperones in living cells.

The lysosomal hydrolase GBA hydrolyzes glucosylceramide[1,2]. This ubiquitously expressed enzyme is initially synthesized as a 519-residue protein that cotranslationally acquires four N-linked glycans. After the removal of its signal peptide, GBA undergoes no further post-translational proteolytic modification and does not acquire mannose-6-phosphate moieties in the Golgi apparatus. The expression of disease in individuals with a defective GBA is remarkably heterogeneous. Substantial deficiency results in Gaucher disease, and recently carriership has been recognized as major risk for parkinsonism[2,3]. The manifestation of Gaucher disease is highly variable, ranging from the common non-neuronopathic (type 1) variant to more severe manifestations with lethal neurological complications (type 2 and 3 variants) and extreme cases with abnormalities in skin permeability (so-called collodion babies)[2]. The marked phenotypic heterogeneity is only partly explained by differences in underlying mutations in the GBA gene. The heteroallelic presence of N370S GBA, the most frequent mutation in Caucasian individuals, protects against a neuronopathic manifestation, whereas homozygosity for L444P GBA is associated with severe neurological symptoms[2]. Several studies have indicated that the relationship between GBA genotype and Gaucher phenotype is not very strict[4]. Even phenotypic heterogeneity among identical twins has been reported, suggesting that additional factors influence the in situ residual activity of GBA[5].

Two treatments for Gaucher disease presently exist: enzyme replacement therapy and substrate reduction therapy. Enzyme replacement therapy is based on chronic intravenous administration of recombinant GBA (imiglucerase; trade name: Cerezyme)[6,7]. Substrate reduction therapy is based on chronic oral administration of N-butyldeoxynojirimycin, an inhibitor of the enzyme glucosylceramide synthase, which catalyzes the formation of glucosylceramide[8,9]. More recently, an alternative approach has received considerable attention, so-called chaperone therapy. Common in Gaucher patients are mutant forms of GBA that show impaired folding and retention in the endoplasmic reticulum, ultimately resulting in elimination via the ubiquitin-proteasome system, a process known as ER-associated degradation (ERAD)[10-15]. Studies have investigated small compounds, designated 'chemical chaperones', that are able to increase the amount of GBA by stabilizing and/or promoting folding of the enzyme. One extensively studied example is isofagomine (1), which is a potent competitive inhibitor interacting with the catalytic pocket[16-20]. Beneficial effects on the amount and lysosomal localization of mutant GBA forms in cultured cells have been reported for isofagomine, but the assays used to demonstrate increased degradative capacity have been quite artificial: cells are exposed to high concentrations of fluorogenic substrate at acidic pH (see, for example, ref. 17). It is not likely that exposing cells to low pH and millimolar concentrations of 4-methylumbelliferyl β-D-glucopyranoside for a prolonged period reflects faithfully the in situ ability of the enzyme to degrade glucosylceramide. Pharmacologic chaperones like isofagomine will only exert a positive clinical effect at a particular dose range: their concentration should be sufficiently high to promote folding of the enzyme in the endoplasmic reticulum to increase transport to lysosomes, whereas the concentration in lysosomes should also be sufficiently low to prevent marked inhibition of catalytic activity. The present lack of a suitable method for specific visualization of active GBA molecules is a major limitation in research on Gaucher disease and parkinsonism, as well as the development of new therapies. For this reason, we embarked on the development of such a method using activity-based labeling. The catalytic mechanism of GBA, a retaining glucosidase, has been elucidated in detail[21,22]. Briefly, unprotonated Glu340 in GBA performs the initial nucleophilic attack on the substrate, forming a covalently linked enzyme-substrate intermediate.

Epoxides like conduritol B epoxide (2, CBE) and cyclophellitol (3) (FIG. 23) form first a noncovalent inhibitor-enzyme complex that then reacts with the Glu340 carboxylate to form a covalent bond, thus acting as irreversible inhibitors. Cyclophellitol resembles more closely the structure of glucoside substrates and is the more potent irreversible inhibitor of the two[23]. We capitalized on this by grafting boron dipyrromethene (BODIPY) fluorophores on to the cyclophellitol core (FIG. 23). We here demonstrate highly efficient labeling of GBA in situ by these probes and reveal their use in monitoring GBA activity in Gaucher fibroblasts.

Results

Compounds are referred to herein below by their chemical name, an arbitrary name and/or by an arbitrary number. The chemical structures that are associated with these names and number are depicted in FIG. 22.

Design and Synthesis of Activity-Based Probes

We synthesized cyclophellitol (ref. 24) and 8-deoxy-8-azidocyclophellitol (4, KY170) (FIG. 23; for synthesis see Example 3 results) and tested their inhibitory properties toward recombinant GBA (Genzyme). Cyclophellitol and its azido analog KY170 were found to be far more potent inhibitors of GBA than CBE. Click ligating BODIPY moieties to KY170 gave fluorescent inhibitors MDW933 (5) and MDW941 (6) (FIG. 23; for synthesis, see Example 3 results). Examination of the inhibitory properties revealed that MDW933 and MDW941 were comparably potent as irreversible inhibitors, being markedly superior to CBE and even surpassing cyclophellitol and KY170. The apparent half-maximal inhibitory concentration ($IC_{50}$) values of both fluorescent compounds (MDW933: $IC_{50}$=1.24±0.04 nM; MDW941: $IC_{50}$=1.94±0.08 nM) were very similar, being about 100- and 1.000-fold lower than those of cyclophellitol and KY170 ($IC_{50}$=0.15±0.009 μM and 0.12±0.004 μM, respectively) and CBE ($IC_{50}$=9.49±0.042 μM). We determined next the inhibition constants—the $K_i$ (the equilibrium constant for initial binding), the rate constant ($k_i$) and the relative rate constant $k_i/K_i$—for CBE, cyclophellitol, KY170, MDW933 and MDW941 using a continuous substrate release assay (see FIG. 28 for progress curves). A general trend that we observed for the equilibrium constant for initial binding was that increased hydrophobicity resulted in decreased $K_i$ values (Table 3). Comparison of relative rate constants demonstrated that the fluorescent probes inhibited GBA 22-, 34- and 4.300-fold better than KY170, cyclophellitol and CBE.

TABLE 3

Binding constants of the inhibitors

| | $k_i$ (min$^{-1}$) | $K_i$ (μM) | $k_i/K_i$ (μM$^{-1}$ min$^{-1}$) |
|---|---|---|---|
| CBE 2 | 0.217 ± 0.026 | 53 ± 10.8 | 0.004 |
| Cyclophellitol 3 | 0.078 ± 0.010 | 0.152 ± 0.026 | 0.514 |
| KY170 4 | 0.035 ± 0.003 | 0.044 ± 0.007 | 0.794 |
| MDW933 5 | 0.127 ± 0.024 | 0.007 ± 0.002 | 17.76 |
| MDW941 6 | 0.208 ± 0.063 | 0.008 ± 0.003 | 25.10 |

$K_i$ and $k_i$ values were calculated as described in the example 3 Results and example 3 Methods and reported with s.e.m.

The affinity of MDW933 and MDW941 for GBA was unexpectedly high. For a better understanding of this finding, we performed molecular docking analysis using the GBA crystal structure (PDB: 2V3E)[25]. The docking model revealed that at minimum free energy of the simulated enzyme-ligand complex, both fluorescent probes efficiently bound to the GBA active site. Tight fitting of the BODIPY moiety in a hydrophobic pocket near the position in the active site where the 6'-hydroxyl of its natural substrate would reside appears to contribute to the binding. In this orientation, the epoxide was positioned 3 Å away from Glu340, close enough to allow nucleophilic addition of the Glu340 carboxylate (FIG. 29). The calculations yielded minimum free energy values that were significantly lower for the hydrophobic fluorescent probes MDW933 and MDW941 (−8.1 kcal mol$^{-1}$ and −8.4 kcal mol$^{-1}$) than for KY170 (−5.2 kcal mol$^{-1}$), explaining their superior inhibitory properties. Notably, when we compared the crystal structure of GBA (PDB: 2VT0) with the modeled enzyme structure (PDB: 2V3E) with CBE or MDW933 (FIG. 29), the cyclitol moiety did not completely overlap with that of CBE covalently bound to 2VT0. The intrinsic differences in structure coordinates between the crystal structures, as well as the comparison of the positioning of CBE and MDW933 before the prenucleophilic attack with the already covalently bound state of CBE, could have caused this discrepancy. The presence of the latter was likely enough to physically alter the local protein structure.

In Vitro Labeling of GBA with the Fluorescent ABPs

To examine labeling of recombinant GBA by MDW933 and MDW941, we incubated the enzyme for 30 min at 37° C. with mixtures of both probes at pH 5.2, with 0.2% (w/v) taurocholate and 0.1% (v/v) Triton X-100, an optimal condition for enzymatic activity and activity-based labeling. After the incubation, we resolved the protein preparations with SDS-PAGE and analyzed the labeled proteins by fluorescence scanning of the slab gel on a Typhoon Variable Mode Imager (FIG. 24a). Labeled recombinant GBA migrated at the expected mass of 57 kDa. At equimolar concentration of MDW933 and MDW941 (100 nM), both probes bound the enzyme equally well. Thus, labeling of GBA with both probes was comparable, as expected given their similar inhibition constants. Boiling of the samples before electrophoresis had no impact on the detection of the fluorescently labeled protein on the slab gel, indicating that the probe was firmly attached. The presence of reducing agent also did not affect the covalent binding of the probes. We determined the sensitivity of detection of labeled GBA by incubating 2 pmol GBA with an excess of MDW933 (20 nmol at 1 mM concentration) for 1 h at 37° C. and subsequent titration of the amount applied on the gel (FIG. 24b). We could detect as little as 20 attomol GBA by fluorescence scanning. Next, we incubated equal amounts of GBA (2 pmol) for 30 min with decreasing amounts of MDW933 and applied all protein to a gel. Incubation with as little as 20 attomol of probe resulted in detectable GBA on the slab gel (FIG. 24b). Apparently, nearly all of the probe had been covalently bound to recombinant GBA, consistent with its high affinity for binding. These experiments indicated that ultrasensitive detection of GBA was feasible on slab gels following in vitro labeling with the fluorescent probes 5 and 6.

As a next step, we analyzed the site of binding of the probe on GBA using a competition assay. Prior to labeling with MDW933, we incubated recombinant GBA with 2 mM CBE for 30 min (FIG. 24c). Preincubation with CBE, shown via crystallography to bind Glu340 (ref. 26), blocked labeling completely. Similarly, we also noticed competition with labeling by the competitive inhibitor AMP-DNM (7) (FIG. 24c)[27]. These results from competition experiments indicated that indeed the probe was bound in the catalytic center of GBA. We unambiguously identified the site of binding of KY170 and MDW933 by mass spectrometry. Using tryptic digestion and LC-MS/MS, we detected active site fragments of GBA that showed a shift in mass coinciding with binding of KY170 to Glu340 (FIG. 30). A similar experiment with MDW933 did not render detectable tryptic fragments of interest, most likely because the attachment of the hydrophobic moieties impaired ionization. We circumvented this complication by treating GBA labeled with MDW933 with hydroxylamine before tryptic digestion. This released the probe from GBA and concomitantly converted the modified residue into a hydroxamic acid. The outcome of this experiment demonstrated that MDW933 also bound covalently to Glu340 (FIG. 30).

Enzymatically active GBA molecules are a prerequisite for labeling with the probe, as demonstrated by the lack of labeling of GBA that had been denatured by boiling (FIG. 24c). The same conclusion could be drawn from the pH dependence of irreversible inhibition of GBA by the fluorescent probes. It exactly coincided with the pH profile of enzymatic activity toward 4-methylumbelliferyl β-D-glucopyranoside (FIG. 24d).

Labeling of GBA in Cell and Tissue Extracts

To determine the labeling specificity of both fluorescent probes, we incubated homogenates of cultured cells and mouse tissues with 100 nM green fluorescent MDW933 for 30 min at 37° C. and analyzed the preparation with SDS-PAGE. In the case of homogenates of cultured RAW cells, fluorescence scanning showed exclusive labeling of GBA by MDW933. The various GBA forms, with molecular mass ranging 58-66 kDa owing to glycan differences, were visualized (FIG. 24e). With several other cell types such as HepG2 cells, COS cells and human fibroblasts, we obtained similar results (FIG. 31). Furthermore, red fluorescent MDW941 also labeled GBA selectively in RAW cells (FIG. 31). It was striking that incubation of cell lysates with the probes did not result in fluorescent labeling of other cellular proteins. Furthermore, we observed very similar results—that is, highly specific labeling of GBA—using lysates of mouse tissues (FIG. 24f). Homogenates of mouse intestine were the only exception, most likely owing to labeling of high-molecular weight lactase and fragments thereof. Lactase (lactase-phloridzin hydrolase: LPH) is known to covalently bind CBE[28], and we therefore reasoned that MDW933 may also irreversibly inhibit lactase activity. This was indeed the case: incubation for 30 min with 1 mM of MDW933 resulted in ~90% inhibition of lactase activity. Next, we demonstrated that a high concentration of lactose (250 mM) reduced markedly (>90%) the labeling of the high-molecular weight protein in the intestinal fraction while leaving labeling of GBA practically unaltered (FIG. 32).

In Situ Labeling of GBA in Cultured Cells

We investigated whether labeling of GBA in intact cells was also feasible. For this purpose we added MDW933 or MDW941 to the culture medium at a concentration of 5 nM. At different time points, we harvested the cells and determined the GBA activity in the cell homogenates with artificial substrate (FIG. 25a). Even in intact cells, GBA was inactivated by both probes. Apparently, the more hydrophobic MDW941 could more easily reach intracellular GBA. It is presently not clear how exactly the probes enter cellular compartments. It is unlikely that uptake occurred only by endocytosis, given the fast speed of labeling and its occurrence at low temperature at which endocytosis is blocked (FIG. 33). Direct uptake of the probes, either by diffusion of the amphiphilic structures or by facilitation by transporters, seems most likely.

We studied in situ labeling of GBA in cells using fluorescence-activated cell sorting (FACS) analysis. We first preincubated cells in the absence or presence of CBE and subsequently incubated the cells with a subsaturating or an excess amount of the green fluorescent probe 5. FACS analysis revealed dose-dependent fluorescent labeling of cells and no labeling above background in CBE pretreated cells (FIG. 25b). These positive results prompted us to analyze labeling of the cells with fluorescence microscopy (FIG. 25c-f). For this purpose, we cultured fibroblasts for 2 h with 5 nM MDW941. We also detected GBA protein by indirect immunofluorescence using the specific anti-GBA monoclonal antibody 8E4 (ref. 29). Using multispectral image analysis, we could specifically distinguish the respective fluorescent emission spectra (FIG. 25d-e) from autofluorescent background (FIG. 25c). The intracellular pattern of labeling with MDW941 showed an almost complete overlap with the detection of GBA by monoclonal antibody 8E4 using this method (FIG. 25f). As probes with a hydrophobic BODIPY moiety might nonspecifically be retained in membranes, in particular the plasma membrane, we studied this possibility more closely. First, we cultured fibroblasts obtained from a Gaucher patient homozygous for the RecNCI GBA mutation (a mutation resulting in premature degradation of GBA by the proteasome) with MDW941. In contrast to control fibroblasts, the patient's cells did not show labeling in the lysosomal compartment by MDW941 but only in the perinuclear area (FIG. 34). As expected, immunofluorescence using monoclonal 8E4 showed a lysosomal staining pattern for GBA in the control cells whereas RecNCI cells revealed staining for GBA in the cytosol, most likely because of high levels of ERAD and proteasomal degradation in these cells. Next, we cultured wild-type fibroblasts for 16 h in presence of 3 mM CBE to irreversibly inhibit GBA molecules and block labeling. Subsequent culturing of the cells for 2 h with 5 nM MDW941, again in presence of CBE, rendered perinuclear red BODIPY fluorescence that was distinct from the autofluorescence. Control fibroblasts cultured with MDW941 in the absence of CBE revealed labeling in the lysosomal compartment largely overlapping with the autofluorescence (FIG. 35). Finally, we synthesized MDW1064 (8) and MDW1065 (9) as nonreactive analogs of probes MDW933 and MDW941 (see Example 3 Methods for structure and synthesis). These control probes did inhibit GBA in vitro with $IC^{50}$ values of 41 and 95 µM, respectively. However, inhibition is presumably reversible. After culturing of fibroblasts for 2 h with 5 nM control, MDW1065 resulted in hardly any detectable labeling. In the presence of CBE, MDW1065 only weakly labeled the fibroblasts, in a pattern that may suggest interaction with the cell membrane (FIG. 35).

To show the versatility of the probes, we performed pulse-chase experiments using cultured cells. For this purpose, we incubated fibroblasts overnight with 10 nM red fluorescent MDW941. Subsequently, we treated the cells with 10 nM of the green fluorescent probe, harvested them at different time points (0-48 h) and subjected aliquots of cell homogenates to gel electrophoresis (see FIG. 25g for the lifecycle of GBA as visualized in this manner). It should be noted that GBA pulse labeled with the red fluorescent MDW941 disappeared gradually from the cells with an estimated half-life of about 30 h. The obtained half-life was consistent with the half-life determined previously using conventional pulse-chase labeling with radioactive methioninem. During the chase, GBA was increasingly labeled with MDW933, coinciding with formation of new GBA molecules (FIG. 25g).

We next studied the labeling of GBA by MDW941 in intact fibroblasts using time-lapse microscopy. Fibroblasts treated with the probe showed very rapid fluorescent labeling of lysosome-like structures (data not shown). With 5 nM MDW941, labeling reached a maximum within 15 min. Even after 100 h of exposure to the compound, cells did not show any signs of apoptosis or toxicity. Finally, we examined the possibility of labeling GBA in mice by intravenously administering 0.1 nmol green fluorescent MDW933 dissolved in phosphate-buffered saline to adult mice. As a control, matched mice received the buffer solution intravenously. After 2 h, we killed the animals, prepared tissue extracts, labeled them with excess red fluorescent MDW941 to visualize unlabeled GBA and subjected them to SDS-PAGE (FIG. 26 shows the outcome of a typical experiment). In most tissues—here we show lung and liver—MDW933 already labeled a considerable proportion of GBA (FIG. 26a). Consistently, in such tissues the probe also irreversibly inhibited a large proportion of GBA in the living mouse (see FIG. 26b). An exception in this respect was the brain (FIG. 26a), in which MDW933 apparently labeled almost no GBA in vivo and GBA was not inactivated. As observed earlier, intestinal fractions showed labeling of proteins of multiple molecular masses (FIG. 26a). In addition to GBA, MDW933 clearly labeled other proteins that occur in the intestine in the mouse.

Analysis of Gaucher Materials

We investigated labeling of mutant GBA in fibroblasts from a normal individual and from Gaucher donors (a N370S GBA homozygote, a L444P homozygote and a RecNCI homozygote manifesting as collodion Gaucher and almost entirely lacking GBA protein) by treating cell lysates with MDW933 (10 nM) for 1 h and subjecting these to SDS-PAGE. A comparison of cells from a normal subject and from a Gaucher donor homozygous for L444P GBA revealed that the amount of L444P GBA was markedly lower in the Gaucher donor (FIG. 27a). It is indeed known that L444P GBA undergoes largely premature degradation by ERAD as a result of impaired folding[11]. This phenomenon is far less striking in the case of N370S GBA[10]. Cells from a Gaucher donor homozygous for N370S GBA also showed reduced labeling of GBA but to a lesser extent than cells from a L444P homozygote (FIG. 27a). As expected, cells from the RecNCI collodion Gaucher did not show any labeled GBA (FIG. 27a). We obtained similar results by analysis of the fibroblast extracts using western blotting and the anti-human GBA antibody 8E4, although the detection limit of this method was far inferior (FIG. 27a).

It has been noted that the irreversible inhibition by CBE of N370S GBA is less strong than its inhibition of wild-type GBA[20,30]. We therefore determined inactivation curves of GBA activity in cells of a normal subject and a N370S GBA homozygote (FIG. 27b). Notably, MDW933 inactivated GBA activity in wild-type and N370S GBA cells quite similarly. Analysis of GBA in spleen from a Gaucher patient with solely N370S GBA resulted in a similar picture. Labeling of spleen lysates with variable concentrations of MDW933 again resulted in a lower amount of detected GBA protein in that tissue (FIG. 36).

Impact of Isofagomine on N370S GBA in Cultured Fibroblasts

It has been reported that for cells from N370S GBA homozygotes, prolonged incubation with isofagomine yields an increase in GBA activity[31]. The interaction of isofagomine with the catalytic pocket has been intensely studied, including at the level of crystals[21]. We therefore examined whether incubation of N370S GBA homozygous fibroblasts with isofagomine increased the amount of GBA that can be labeled with fluorescent probes. We cultured cells for 7 d with different concentrations of isofagomine (0, 10, 30 and 300 nM) and subsequently incubated them for 2 h with or without excess MDW941 in the presence of the original concentration of isofagomine. Determination of the activity of GBA in homogenates of cells not treated with MDW941 using 4-methylumbelliferyl β-D-glucopyranoside as substrate revealed a modest isofagomine dose-dependent increase in enzyme activity (seen in FIG. 27c). Aliquots from the homogenates of cells labeled with MDW941 were subjected to gel electrophoresis, and the detected fluorescent GBA was quantified. Again we noted a modest dose-dependent increase (FIG. 27d), although less marked than the increase in in vitro enzyme activity in the homogenates. This discrepancy might be due to concomitant in situ stabilization of GBA by isofagomine in combination with competitive inhibition of enzymatic activity. We therefore investigated the effect of isofagomine on GBA activity in the intact cell using 5'-pentafluorobenzoylaminofluorescein-di-B-D-glucoside (FDG) as a substrate. Incubation of fibroblasts with various concentrations of isofagomine for 20 min, subsequent addition of FDG to the medium and quantification of the hydrolysis of FDG by FACS allowed determination of the $IC_{50}$ value of isofagomine in intact cells[32]. The $IC_{50}$ of isofagomine for hydrolysis of FDG was about 1 μM (FIG. 28e). Apparently, isofagomine at concentrations >1 mM completely inhibited activity of GBA in intact cells. We studied the reversibility of isofagomine competition for the fluorescent active site labeling. For this purpose, we preincubated recombinant GBA attached to monoclonal antibody 8E4 immobilized to Sepharose beads for 15 mM with increasing concentrations of isofagomine at pH 5.2 in the presence of taurocholate (0.2% w/v) and Triton X-100 (0.1% v/v). Prior to labeling with MDW933 (10 nM for 15 min), we either washed or did not wash the bead suspension with the same buffer. Quantification of the labeled GBA on slab gel indicated that the competition of isofagomine for the active site was fully reversible (FIG. 37).

Discussion

The need for a method allowing visualization of active GBA molecules in situ in living cells is evident. It is of importance to understand better what the precise cell and tissue distribution of active GBA molecules is because this may render a better understanding of the pathogenesis of Gaucher disease. Moreover, demonstration of a true increase in active GBA molecules by tentative chaperones is of interest. At present the detection of GBA still relies on the use of antibodies that do not distinguish between active and inactive GBA molecules and can not label enzyme in intact cells. Our search for a suitable probe for activity-based labeling of GBA in situ has yielded the desired result. As starting point for the development of such a probe, we selected cyclophellitol, a known potent irreversible inhibitor of GBA that forms a covalent adduct. Next we linked, via a spacer, hydrophobic BODIPY moieties to cyclophellitol. Serendipitously, this led to even more potent irreversible inhibitors. Molecular docking analysis suggested that interaction of the hydrophobic BODIPY moiety in MDW933 and MDW941 with a hydrophobic pocket at the surface of GBA guides the epoxide to a position close to Glu340. This effect may plausibly underlie the remarkable avidity of the two fluorescent compounds as activity-based probes. The labeling of GBA with the fluorescent probes MDW933 and MDW941 seemed to proceed exactly via the expected mechanism for cyclophellitol inhibition of a betaglucosidase[33]. We could indeed demonstrate that labeling could be blocked with CBE or KY170 and potent competitive inhibitors such as hydrophobic deoxynojirimycines could compete away labeling. Labeling also required the folded enzyme and occurred proportional to enzymatic activity at different pH.

The affinity of both probes for GBA is in fact quite notable: truly ultrasensitive detection of GBA molecules was obtained. The high affinity of the fluorescent probes for GBA offered the opportunity to label the enzyme very specifically. With cell or tissue lysates, exclusive labeling of GBA molecules was observed following electrophoresis. In the case of homogenates of intestine alone we noticed labeling of other proteins, probably fragments of LPH known to covalently interact with CBE. The highly selective labeling of GBA is notable when taking into account the fact that GBA is a very low-abundance protein and constitutes <$10^{-5}$ of all cellular or tissue protein[29]. Another favorable feature of these probes is their ability to enter various cellular compartments. It will be of interest to determine the precise mechanism(s) more closely, although it is already clear that cellular entry seems not to depend on endocytosis. The entry of the probes into living cells allows their use in FACS analysis, and one can perform pulse-chase experiments in intact cells as we have demonstrated. Time-lapse microscopy confirmed that GBA can be labeled very efficiently in intact fibroblasts. We obtained no indications that fluorescent labeling of GBA was toxic to the cells. Initial experiments also indicated that in mice cellular GBA can be labeled with fluorescent cyclophellitol-based compounds. Notably, the brain showed a different picture. Almost no brain GBA was labeled in mice upon intravenous administration of MDW933. This may suggest that MDW933 does not pass the blood-brain barrier or is actively removed from the brain by some P-glycoprotein. The fluorescence features of the green and red fluorescent probes are intrinsically suboptimal for in situ imaging of labeled GBA in tissues or whole animals. The potential applications for the activity-based fluorescent probes MDW933 and MDW941 are substantial. They offer an alternative to antibodies, which are species-specific and can not reach compartmental GBA in intact cells. Moreover, in contrast to antibodies, our probes uniquely label active GBA molecules. One tentative area of application of the fluorescent probes may be diagnosis of Gaucher disease, in particular the demonstration of low amounts of active GBA molecules in fibroblasts or blood cells of patients. This is helpful, as low amounts of active GBA molecules are usually associated with severe, neuronopathic Gaucher disease. Another area of application for these fluorescent probes may be found in the analysis of compounds for their possible inhibitory or chaperone effects. As we demonstrated, the beneficial effect of isofagomine on N370S GBA in cultured fibroblasts could be confirmed with activity-based labeling. This finding is of importance as it implies that at an optimal concentration of isofagomine, occupation of the catalytic center by the competitive inhibitor is in situ sufficiently low to allow labeling by the fluorescent probe. In other words, at an appropriate concentration isofagomine indeed increases GBA levels and intralysosomal enzymatic capacity. This finding for isofagomine is not entirely unexpected, as it has been proposed that at the low intralysosomal pH isofagomine interacts less well with β-glucosidases than at neutral pH in the endoplasmic reticulum[34]. Our observations render support for the approach of chaperone therapy, although the dosing of drugs in patients to reach optimal (steady-state) concentrations in various tissues may prove to be a major challenge.

Our approach of selective detection of GBA molecules using fluorescently labeled irreversible inhibitors allows unprecedented, ultrasensitive in vivo monitoring of active enzyme molecules. The same approach also applies for other glycosidases. Another option is to use the (fluorescent) probes in living animals. Several approaches are possible. In the first approach the fluorescent probes are used to report on local GBA activity. In the second strategy, recombinant GBA is labeled with the fluorescent probe so that after administration, trafficking of the construct can be monitored in a strategy that is related to another recently reported strategy that uses active site labeling of recombinant and purified GBA with a radiotag[35]. In another approach, probes with infrared fluorescence are used for in vivo imaging. Tissue and organs are more transparent for infra-red light than for visible light. In conclusion, the reported fluorescent activity-based probes offer very versatile research tools to visualize active GBA, ultrasensitively and specifically. This accomplishment is not only relevant for Gaucher disease but also for parkinsonism.

Methods

See Example 3 Methods for the synthesis of the probes, the methods used to determine the binding constants, molecular docking studies, time-lapse microscopy and mass spectrometric analysis of GBA labeled with KY170 and MDW933.

General methods. Chemicals were obtained from Sigma-Aldrich if not otherwise indicated. Recombinant GBA was obtained from Genzyme. Monoclonal anti-human GBA antibody 8E4 was produced from hybridoma cells as described earlier[36]. Gaucher patients were diagnosed on the basis of reduced GBA activity and demonstration of an abnormal genotype[37]. Fibroblasts were obtained with consent from donors. Cell lines were cultured in HAMF12-DMEM medium (Invitrogen) supplied with 10% (v/v) FBS.

Enzyme Activity Assays.

Activity of GBA was measured at 37° C. with 4-methylumbelliferyl β-D-glucopyranoside as substrate as reported previously. To determine the $IC_{50}$ value, the inhibitors were preincubated for 30 min with the enzyme before addition of the substrate mixture. The incubation mixture contained 3 mM fluorogenic substrate, 0.2% (w/v) sodium taurocholate and 0.1% (v/v) Triton X-100 in 150 mM McIlvaine buffer, pH 5.2. After stopping the incubation with excess NaOH-glycine (pH 10.3), we measured fluorescence with a fluorimeter LS 30 (Perkin Elmer) using $\lambda_{ex}$ 366 nm and $\lambda_{em}$ 445 nm. Activity of lactase was quantified by measuring liberated glucose from lactase[38]. In vivo activity of GBA in cells was measured using FDG as substrate and FACS[32].

Gel Electrophoresis and Fluorescence Scanning.

Electrophoresis in sodium dodecylsulfate containing either 7.5% or 10% polyacrylamide gels was performed as earlier described[29]. Wet slab gels were scanned on fluorescence using the Typhoon Variable Mode Imager (Amersham Biosciences) using $\lambda_{ex}$ 488 nm and $\lambda_{em}$ 520 nm (bandpass 40) for green fluorescent MDW933 and $\lambda_{ex}$ 532 nm and $\lambda_{em}$ 610 nM (bandpass 30) for red fluorescent MDW941.

Fluorescence Microscopy and Multispectral Imaging.

Fibroblasts were cultured on glass slides. Cells were incubated with MDW941 (5 nM) or control probe MDW1065 (5 nM) for 2 h. Next, cells were washed, fixed with 3% (v/v) paraformaldehyde in PBS for 15 min, washed and incubated first with 0.05% (w/v) saponine for 15 min, next with 0.1 mM NH4Cl in PBS for 10 min and then with 3% (w/v) bovine serum albumin in PBS for 1 h. Next, the slides were incubated with anti-GBA monoclonal antibody 8E4 (1:500). Bound mouse monoclonal antibody was visualized with a secondary antibody conjugated with AlexaFluor488. Nuclei were stained with DAPI. Cells were examined using epifluorescence microscopy (Leica DM5000B) with an HCX PL APO X63 1.40-0.60 oil immersion objective. Filter blocks used were A4 (360/40 nm band pass excitation, 400 nm dichromatic mirror, 470/40 nm band pass suppression) for DAP1, L5 (480/40 nm band pass excitation, 505 nm dichromatic mirror, 527/30 nm band pass suppression) for AlexaFluor488 and N2.1 (515-560 nm band pass excitation, 580 nm dichromatic mirror, 590 nm long pass suppression) for MDW941 and MDW1065. Analysis was performed with multispectral imaging using a Nuance N-MSI-420-20 camera with Nuance 2.10 software (Cambridge Research & Instrumentation). Data sets were acquired at 440-500 nm for A4, 500-580 nm for L5, and 580-720 nm for N2.1 filter blocks, each at 10 nm intervals. In each experiment, nonlabeled control cells were imaged to define the autofluorescence spectral library. Spectral libraries for DAPI, AlexaFluor488 and MDW941 or MDW1065, each obtained from single-stained cells, were used to unmix the triple staining patterns into the individual components and separate these from autofluorescence. Nuance software was used to construct composite images.

Fluorescence-Activated Cell Sorting.

Fibroblasts were cultured in the presence or absence of 0.3 mM CBE overnight. Next, cells were incubated with MDW933 (2 and 10 nM, for 300 min). Cells were suspended by trypsinization and analyzed by FACS using FACS Vantage (B.D. Bioscience), $\lambda_{ex}$ 488 nm, $\lambda_{em}$ 530 nm (bandpass filter 30 nm).

Pulse-Chase Experiments.

Fibroblasts were cultured overnight with MDW941 (10 nM), after which they were extensively washed with PBS and incubated with MDW933 (10 nM). Cells were harvested at different time points; homogenates were prepared and subjected to SDS-PAGE. GBA labeled with MDW933 and with MDW941 were separately visualized using the Typhoon Variable Mode Imager with the above described settings.

Labeling of GBA in Live Mice.

Experimental procedures were all approved by the appropriate ethics committee for animal experiments. C57Bl/6J mice were obtained from Harlan and fed a commercially available lab diet (RMH-B; Hope Farms). Two Npc1 BALB/c WT (+/+) mice were injected intravenously via tail vein, using a restrainer with 100 µl PBS or 100 µl 100 nM MDW933 dissolved in PBS. After 2 h of administration the mice were anesthetized with FFM mix (1 ml of fentanylcitrate, 1 ml of midazalam and 2 ml of distilled water), and blood, urine and organs were collected and directly frozen in liquid nitrogen. Homogenates were made in 25 mM potassium phosphate buffer, pH 6.5, supplemented with 0.1% (v/v) Triton X-100 and labeled with MDW941 (100 nM). Homogenates were analyzed as described above.

Chaperone Experiment Using Isofagomine.

A cell line homozygous for N370S was cultured in HAMF12-DMEM medium (Invitrogen) supplied with 10% (v/v) FBS. Cells were cultured for one week with 0, 10, 30 and 300 nM isofagomine in the medium at confluency. In vitro activity: After one week, cells were scraped and lysed, and activity of GBA was measured at 37° C. with 4-methylumbelliferyl β-D-glucopyranoside as described above. The incubation mixture contained the corresponding concentration of isofagomine, 3 mM fluorogenic substrate, 0.2% (w/v) sodium taurocholate and 0.1% (v/v) Triton X-100 in 150 mM McIlvaine buffer, pH 5.2. For in situ labeling, after one week, similarly treated cells were labeled with 10 nM MDW941 for 2 h. Cells were scraped and lysed, and 25 µg of cell lysate was subjected to electrophoresis in sodium dodecylsulfate containing 7.5% polyacrylamide gels. Fluorescence of GBA labeled with MDW941 was imaged as described above and was quantified using the supplied ImageQuant software (5.1).

LITERATURE CITED IN EXAMPLE 2

1. Brady, R. O., Kanfer, J. N., Bradley, R. M. & Shapiro, D. Demonstration of a deficiency of glucocerebroside-cleaving enzyme in Gaucher's disease. *J. Clin. Invest.* 45, 1112-1115 (1966).
2. Grabowski, G. A. Phenotype, diagnosis, and treatment of Gaucher's disease. *Lancet* 372, 1263-1271 (2008).
3. Goker-Alpan, O. et al. The spectrum of Parkinsonian manifestations associated with glucocerebrosidase mutations. *Arch. Neurol.* 65, 1353-1357 (2008).
4. Van Weely, S. et al. Clinical genotype of Gaucher disease in relation to properties of mutant glucocerebrosidase in cultured fibroblasts. *Biochim. Biophys. Acta* 1096, 301-311 (1991).
5. Lachmann, R. H., Grant, I. R., Halsall, D. & Cox, T. M. Twin pairs showing discordance of phenotype in adult Gaucher's disease. *QJM* 97, 199-204 (2004).
6. Barton, N. W. et al. Replacement therapy for inherited enzyme deficiency-macrophage-targeted glucocerebrosidase for Gaucher's disease. *N. Engl. J. Med.* 324, 1464-1470 (1991).
7. Grabowski, G. A. et al. Enzyme therapy in type 1 Gaucher disease: comparative efficacy of mannose-terminated glucocerebrosidase from natural and recombinant sources. *Ann. Intern. Med.* 122, 33-39 (1995).
8. Aerts, J. M., Hollak, C. E., Boot, R. G., Groener, J. E. & Maas, M. Substrate reduction therapy of glycosphingolipid storage disorders. *J. Inherit. Metab. Dis.* 29, 449-456 (2006).
9. Platt, F. M., Neises, G. R., Dwek, R. A. & Butters, T. D. N-butyldeoxynojirimycin is a novel inhibitor of glycolipid biosynthesis. *J. Biol. Chem.* 269, 8362-8365 (1994).
10. Jonsson, L. M. V. et al. Biosynthesis and maturation of glucocerebrosidase in Gaucher fibroblasts. *Eur. J. Biochem.* 164, 171-179 (1987).
11. Ohashi, T. et al. Characterization of human glucocerebrosidase from different mutant alleles. *J. Biol. Chem.* 266, 3661-3667 (1991).
12. Sawkar, A. R. et al. Gaucher disease-associated glucocerebrosidases show mutation-dependent chemical chaperoning profiles. *Chem. Biol.* 12, 1235-1244 (2005).
13. Sawkar, A. R. et al. Chemical chaperones increase the cellular activity of N370S beta-glucosidase: a therapeutic strategy for Gaucher disease. *Proc. Natl. Acad. Sci. USA* 99, 15428-15433 (2002).
14. Ron, I. & Horowitz, M. ER retention and degradation as the molecular basis underlying Gaucher disease heterogeneity. *Hum. Mol. Genet.* 14, 2387-2398 (2005).
15. Mu, T. W. et al. Chemical and biological approaches synergize to ameliorate protein-folding diseases. *Cell* 134, 769-781 (2008).
16. Steet, R. A. et al. The iminosugar isofagomine increases the activity of N370S mutant acid beta-glucosidase in Gaucher fibroblasts by several mechanisms. *Proc. Natl. Acad. Sci. USA* 103, 13813-13818 (2006).
17. Yu, Z., Sawkar, A. R., Whalen, L. J., Wong, C. H. & Kelly, J. W. Isofagomine- and 2,5-anhydro-2,5-imino-D-glucitol-based glucocerebrosidase pharmacological chaperones for Gaucher disease intervention. *J. Med. Chem.* 50, 94-100 (2007).
18. Lieberman, R. L. et al. Structure of acid beta-glucosidase with pharmacological chaperone provides insight into Gaucher disease. *Nat. Chem. Biol.* 3, 101-107 (2007).
19. Kornhaber, G. J. et al. Isofagomine induced stabilization of glucocerebrosidase. *ChemBioChem* 9, 2643-2649 (2008).
20. Shen, J. S., Edwards, N. J., Hong, Y. B. & Murray, G. J. Isofagomine increases lysosomal delivery of exogenous glucocerebrosidase. *Biochem. Biophys. Res. Commun.* 369, 1071-1075 (2008).
21. Liou, B. & Grabowski, G. A. Participation of asparagine 370 and glutamine 235 in the catalysis by acid beta-glucosidase: the enzyme deficient in Gaucher disease. *Mol. Genet. Metab.* 97, 65-74 (2009).
22. Rempel, B. P. & Withers, S. G. Covalent inhibitors of glycosidases and their applications in biochemistry and biology. *Glycobiology* 18, 570-586 (2008).
23. Atsumi, S., Nosaka, C., Iinuma, H. & Umezawa, K. Accumulation of tissue glucosylsphingosine in Gaucher-like mouse induced by the glucosylceramidase inhibitor cyclophellitol. *Arch. Biochem. Biophys.* 304, 302-304 (1993).
24. Hansen, F. G., Bundgaard, E. & Madsen, R. A short synthesis of (+)-cyclophellitol. *J. Org. Chem.* 70, 10139 (2005).
25. Brumshtein, B. et al. Crystal structures of complexes of N-butyl- and N-nonyl-deoxynojirimycin bound to acid beta-glucosidase: insights into the mechanisms of chemical chaperone action in Gaucher disease. *J. Biol. Chem.* 282, 29052 (2007).
26. Kacher, Y. et al. Acid beta-glucosidase: insights from structural analysis and relevance to Gaucher disease therapy. *Biol. Chem.* 389, 1361-1369 (2008).
27. Overkleeft, H. S. et al. Generation of specific deoxynojirimycin-type inhibitors of the non-lysosomal glucosylceramidase. *J. Biol. Chem.* 273, 26522-26527 (1998).
28. Arribas, J. C. et al. Differential mechanism-based labeling and unequivocal activity assignment of the two active sites of intestinal lactase/phlorizin hydrolase. *Eur. J. Biochem.* 267, 6996-7005 (2000).
29. Aerts, J. M. et al. Glucocerebrosidase, a lysosomal enzyme that does not undergo oligosaccharide phosphorylation. *Biochim. Biophys. Acta* 964, 303-308 (1988).

30. van Weely, S. et al. Role of pH in determining the cell-type-specific residual activity of glucocerebrosidase in type 1 Gaucher disease. *J. Clin. Invest.* 91, 1167-1175 (1993).
31. Chang, H. H., Asano, N., Ishii, S., Ichikawa, Y. & Fan, J. Q. Hydrophilic iminosugar active-sitespecific chaperones increase residual glucocerebrosidase activity in fibroblasts from Gaucher patients. *FEBS J.* 273, 4082-4092 (2006).
32. Rudensky, B. et al. Fluorescent flow cytometric assay: a new diagnostic tool for measuring beta-glucocerebrosidase activity in Gaucher disease. *Blood Cells Mol. Dis.* 30, 97-99 (2003).
33. Gloster, T. M., Madsen, R. & Davies, G. J. Structural basis for cyclophellitol inhibition of a betaglucosidase. *Org. Biomol. Chem.* 5, 444-446 (2007).
34. Zechel, D. L. et al. Iminosugar glycosidase inhibitors: structural and thermodynamic dissection of the binding of isofagomine and 1-deoxynojirimycin to beta-glucosidases. *J. Am. Chem. Soc.* 125, 14313-14323 (2003).
35. Phenix, C. P. et al. Imaging of enzyme replacement therapy using PET. *Proc. Natl. Acad. Sci. USA* 107, 10842-10847 (2010).
36. Aerts, J. M. F. G. et al. A procedure for the rapid purification in high yield of human glucocerebrosidase using immunoaffinity chromatography with monoclonal antibodies. *Anal. Biochem.* 154, 655 (1986).
37. Boot, R. G. et al. Glucocerebrosidase genotype of Gaucher patients in The Netherlands: Limitations in prognostic value. *Hum. Mutat.* 10, 348 (1997).
38. Andersson, U., Butters, T. D., Dwek, R. A. & Platt, F. M. N-butyldeoxygalactonojirimycin: a more selective inhibitor of glycosphingolipid biosynthesis than N-butyldeoxynojirimycin, in vitro and in vivo. *Biochem. Pharmacol.* 59, 821 (2000).

Example 3

Compounds are referred to herein below by their chemical name, an arbitrary name and/or by an arbitrary number. The chemical structures that are associated with these names and number are depicted in FIG. 22.

Results

Synthesis of the Probes

KY170 4, and fluorescent probes MDW933 5 and MDW941 6 were synthesized as follows (See also FIG. 38, scheme 1). First, core carbocycle 10 was synthesized in 7 steps from D-xylose as described (1). Selective tosylation of the primary alcohol in 1 by treatment with p-toluenesulfonyl chloride in $CH_2Cl_2$ followed by substitution of the tosylate with sodium azide afforded azido alcohol 11 in 72%. The benzyl groups in 11 were removed under the agency of $BCl_3$ prior to epoxidation. The resulting free hydroxyls were protected as the corresponding benzoyl protective groups using benzoyl chloride in pyridine. Epoxidation of cyclohexene 12 using in situ formed methyl(trifluoromethyl)dioxirane gave epoxides 13 and 14 as a separable mixture. Deprotection with sodium methoxide in methanol gave 8-deoxy-8-azidocyclophellitol (KY170, 4). BODIPY Green-alkyne 15 (green fluorescent) or BODIPY Redalkyne 16 (red fluorescent) was conjugated to KY170 4 using copper-catalyzed click chemistry, giving MDW933 5 and MDW941 6 respectively. Non-reactive control probes MDW1064 8 and MDW1065 9 were synthesized by removing the protective groups in azido alcohol 11 with $BCl_3$ and subsequent conjugation to either BODIPY Green 15 or BODIPY Red 16.

Determination of Inhibition Constants

Previously discontinuous methods have been used to determine the inhibition constants of glycosidase inhibitors. This method however proved to be unsuitable for the determination of the inhibition constants of KY170 4, MDW933 5 and MDW941 6 due to their high affinity/fast binding. Therefore the inhibition constants have been determined in a continuous substrate assay which was first described in 1982 (2) and has recently been reappraised in 2010 (3). In these experiments, inhibition of the enzyme and hydrolysis of the substrate proceed concurrently making the situation slightly more complex than the discontinuous (FIG. 39 Scheme 2). The time-dependent interaction of inhibitor (I) with free β-glucosidase (E) was considered to occur in separate stages (A). A rapid reversible interaction is followed by a slower, irreversible reaction that transforms the reversible enzyme-inhibitor complex (EI) into an irreversible enzyme-inhibitor complex (EI*) (FIG. 39 Scheme 2). Progress curves were obtained (FIG. 28a) and apparent rate constant k' was plotted versus the concentration (FIG. 28b) to obtain estimates of the $K_i$ (equilibrium constant) and $k_i$ (rate constant)

Molecular Docking

Molecular docking was performed with KY170 4, MDW933 5 and MDW941 6 as ligands. MDW933 5 and MDW941 6 revealed to bind tightly to the GBA active site (FIG. 29). Both probes displayed free binding energies of ~8 kcal/mol. For both ligands we observed binding of the polar cyclophellitol head group in the active site pocket, with the epoxide being within 4 Angstrom of E340. The region immediately outside the active site pocket on the protein surface accommodated the hydrophobic tails. Inspection of binding showed tight binding of the hydrophobic part of the ligand with this part of the protein. Binding of KY170 4 was much weaker in the range of 5 kcal/mol, further illustrating how the hydrophobic tail greatly increased the binding affinity.

Cellular Uptake of the Probes

To identify the mechanism of entry of the probes, we performed a temperature experiment. We incubated cells with a serial dilution of MDW933 5 either at 18° C., a temperature at which endocytosis is blocked, or 37° C. for 2 hours. We harvested the cells and determined the residual activity using a fluorogenic substrate assay. The residual activities showed that the temperature did not have an pronounced effect on in situ inhibition. At both temperatures, 10 nM MDW933 5 blocked glucocerebrosidase activity in situ (SI FIG. 33). We therefore exclude that the uptake is solely by endocytosis.

Methods

All reagents were of a commercial grade and were used as received unless stated otherwise. Isofagomine 1 (4), cyclophellitol 3 (1) and BODIPY alkyne green 15 and red 16 (5) were synthesized as described in literature and their spectral data was in accordance with those reported in literature. The AMP-DNM 7 used in this research was from a previously synthesized batch (6). Diethyl ether ($Et_2O$), ethyl acetate (EtOAc), light petroleum ether and toluene were obtained from Riedel-de Haen. Acetonitrile, dichloromethane, dimethylformamide (DMF), methanol (MeOH), pyridine, tetrahydrofuran (THF) were purchased from Biosolve. Dichloromethane was distilled from $CaH_2$ and THF was distilled over $LiAlH_4$ prior to use. All reactions were performed under an inert atmosphere or Argon unless stated otherwise. Solvents used for flash chromatography were of pro analysi quality. Reactions were monitored by TLC analysis using Merck aluminum sheets precoated with silica gel 60 with detection by UV-absorption (254 nm) and by spraying with a solution of $(NH_4)_6Mo_7O_{24}.H_2O$ (25 g/L) and $(NH_4)_4Ce(SO_4)_4.H_2O$ (10 g/L) in 10% aqueous sulfuric acid followed by charring at ~150° C. or by spraying with 20% sulfuric acid in ethanol followed by charring at ~150° C. Column chromatography was performed using either Baker- or Screening Device silica gel in the indicated solvents. $^1$H NMR and $^{13}$C NMR spectra were recorded on a Bruker DMX-400 (400/100 MHz) or a Bruker AV-400 (400/100 MHz) spectrometer in the given solvent. Chemical shifts are reported as δ-values in ppm relative to the chloroform residual solvent peak or tetramethylsilane (TMS) as internal standard. Coupling constants are given in Hz. All given $^{13}$C spectra are proton decoupled. Spin multiplicities are given as s, d, dd, ddd, dddd, dt, t, td, q and m. High resolution mass spectra were recorded with a LTQ Orbitrap (Thermo Finnigan). LC/MS analysis was performed on a Jasco HPLC system (detection simultaneously at 214 nm and 254 nm) equipped with an analytical Alltima C18 column (Alltech, 4.6 mmD×250 mL, 5μ particle size) in combination with buffers A: $H_2O$, B: acetonitrile and C: 1% aq. TFA and coupled to a Perkin Elmer Sciex API 165 mass instrument.

Optical rotations were measured on a Propol automatic polarimeter (sodium D line, λ=589 nm). FTIR-spectra were recorded on a Paragon-PE 1000.

(1R,2R,5S,6S)-2-(azidomethyl)-5,6-bis(benzyloxy)cyclohex-3-enol (11)

To a solution of 10 (1.24 g, 3.65 mmol) in dichloromethane (26 mL) were added p-toluenesulfonylchloride (1.04 g, 5.48 mmol, 1.1 equiv.) and triethylamine (0.90 mL, 6.57 mmol, 1.8 equiv.) at 0° C. The solution was stirred for 5 h before being poured in 1M HCl solution. The mixture was extracted with $Et_2O$ and the organic layer was dried over $MgSO_4$ before being concentrated in vacuo, yielding the crude tosylate which was immediately subjected to azidation. To a solution of tosylated intermediate (1.75 g, 3.65 mmol) in DMF (35 ml) was added sodium azide (2.40 g, 36.7 mmol, 10.4 equiv.). The solution was stirred for 24 h at 60° C. before being concentrated in vacuo. The crude product was diluted with EtOAc, washed with 1 M HCl, saturated aqueous $NaHCO_3$ and brine. The combined organic layers were dried over $MgSO_4$ and concentrated in vacuo. Purification by silica column chromatography (8%→16% EtOAc in petroleum ether) afforded 11 (900 mg, 2.46 mmol, 71%) as an amorphous solid. $^1$H NMR (400 MHz, $CDCl_3$): δ 7.33-7.26 (m, 10H), 5.79 (dt, J=10.4, 2.4 Hz, 1H), 5.58 (dt, J=10.4, 2.4 Hz, 1H), 5.02 (d, J=11.3, 1H), 4.7 (dd, J=11.2, 5.4 Hz, 2H), 4.65 (d, J=11.2 Hz, 1H), 4.21-4.19 (m, 1H), 3.61-3.53 (m, 3H), 3.44 (dd, J=12.0, 6.0 Hz, 1H), 2.83 (s, 1H) and 2.48 (br, 1H). $^{13}$C NMR (100 MHz, $CDCl_3$): δ 138.1, 137.2, 128.7, 128.6, 128.0, 127.9, 127.8, 127.7, 83.5, 80.3, 75.0, 71.6, 52.5 and 43.6. FT-IR: νmax (neat)/cm$^{-1}$: 2095.9, 1497.1, 1453.9, 1275.9, 1092.6, 1050.4, 1027.7, 732.0 and 695.9. $[α]^{20}_D$+137.8° (c=1, $CHCl_3$). LC/MS: $R_t$ 9.35; linear gradient 10→90% B in 13.5 min; ESI/MS: m/z=383.1 $[M+NH_4]^+$. HRMS: (M+3H$^+$—N2) calcd for $C_{21}H_{26}NO_3$ 340.19072 found 340.19080.

(1R,2R,3S,6R)-6-(azidomethyl)cyclohex-4-ene-1,2,3-triyl tribenzoate (12)

Borontrichloride (21 mL, 1M in $CH_2Cl_2$, 21.1 mmol, 10 equiv.) was added to a solution of 11 (777.1 mg, 2.11 mmol) in anhydrous dichloromethane (10 mL) at −78° C. The reaction mixture was stirred at −78° C. for 6 h before being quenched with MeOH. The solution was concentrated in vacuo giving the triol intermediate, which was immediately used for benzoylation. The crude product was coevaporated several times with anhydrous toluene before being dissolved in pyridine (10 mL). Benzoylchloride (2.6 mL, 21.1 mmol, 10 equiv.) was added at 0° C. and the reaction mixture was stirred for 18 h at ambient temperature. The mixture was quenched with saturated aqueous $NaHCO_3$, extracted with EtOAc, dried over $MgSO_4$ and concentrated in vacuo. Purification by silica column chromatography (4%→6% EtOAc in petroleum ether) afforded 12 (701.8 mg, 1.46 mmol, 70%) as a yellow oil. $^1$H NMR (400 MHz, $CDCl_3$): δ 7.99 (d, J=7.2 Hz, 2H), 7.92 (d, J=7.2 Hz, 2H), 7.84 (d, J=7.2 Hz, 2H), 7.53-7.46 (m, 3H), 7.40 (dt, J=24.4, 8.0 Hz, 5H), 7.26-7.18 (m, 2H), 6.00-5.93 (m, 3H), 5.86 (d, J=10.0 Hz, 1H), 5.72 (t, J=9.2 Hz, 1H), 3.64 (dd, J=12.4, 4.0 Hz, 1H), 3.46 (dd, J=12.4, 6.4 Hz, 1H) and 2.99-2.97 (m, 1H). $^{13}$C NMR (100 MHz, $CDCl_3$): δ 166.0, 165.9, 133.3, 133.2, 133.1, 129.8, 129.7, 129.6, 129.4, 129.0, 128.9, 128.5, 128.4, 128.3, 126.2, 127.0, 72.7, 72.7, 72.6, 70.4, 52.0 and 42.5. FT-IR: $ν_{max}$ (neat)/cm$^{-1}$: 2100.3, 1718.0, 1601.8, 1585.4, 1492.2, 1314.5, 1250.8, 1178.0, 1108.8, 1031.8, 1025.9, 950.7, 855.3, 778.1, 705.0 and 686.1. $[α]^{20}_D$+173° (c=1.0, $CHCl_3$). LC/MS: $R_t$ 10.68; linear gradient 10→90% B in 13.5 min; ESI/MS: m/z=498.2 $[M+H]^+$. HRMS: (M+Na$^+$) calcd for $C_{28}H_{25}NO_6$ 520.14791 found 520.14724.

(2S,3R,4S,5S)-2,3,4-Benzoyl-8-azido-8-deoxy-cyclophellitol (13 and 14)

A solution of 0.4 mM $Na_2EDTA$ solution in $H_2O$ (3.1 mL) and trifluoroacetone (1.34 mL, 15 mmol, 15 equiv.) were added to 12 (497 mg, 1.0 mmol) in acetonitrile (6.7 mL). A mixture of oxone (3.07 g, 5.0 mmol, 5 equiv.) and $NaHCO_3$ (588.1 mg, 7.0 mmol, 7 equiv.) was added to the solution over a period of 15 min. After stirring at 4° C. for 4 h, an additional amount of 0.4 mM $Na_2EDTA$ in $H_2O$ (1.5 mL), trifluoroacetone (0.7 mL, 7.5 mmol, 7.5 equiv.) and a mixture of oxone (1.5 g, 2.5 mmol, 2.5 equiv.) and $NaHCO_3$ (290 mg, 3.5 mmol, 3.5 equiv.) were added to the reaction mixture over a period of 15 min. The reaction mixture was stirred at 4° C. for 30 min before being diluted with $H_2O$. After extraction of the water layer with EtOAc, the combined organic layers were dried over $MgSO_4$ and concentrated in vacuo. Purification by silica column chromatography (8%→10% $Et_2O$ in petroleum ether) and (16%→18% $Et_2O$ in petroleum ether) afforded 13 (103.9 mg, 0.20 mmol, 20%) and 14 (253.7 mg, 0.49 mmol, 49%) respectively as amorphous solid. 14: $^1$H NMR (400 MHz, $CDCl_3$): δ 8.03 (d, J=7.4 Hz, 2H), 7.88 (d, J=7.6 Hz, 2H), 7.79 (d, J=7.6 Hz, 2H), 7.56 (t, J=7.2 Hz, 1H), 7.46-7.36 (m, 5H), 7.32 (t, J=7.6 Hz, 2H), 7.24 (t, J=7.2, 2H), 5.84 (t, J=9.2 Hz, 1H), 5.56 (d, J=8.8 Hz, 1H), 5.43 (t, J=10.0 Hz, 1H), 3.67-3.62 (m, 4H), 3.44 (s, 1H) and 2.71 (dddd, J=9.3, 7.6, 1.4 Hz, 1H). $^{13}$C NMR (100 MHz, $CDCl_3$): δ 165.7, 165.6, 165.4, 133.5, 133.3, 133.1, 129.8, 129.6, 129.5, 128.9, 128.7, 128.6, 128.4, 128.3, 128.1, 72.2, 71.4, 67.8, 54.7, 54.2, 50.5 and 40.8. FT-IR: $ν_{max}$ (neat)/cm$^{-1}$: 2104.5, 1722.6, 1601.9, 1451.6, 1315.2, 1258.3, 1178.4, 1094.8, 1069.6, 1026.1, 853.8, 706.6 and 686.1. $[α]^{20}$D+93.6° (c=1.0, $CHCl_3$). LC/MS: $R_t$ 10.24; linear gradient 10→90% B in 13.5 min; ESI/MS: m/z=514.2 $[M+H]^+$. HRMS: (M+H$^+$) calcd for $C_{28}H_{23}N_3O_7$ 514.16088 found 514.16007.

13: $^1$H NMR (400 MHz, $CDCl_3$): δ 8.02 (d, J=7.2 Hz, 2H), 7.89 (d, J=7.2 Hz, 2H), 7.78 (d, J=7.2 Hz, 2H), 7.53-7.19 (m, 5H), 5.96 (t, J=9.6 Hz, 1H), 5.77 (d, J=8.8 Hz, 1H), 5.55 (t, J=9.6 Hz, 1H), 3.77-3.74 (m, 2H), 3.64 (dd, J=12.8, 4.0 Hz, 1H), 3.32 (s, 1H) and 2.68 (ddd, J=9.2, 5.2, 3.8 Hz, 1H). $^{13}$C NMR (100 MHz, $CDCl_3$): δ 166.0, 165.9, 165.6, 133.4, 133.0, 129.9, 129.7, 129.5, 129.0, 128.9, 128.6, 128.4, 128.3, 128.1, 72.1, 70.0, 69.9, 54.6, 53.8, 50.8 and 40.9. FT-IR: $ν_{max}$ (neat)/cm$^{-1}$: 2104.6, 1717.8, 1602.1, 1451.8, 1249.4, 1178.1, 1093.3, 1069.0, 1026.0 and 704.5. $[α]^{20}$D+52.4° (c=1.0, CHCl$_3$). LC/MS: R$_t$ 10.22; linear gradient 10→90% B in 13.5 min; ESI/MS: m/z=514.2 [M+H]$^+$. HRMS: (M+H$^+$) calcd for C$_{28}$H$_{23}$N$_3$O$_7$ 514.16088 found 514.16017.

(2S,3R,4S,5S)-8-azido-8-deoxy-cyclophellitol (KY170, 4)

A catalytic amount of NaOMe was added to a solution of 14 (103.9 mg, 0.20 mmol) in MeOH (1.0 mL) and stirred for 1 h at ambient temperature. The reaction mixture was neutralized with Amberlite IR-120 H$^+$, filtered and concentrated in vacuo. Purification by silica column chromatography (6%→8% MeOH in dichloromethane) provided KY170 4 (30.0 mg, 0.15 mmol, 75%). $^1$H NMR (400 MHz, MeOD): δ 3.84 (dd, J=8.4, 3.6 Hz, 1H), 3.67 (d, J=8.0 Hz, 1H), 3.51 (dd, J=12.0, 8.8 Hz, 1H), 3.36 (d, J=3.2 Hz, 1H), 3.23 (dd, J=10.0, 8.4 Hz, 1H), 3.13-3.08 (m, 2H), 2.07 (ddt, J=9.4, 3.6, 1.6 Hz, 1H). $^{13}$C NMR (100 MHz, MeOD): δ 78.3, 72.7, 68.6, 57.6, 56.1, 52.4 and 43.9. FT-IR: ν$_{max}$ (neat)/cm$^{-1}$: 3331.7, 3187.9, 2936.1, 2097.6, 1455.8, 1345.9, 1273.4, 1144.2, 1092.5, 1066.5, 1032.1, 995.1, 926.6, 899.8, 818.7, 803.5, 714.1 and 652.0. [α]$^{20}_D$+174.7° (c=0.6, MeOH). LC/MS: Rt 0.95; linear gradient 1090% B in 13.5 min; ESI/MS: m/z=219.2 [M+NH$_4$]+. HRMS: (M+3H$^+$—N2) calcd for C$_7$H$_{14}$NO$_4$ 176.09173 found 176.09179.

MDW933 5

KY170 4 (8.51 mg, 42 µmol) and BODIPY Green-alkyne 15 (13.8 mg, 42 µmol) (5) were dissolved in tert-BuOH/Tol/H$_2$O (1.8 mL, 1/1/1 v/v/v). CuSO$_4$ (100 mM in H$_2$O, 42 µL, 4.2 µmol) and sodium ascorbate (100 mM in H$_2$O, 63 µL, 6.3 µmol) were added. Subsequently, the reaction was heated to 80° C. and stirred overnight. The solution was diluted with CH$_2$Cl$_2$, washed with H$_2$O, dried and concentrated. Purification over silica gel column chromatography (0%→5% MeOH/CH$_2$Cl$_2$) gave MDW933 5 as an orange powder (56%, 12.49 mg, 23.6 µmol). $^1$H NMR (600 MHz, CDCl$_3$) δ ppm 7.40 (s, 1H), 6.01 (s, 2H), 4.68 (d, J=12.0 Hz, 1H), 4.58 (dd, J=13.4, 7.5 Hz, 1H), 3.66 (d, J=5.6 Hz, 1H), 3.40-3.34 (m, 1H), 3.20-3.15 (m, 1H), 3.02 (s, 1H), 2.97 (s, 1H), 2.96-2.91 (m, 2H), 2.73 (t, J=6.4, 6.4 Hz, 2H), 2.49-2.46 (s, 6H), 2.45-2.40 (m, 1H), 2.33 (s, 6H), 1.86 (td, J=15.0, 7.6, 7.6 Hz, 2H), 1.66-1.58 (m, 2H). $^{13}$C NMR (150 MHz, CDCl$_3$) δ ppm 153.9, 146.0, 140.3, 131.4, 121.7, 77.2, 77.0, 76.9, 76.7, 71.1, 67.4, 56.0, 54.5, 49.6, 43.0, 31.2, 29.5, 28.1, 25.2, 16.3, 14.4. LC/MS: Rt 6.83; linear gradient 10→90% B in 13.5 min; ESI/MS: m/z=530.00 [M+H]$^+$. HRMS: (M+H$^+$) calcd for C$_{26}$H$_{34}$BF$_2$N$_5$O$_4$ 530.27447 found 530.27454.

MDW941 6

KY170 4 (5.46 mg, 27 µmol) and BODIPY Red-alkyne 16 (13.1 mg, 27 µmol) (5) were dissolved in tert-BuOH/Tol/H$_2$O (1.5 mL, 1/1/1 v/v/v). CuSO$_4$ (100 mM in H$_2$O, 27 µL, 2.7 µmol) and sodium ascorbate (100 mM in H$_2$O, 41 µL, 4.1 µmol) were added. Subsequently, the reaction was heated to 80° C. and stirred overnight. The solution was diluted with CH$_2$Cl$_2$, washed with H$_2$O, dried and concentrated. Purification over silica gel column chromatography (0%→5% MeOH in dichloromethane) gave MDW941 6 as an purple powder (77%, 14.32 mg, 20.8 µmol). $^1$H NMR (400 MHz, CDCl$_3$) δ ppm 7.80 (d, J=8.5 Hz, 4H), 7.36 (s, 1H), 7.17 (d, J=3.4 Hz, 2H), 6.89 (d, J=8.5 Hz, 4H), 6.54 (d, J=3.8 Hz, 2H), 5.12-4.83 (m, 1H), 4.80-4.46 (m, 3H), 3.77 (s, 6H), 3.75-3.68 (m, 1H), 3.45-3.34 (m, 1H), 3.26-3.13 (m, 1H), 3.11-3.02 (m, 1H), 3.00-2.94 (m, 1H), 2.90-2.78 (m, 2H), 2.73-2.58 (m, 2H), 2.51-2.36 (m, 1H), 2.08-1.91 (m, 2H), 1.84-1.67 (m, 4H). $^{13}$C NMR (150 MHz, CDCl$_3$) δ ppm 160.5, 157.4, 144.6, 136.0, 130.9, 126.8, 125.0, 120.0, 113.7, 71.0, 67.2, 56.0, 55.2, 54.4, 49.6, 42.7, 33.0, 30.3, 29.7, 29.4, 25.0. LC/MS: Rt 8.35; linear gradient 10→90% B in 13.5 min; ESI/MS: m/z=686.07 [M+H]$^+$. HRMS: (M+H$^+$) calcd for C36H38BF2N5O4 686.29560 found 686.29559.

(1R,2R,3S,6R)-6-(azidomethyl)cyclohex-4-ene-1,2,3-triol (17)

Azide 11 (103 mg, 0.28 mmol) was dissolved in CH$_2$Cl$_2$ (5 mL) and cooled to −78° C. before BCl$_3$ (5 mL, 1M in CH$_2$Cl$_2$) was added. After 4 h stirring at −78° C., the reaction was quenched by the addition of MeOH. The temperature was raised to room temperature and the solution was concentrated in vacuo. Trace of BCl$_3$ were removed by coevaporating with MeOH. The resulting crude triol 17 was used as such in the click reaction.

MDW1064 (8)

Azide 17 (37 mg, 0.15 mmol) was dissolved in DMF (2 mL). To the solution was added BODIPY Green-alkyne (82 mg, 0.25 mmol), CuSO$_4$ (1M in H$_2$O, 15 µL, 15 µmol) and sodium ascorbate (1M in H$_2$O, 23 µL, 23 µmol). The reaction was stirred overnight, after which TLC analysis revealed complete conversion. The solution was diluted with EtOAc, washed with 1M HCl, NaHCO$_3$ and brine, dried over Na$_2$SO$_4$ and concentrated under reduced pressure. Silica gel column chromatography (CH$_2$Cl$_2$→5% MeOH/CH$_2$Cl$_2$) afforded MDW1064 8 as an orange amorphous solid (72%, 55.3 mg, 108 µmol). $^1$H NMR (400 MHz, CDCl$_3$/MeOD) δ ppm 7.48 (s, 1H), 6.08 (s, 2H), 5.58 (td, J=10.2, 2.3, 2.3 Hz, 1H), 5.43 (td, J=10.4, 2.0, 2.0 Hz, 1H), 4.61 (dd, J=13.8, 3.8 Hz, 1H), 4.47 (dd, J=13.9, 7.3 Hz, 1H), 3.99-3.95 (m, 1H), 3.47 (dd, J=9.9, 8.0 Hz, 1H), 3.30 (t, J=9.7, 9.7 Hz, 1H), 3.03-2.98 (m, 2H), 2.78 (t, J=7.5, 7.5 Hz, 2H), 2.75-2.67 (m, 1H), 2.49 (s, 6H), 2.40 (s, 6H), 1.95-1.86 (m, 2H), 1.74-1.64 (m, 2H). $^{13}$C NMR (150 MHz, CDCl$_3$/MeOD) δ ppm 153.4, 146.8, 145.7, 140.2, 130.9, 130.5, 125.0, 121.9, 121.3, 76.8, 71.6, 70.3, 50.6, 44.0, 30.9, 29.2, 27.6, 24.7, 15.7, 13.7. LC/MS: R$_t$ 7.22; linear gradient 10→90% B in 13.5 min; ESI/MS: m/z=513.87 [M+H]$^+$.

MDW1065 (9)

Azide 17 (33 mg, 0.15 mmol) was converted to the title compound as described above. To the solution was added BODIPY Red-alkyne (100 mg, 0.25 mmol), CuSO$_4$ (1M in H$_2$O, 15 µL, 15 µmol) and sodium ascorbate (1M in H$_2$O, 23 µL, 23 µmol). The reaction was stirred overnight, after which TLC analysis revealed complete conversion. The solution was diluted with EtOAc, washed with 1M HCl, NaHCO$_3$ and brine, dried over Na$_2$SO$_4$ and concentrated under reduced pressure. Silica gel column chromatography (CH$_2$Cl$_2$→5% MeOH/CH$_2$Cl$_2$) afforded title MDW1065 9 as a purple solid (70%, 71 mg, 106 µmol). 1H NMR (400 MHz, CDCl$_3$) δ ppm 7.89-7.78 (m, 4H), 7.36-7.27 (m, 1H), 7.27-7.21 (m, 2H), 6.96-6.89 (m, 4H), 6.62-6.56 (m, 2H), 5.61-5.53 (m, 1H), 5.48-5.36 (m, 1H), 4.54-4.45 (m, 2H), 4.01-3.93 (m, 1H), 3.86-3.79 (m, 6H), 3.50 (t, J=8.8, 8.8 Hz, 1H), 3.29 (t, J=9.6, 9.6 Hz, 1H), 3.00-2.87 (m, 2H), 2.81-2.65 (m, 2H), 2.63-2.48 (m, 1H), 1.91-1.75 (m, 4H). $^{13}$C NMR (150 MHz, CDCl$_3$) δ ppm 160.4, 157.4, 147.2, 144.6, 135.9, 130.8, 126.7, 125.4, 125.0, 122.0, 119.9, 113.6, 77.1, 71.8, 70.3, 55.1, 50.8, 44.3, 32.9, 30.2, 29.2, 24.9. LC/MS: R$_t$ 8.36; linear gradient 10→90% B in 13.5 min; ESI/MS: m/z=670.00 [M+H]$^+$.

Determination of the Binding Constants

To 100 µL McIlvaine buffer (pH 5.2, 0.2% sodium taurocholate, 0.1% Triton X-100) containing 4-methylumbelliferyl β-D-glucoside (7.5 mM) in Greiner flat bottom black 96-well plate was added 5 µL inhibitor (25× stock in DMSO). The resulting mixture was preincubated at 37° C. for 15 min in a TECAN GENios microplate reader. GBA (2 ng) in McIlvaine buffer (20 µL pH 5.2, 0.2% sodium taurocholate, 0.1% Triton X-100) was preheated to 37° C. for 15 min before being added to the substrate mix. The resulting solution was mixed by horizontal shaking for 15 sec, after which release 4-methylumbelliferyl measured with a TECAN GENios platereader ($\lambda_{ex}$ 340 nm and $\lambda_{em}$ 465 nm) for the indicated time. Bleaching of the fluorophore, which was observed during the assay, was corrected by subtracting blanks (100 µL substrate buffer, 5 µL DMSO, 20 µL McIlvaine buffer). Apparent rate constants k' were obtained by fitting the resulting progress curves (FIG. 28A) to the one-phase association equitation y (y max y0)(1−exp$^{-kt}$)yo+in GraphPad Prism version 5.00 for Windows, GraphPad Software, San Diego Calif. USA, www.graphpad.com. Measurements were performed in nine fold and plotting of the obtained k' values versus [$^I$0] yielded rectangular hyperbolar functions (FIG. 28B).
Using the equitation $$k' = \frac{k_i[I_0]}{K_I^{app} + [I_o]}$$

estimates of $K_{i\ app}$ and $k_i$ were obtained. The $K_i$ value in the absence of substrate was obtained by correcting the $K_{i\ app}$ with $$\left(1 + \frac{[S]}{K_m}\right)$$

The Km of 4-methylumbelliferyl β-D-glucoside for GBA is 1.2 mM.
Molecular Docking KY170 4, MDW933 5, and MDW941 6 were docked on GBA as follows. Allowing conformational changes in the small compounds, enzyme-ligand complexes were simulated with a low free energy. Ligand molecules were prepared using MarvinSketch. Lowest energy conformers were calculated and saved as .pdb files that were used as input for Autodock-Tools. Rotatable bonds were defined and .pdbqt files were generated that served as input for Autodock Vina (7). Similarly, protein .pdbqt files were also prepared using Autodock-Tools. The protein file was produced from the crystal structure coordinates of glucocerebrosidase in the open state (pdb 2VE3,(8)). Autodock Vina experiments were run on a 2.66 GHz Intel duo core iMac computer (Apple Macintosh). Flexible docking experiments were run using standard settings apart from the exhaustiveness, which was set at 10. A search space spanning roughly 30 cubic Ångströms around the active site was defined.
Time-Lapse Microscopy Fibroblasts were cultured in chamber slides (Lab-Tek II, Nunc, Roskilde, Denmark) and incubated with 5 nM compound MDW933 5 or MDW941 6; immediately after which mineral oil was thinly layered on top of the culture medium to prevent evaporation. With the 37° C., 10% $CO_2$ incubator enclosing the microscope, cells were imaged every 5 min for 2 hours simultaneously using fluorescence microscopy with an N2.1 filter block and phase-contrast brightfield microscopy (Leica IR-BE with Z-motor drive and a Plan APO 63×/1.40 oil immersion objective (Leica Microsystems, Rijswijk, The Netherlands), equipped with a KX85 camera, Apogee Instruments, Auburn, Calif., USA). To minimize photo-toxicity fluorescence imaging was limited to 2 h; to monitor for possible toxicity due to the presence of MDW933 5 or MDW941 6, after 2 h live-cell imaging was continued with bright field microscopy only for another 98 hours. An autofocus routine was applied during acquisition. Images were analyzed using TimeLapseAVI 5.1.4 software (©Ron Hoebe, CMO, AMC, University of Amsterdam, The Netherlands; R.A.Hoebe@amc.uva.nl).
Mass Spectrometric Analysis of GBA Labeled with KY170 4 and MDW933 5
Identification of the Site of Binding of KY170 4

GBA (5 µg) was labeled with 6 µM KY170 4 in McIlvaine buffer (150 mM, pH 5.2, 0.2% sodium taurocholate (w/v), 0.1% Triton X-100 (v/v)) for 1 h at 37° C. (10 µL end volume). Prior to digestion the pH was adjusted by the addition of 200 mM $NH_4HCO_3$ (pH 8.0), and the protein was reduced with 10 mM dithiothreitol for 30 min at 60° C. and alkylated with 15 mM iodoacetamide for 30 min at RT in the dark. The labeled protein was digested by addition of 50 ng trypsin (sequencing grade modified, Promega) and incubation at 37° C. overnight. Protein digests were desalted using reversed phase C18-Ziptips (2 µg capacity, Millipore). After activation in acetonitrile and loading of the samples, the Ziptips were washed with 0.1% aqueous trifluoroacetic acid and eluted with 60% acetonitrile, 0.1% trifluoroacetic acid and 39.9% water. Prior to loading onto the LC-MS system samples were diluted 10-fold with 0.1% aqueous trifluoroacetic acid.
Identification of the Site of Binding of MDW933

Some 40 µg of recombinant GBA (1 µg/µL) was diluted in 60 µL McIlvaine buffer (150 mM, pH 5.2, 0.2% sodium taurocholate (w/v), 0.1% Triton X-100 (v/v)), incubated with MDW933 5 (10 µL, 20 µM stock in DMSO) for 1 h at 37° C. and precipitated with chloroform/methanol (C/M, (9)). The protein pellet was rehydrated in 90 µL 8 M urea/100 mM $NH_4HCO_3$, reduced with 5 µL 90 mM dithiothreitol for 30 min at 37° C., alkylated with 7.5 µL 200 mM iodoacetamide for 30 min at RT in the dark and desalted by C/M. The pellet was dispersed in 100 µL 8 M urea/50 mM $Na_2CO_3$ buffer (pH 9.4). To 50 µL of the protein solution was added 5 µL hydroxylamine hydrochloride (10 M) and 45 µL 8 M Urea/50 mM $Na_2CO_3$ buffer (pH 9.2). The pH was adjusted to pH ~9.2 by the addition of NaOH (5M). The resulting mixture was incubated overnight at 37° C., precipitated with C/M, redissolved in 10 µL 8 M urea/100 mM $NH_4HCO_3$, diluted with 90 µL digest buffer (100 mM Tris-HCl pH 7.8, 100 mM NaCl, 1 mM $CaCl_2$, 2% ACN) and digested with 500 ng trypsin overnight at 37° C. Peptides were collected and desalted on stage tips (10).
LC-MS Analysis Tryptic peptides were analyzed on a Surveyor nanoLC system (Thermo) hyphenated to a LTQOrbitrap mass spectrometer (Thermo). Gold and carbon coated emitters (OD/ID=360/25 µm tip ID=5 µm), trap column (OD/ID=360/100 µm packed with 25 mm robust Poros®10R2/15 mm BioSphere C18 5 µm 120 Å) and analytical columns (OD/ID=360/75 µm packed with 20 cm BioSphere C18 5 µm 120 Å) were from Nanoseparations (Nieuwkoop, The Netherlands). The mobile phases (A: 0.1% FA/H2O, B: 0.1% FA/ACN) were made with ULC/MS grade solvents (Biosolve). The emitter tip was coupled end-to-end with the analytical column via a 15 mm long TFE teflon tubing sleeve (OD/ID 0.3×1.58 mm, Supelco, USA) and installed in a stainless steel holder mounted in a nano-source base (Upchurch scientific, Idex, USA).

General mass spectrometric conditions were: an electrospray voltage of 1.8 kV was applied to the emitter, no sheath and auxiliary gas flow, ion transfer tube temperature 150° C., capillary voltage 41V, tube lens voltage 150V. Internal mass calibration was performed with air-borne protonated polydimethylcyclosiloxane (m/z=445.12002) and the plasticizer protonated dioctyl phthalate ions (m/z=391.28429) as lock mass (11). 10 µL of the samples was pressure loaded on the trap column with a 10 µL/min flow for 5 min followed by peptide separation with a gradient of 35 min 5-30% B, 15 min 30-60% B, 5 min A at a flow of 300 µL/min split to 250 nL/min by the LTQ divert valve. For each data dependent cycle, one full MS scan (300-2000 m/z) acquired at high mass resolution (60,000 at 400 m/z, AGC target 1×10$^6$, maximum injection time 1,000 ms) in the LTQ linear ion trap (AGC target 5×10$^3$, max inj time 120 ms) from the three most abundant ions. MS$^2$ settings were: collision gas pressure 1.3 mT, normalized collision energy 35%, ion selection threshold of 500 counts, activation q=0.25 and activation time of 30 ms. Fragmented precursor ions that were measured twice within 10 s were dynamically excluded for 60s and ions with z<2 or unassigned were not analyzed. Data from MS$^2$ was validated manually.

LITERATURE CITED IN EXAMPLE 3

(1) Hansen, F. G., Bundgaard, E. & Madsen, R. A short synthesis of (+)-cyclophellitol. *J. Org. Chem.* 70, 10139 (2005)

(2) Tian, W. X., Tsou, C.-L. Determination of the rate constant of enzyme modification by measuring the substrate reaction in the presence of the modifier. *Biochemistry* 21, 1028 (1982)

(3) Baici, A., Schenker, P., Wächter, M. & Rüedi, P. 3-Fluoro-2,4-dioxa-3-phosphadecalins as inhibitors of acetylcholinesterase. A reappraisal of kinetic mechanisms and diagnostic methods. *Chem. Biodivers.* 6, 261 (2009)

(4) Ouchir, H., Mihara, Y. & Takahata, H. A new route to diverse 1-azasugars from N-boc-5-hydroxy-3-piperidene as a common building block. *J. Org. Chem.* 70, 5207, (2005).

(5) Verdoes, M. et al. Acetylene functionalized BODIPY dyes and their application in the synthesis of activity based proteasome probes. *Bioorg. Med. Chem. Lett.* 17, 6169 (2007)

(6) Wennekes, T. et al. Large-scale synthesis of the glucosylceramide synthase inhibitor N[5-(adamantan-1-yl-methoxy)-pentyl]-1-deoxynojirimycin Org. Process. Res. Dev. 12, 414 (2008)

(7) Trott, O. & Olsen, A. J. Autodock vina: improving the speed and accuracy of docking with a new scoring function, efficient optimization, and multithreading. *J. Comput. Chem.* 31, 455 (2010)

(8) Brumshtein, B. et al. Crystal structures of complexes of N-butyl and N-nonyl-deoxynojirimycin bound to acid β-glucosidase: Insights into the mechanism of chemical chaperone action in Gaucher disease. *J. Biol. Chem.* 282, 29052 (2007)

(9) Wessel, D.& Flügge, U. I. A method for the quantitative recovery of protein in dilute-solution in the presence of detergents and lipids. *Anal. Biochem.* 138, 141 (1984).

(10) Rappsilber, J., Mann, M. & Ishihama, Y. Protocol for micro-purification, enrichment, prefractionation and storage of peptides for proteomics using StageTips. *Nat. Protocols* 2, 1896 (2007)

(11) Olsen, J. V. et al. Parts per million mass accuracy on a orbitrap mass spectrometer via lock mass injection into a c-trap. *Mol. Cell. Proteomics* 4, 2010 (2005)

Example 4

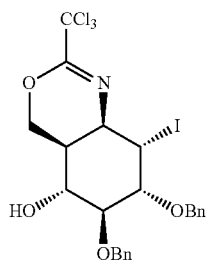

(4aR,5R,6S,7R,8S,8aR)-6,7-bis(benzyloxy)-8-iodo-2-(trichloromethyl)-4a,5,6,7,8,8a-hexahydro-4H-benzo[d][1,3]oxazin-5-ol (MDW977)

Diol xxx (1.33 mg, 3.9 mmol) was coevaporated thrice with toluene and subsequently dissolved in CH$_2$Cl$_2$ (100 mL). The solution was cooled to 0° C., and trichloroacetonitrile (394 µL, 3.9 mmol) and 1,8-diazobicyclo[5.4.0]undec-7-ene (30 µL, 0.2 mmol) was added. After two hours stirring, TLC-analysis revealed complete conversion to a higher running product. To the solution was added H$_2$O (12 mL), sodium hydrogencarbonate (3.2 g, 40 mmol) and iodine (3.04 g, 12 mmol). The resulting mixture was stirred overnight, quenched with Na$_2$S$_2$O$_3$ (aq.) and diluted with CH$_2$Cl$_2$. The layers were separated, after which the organic layer was dried with Na$_2$SO$_4$ and concentrated in vacuo. Silica gel column chromatography (PE→10% EtOAc/PE) afforded title compound xxx (80%, 1.91 g, 3.13 mmol) as a colorless oil. $^1$H NMR (400 MHz, CDCl$_3$) δ 7.38-7.18 (m, 10H), 4.93 (d, J=11.2 Hz, 1H), 4.78 (t, J=3.1 Hz, 1H), 4.74 (d, J=11.0 Hz, 1H), 4.66 (d, J=11.3 Hz, 1H), 4.57 (d, J=11.2 Hz, 1H), 4.48 (d, J=11.3 Hz, 1H), 4.21 (dd, J=11.1, 2.8 Hz, 1H), 4.01-3.98 (m, 1H), 3.37 (dd, J=10.9, 9.3 Hz, 1H), 2.64-2.53 (m, 2H). $^{13}$C NMR (101 MHz, CDCl$_3$) δ 153.35, 138.18, 137.25, 128.64, 128.44, 128.27, 128.06, 127.97, 83.76, 76.44, 75.44, 71.51, 67.85, 67.79, 58.37, 35.92, 33.05.

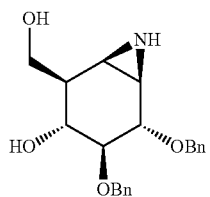 [SMILES: OC[C@@H]1[C@@H](O)[C@H](OCc2ccccc2)[C@@H](OCc2ccccc2)[C@@H]2N[C@H]12]

(1R,2R,3R,4S,5S,6R)-4,5-bis(benzyloxy)-2-(hydroxymethyl)-7-azabicyclo[4.1.0]heptan-3-ol (MDW984)

Imidate xxx (1.91 g, 3.13 mmol) was dissolved in MeOH (80 mL) before being cooled to 0° C. Subsequently, concentrated hydrochloride (4 mL, 37% in H$_2$O) was added and the reaction was stirred at room temperature for 2 h. TLC-analysis revealed the formation of two spots (i.e. the free amine and the corresponding trichloroacetamide). To hydrolyze the formed amide, the mixture was concentrated, redissolved in dioxane (30 mL) and concentrated hydrochloride (10 mL), and stirred at 60° C. After 30 min, LC/MS analysis showed complete conversion to the free amine. The solution was concentrated in vacuo and redissolved in MeOH (80 mL). Sodium hydrogencarbonate (5.26 g, 62.6 mmol) was added. After stirring overnight, celite was added and the solution was filtered over a short path of silica. Purification over silica gel column chromatography (CH$_2$Cl$_2$→5% MeOH/CH$_2$Cl$_2$) afforded title compound xxx (82%, 0.91 g, 2.56 mmol) as a white solid. $^1$H NMR (400 MHz, CDCl$_3$) δ 7.43-7.28 (m, 10H), 4.97 (d, J=11.3 Hz, 1H), 4.80 (d, J=11.4 Hz, 1H), 4.71 (d, J=11.4 Hz, 1H), 4.68 (d, J=11.5 Hz, 1H), 4.00 (dd, J=10.7, 5.6 Hz, 1H), 3.90 (dd, J=10.7, 5.0 Hz, 1H), 3.77 (d, J=8.0 Hz, 1H), 3.53 (t, J=9.9 Hz, 1H), 3.43-3.35 (m, 1H), 2.43 (dd, J=5.9, 3.1 Hz, 1H), 2.26 (d, J=6.0 Hz, 1H), 2.07 (td, J=8.8, 5.1 Hz, 1H). $^{13}$C NMR (101 MHz, CDCl$_3$) δ 138.60, 137.92, 128.56, 128.49, 127.95, 127.89, 127.76, 84.50, 81.23, 74.77, 72.25, 68.18, 64.26, 42.68, 33.07, 31.67. LC/MS: R$_t$ 5.74; linear gradient 10→90% B in 13.5 min; ESI/MS: m/z=355.93 (M+H)$^+$.

(1R,2S,3S,4R,5R,6R)-5-(hydroxymethyl)-7-azabicyclo[4.1.0]heptane-2,3,4-triol (MDW1023)

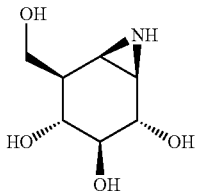 [SMILES: OC[C@@H]1[C@@H](O)[C@H](O)[C@@H](O)[C@@H]2N[C@H]12]

Ammonia (10 mL) was condensed at −60° C. Lithium (70 mg) was added and the mixture was stirred until the lithium was completely dissolved. To this solution was added a solution of aziridine xxx (158 mg, 0.445 mmol) in THF (10 mL). The mixture was stirred for 2 h at −50° C. and subsequently quenched with MeOH/H$_2$O. The solution was heated to room temperature and stirred until all ammonia had evolved. Next, the solution was concentrated in vacuo, redissolved in H$_2$O and neutralized with Amberlite H$^+$. Product bound to the resin was eluted with Et$_3$N/MeOH/H$_2$O. Evaporation under reduced pressure gave title compound xxx (quant, 78 mg, 0.445 mmol). $^1$H NMR (400 MHz, MeOD) δ 4.02 (dd, J=10.3, 4.3 Hz, 1H), 3.74-3.65 (m, 1H), 3.61 (d, J=8.2 Hz, 1H), 3.20 (dd, J=10.0, 8.2 Hz, 1H), 3.05 (t, J=9.9 Hz, 1H), 2.59 (dd, J=5.8, 3.2 Hz, 1H), 2.28 (d, J=6.0 Hz, 1H), 2.03-1.93 (m, 1H). $^{13}$C NMR (101 MHz, MeOD) δ 77.80, 72.64, 67.93, 62.28, 43.96, 34.98, 32.60.

1-((1R,2S,3S,4R,5R,6R)-2,3,4-trihydroxy-5-(hydroxymethyl)-7-azabicyclo[4.1.0]heptan-7-yl)hept-6-yn-1-one

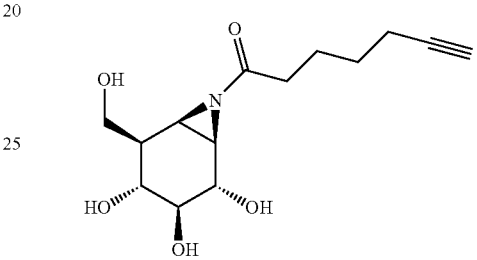

Aziridine xxx (10 mg, 57 mmol) was dissolved in DMF (1 mL). A solution of EEDQ ( . . . μL, 250 mmol) and hept-7-ynoic acid ( . . . μL, 250 μmol) in DMF (250 μL) was added. After overnight stirring, TLC-analysis showed incomplete conversion and an additional amount of EEDQ and hept-7-ynoic acid was added. After 1 h, the reaction was concentrated under reduced pressure. Silica gel column chromatography (CH$_2$Cl$_2$ 10% MeOH/CH$_2$Cl$_2$) afforded acetylated aziridine xxx (52%, 8.42 mg, 30 mmol). $^1$H NMR (400 MHz, MeOD) δ 4.09 (dd, J=10.3, 4.4 Hz, 1H), 3.71 (dd, J=13.5, 5.7 Hz, 2H), 3.37 (s, 1H), 3.23 (dd, J=10.0, 8.1 Hz, 1H), 3.10 (t, J=9.9 Hz, 1H), 3.06 (dd, J=5.8, 2.9 Hz, 1H), 2.76 (d, J=5.8 Hz, 1H 2.55 (td, J=7.2, 1.7 Hz, 2H), 2.26-2.17 (m, 3H), 2.06-1.95 (m, 1H), 1.81-1.70 (m, 2H), 1.63-1.51 (m, 2H). $^{13}$C NMR (101 MHz, MeOD) δ 77.67, 71.98, 68.37, 67.92, 62.13, 43.85, 41.06, 39.69, 34.94, 27.75, 23.75, 17.40.

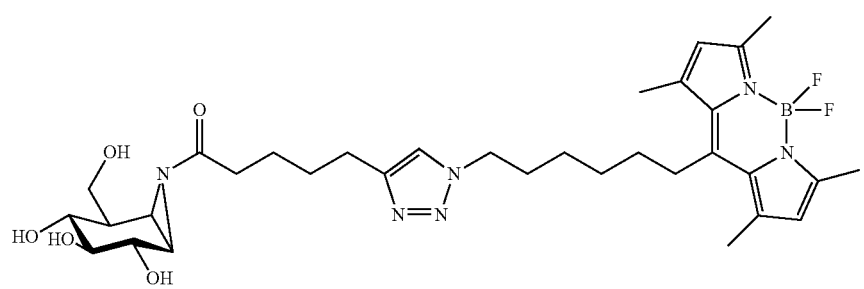

MDW1044

Alkyne xxx (5 mg, 17 mmol) was dissolved in DMF (0.75 mL). Bodipyazide xxx (7.1 mg, 19 mmol), CuSO$_4$ (2 μL of 1M solution in H$_2$O) and sodium ascorbate (3 μL of 1M solution in H$_2$O) were added and the solution was stirred overnight. The volatiles were removed under reduced pressure and the product was purified by silica gel column chromatography (CH$_2$Cl$_2$→10% MeOH/CH$_2$Cl$_2$) and by semi preparative reversed phase HPLC (linear gradient: 42%→51%, 3CV, solutions used: A: ammonium acetate in H$_2$O, B: acetonitrile). Use ammonium acetate.

MDW969

Azido-bodipy xxx (25 mg, 52 mmol) was dissolved in toluene (5 mL). Trimethyltin hydroxide (35 mg, 114 mmol) was added and the reaction was refluxed overnight. Next, the solution was diluted with toluene, washed with HCl (3×), dried over Na$_2$SO$_4$, and concentrated under reduced pressure. The resulting free acid was dissolved in DMF (2 mL). Subsequently, biotin-alkyne (17 mg, 60 mmol), CuSO$_4$ (6 μL 1M in H$_2$O, 6 mmol) and sodium ascorbate (9 μL 1M in H$_2$O, 9 mmol). TLC-analysis revealed complete conversion after 2 h. The mixture was diluted with CH$_2$Cl$_2$, washed with 1M HCl (aq.) and dried over Na$_2$SO$_4$. Removal of the volatiles under reduced pressure afforded biotin-bodipy xxx (quant, 48 mg, 52 mmol).

MDW970

Biotin-bodipy xxx (48 mg, 52 μmol) was dissolved in DMF (2 mL) and subsequently, EDC (19 mg, 0.1 mmol), HOBt (13.5 mg, 0.1 mmol) and propargylamine (10 μL, 0.15 mmol) were added. LC/MS analysis revealed complete conversion. The solution was diluted with CH$_2$Cl$_2$, washed with 1M HCl (aq.), NaHCO$_3$ (aq.), dried over Na$_2$SO$_4$ and concentrated in vacuo.

Purification over silica gel column chromatography (CH$_2$Cl$_2$ 10% MeOH/CH$_2$Cl$_2$) gave biotin-bodipy-alkyne xxx (38%, 16 mg, 20 μmol). $^1$H NMR (400 MHz, CDCl$_3$/MeOD) δ 7.86 (d, J=8.8 Hz, 2H), 7.76 (s, 1H), 7.27 (s, 1H), 7.03 (d, J=4.1 Hz, 1H), 6.94 (d, J=8.8 Hz, 2H), 6.57 (d, J=4.1 Hz, 1H), 4.60 (t, J=6.8 Hz, 2H), 4.52-4.38 (m, 3H), 4.25 (dd, J=7.8, 4.5 Hz, 1H), 4.04 (t, J=5.7 Hz, 2H), 3.93 (d, J=2.5 Hz, 2H), 3.38 (s, 1H), 3.17-3.09 (m, 1H), 2.88 (dd, J=12.8, 5.0 Hz, 1H), 2.75 (t, J=7.6 Hz, 2H), 2.70 (d, J=12.8 Hz, 1H), 2.52 (s, 3H), 2.46-2.37 (m, 3H), 2.34 (t, J=7.5 Hz, 2H), 2.24 (s, 3H), 2.21 (t, J=7.4 Hz, 2H), 1.75-1.51 (m, 5H), 1.40 (m, 3H). $^{13}$C NMR (101 MHz, CDCl$_3$/MeOD) δ 177.48, 174.46, 172.93, 164.44, 159.53, 159.20, 154.94, 144.96, 140.46, 135.05, 134.48, 130.56, 130.41, 127.91, 125.90, 123.20, 117.98, 113.99, 70.95, 64.20, 61.90, 60.17, 55.60, 47.21, 40.01, 35.45, 35.33, 34.42, 29.63, 28.48, 28.32, 28.02, 25.31, 19.96, 12.48, 8.87.

MDW971

Biotin-bodipy-alkyne xxx (11 mg, 14 μmol) and azidocyclophellitol (2.82 mg, 14 μmol) were dissolved in DMF (0.75 mL). CuSO$_4$ (2 μL, 1M in H$_2$O, 2 μmol) and sodium ascorbate (3 μL, 1M in H$_2$O, 3 μmol) were added and the resulting mixture was stirred overnight. TLC-analysis showed incomplete conversion and an additional amount of CuSO$_4$ and sodium ascorbate was added. After 2 h stirring, the volatiles were removed under reduced pressure and the resulting crude product was purified by silica gel column chromatography (CH$_2$Cl$_2$→20% MeOH/CH$_2$Cl$_2$). Title compound xxx (89%, 12.26 mg, 12.4 μmol) was obtained as a purple solid. $^1$H NMR (400 MHz, MeOD) δ 7.86 (d, J=8.9 Hz, 2H), 7.76 (s, 1H), 7.61 (s, 2H), 7.26 (s, 1H), 7.04 (d, J=4.1 Hz, 1H), 6.94 (d, J=8.9 Hz, 2H), 6.58 (d, J=4.1 Hz, 1H), 4.61 (t, J=6.8 Hz, 2H), 4.51-4.45 (m, 2H), 4.44-4.39 (m, 4H), 4.25 (dd, J=7.8, 4.5 Hz, 1H), 4.04 (t, J=5.7 Hz, 2H), 3.65 (d, J=8.2 Hz, 1H), 3.37 (s, 3H), 3.23 (dd, J=9.9, 8.3 Hz, 1H), 3.17-3.06 (m, 2H), 3.03 (d, J=3.7 Hz, 1H), 2.98 (d, J=2.4 Hz, 1H), 2.88 (dd, J=12.8, 5.0 Hz, 1H), 2.76 (t, J=7.4 Hz, 2H), 2.70 (d, J=12.8 Hz, 1H), 2.50 (s, 3H), 2.46-2.31 (m, 5H), 2.25-2.16 (m, 5H), 1.75-1.51 (m, 5H), 1.44-1.35 (m, 3H). $^{13}$C NMR (101 MHz, MeOD) δ 174.46, 173.10, 164.41, 159.54, 159.23, 155.07, 144.95, 140.46, 134.37, 130.60, 130.37, 128.08, 125.84, 123.64, 123.25, 118.11, 114.04, 76.79, 70.94, 67.26, 64.20, 61.89, 60.16, 56.30, 55.60, 54.20, 49.57, 47.24, 43.05, 40.06, 35.50, 35.34, 34.47, 34.42, 29.63, 29.51, 28.31, 28.02, 25.30, 19.98, 12.55, 8.92.

Biotin-Cyclophellitol (MDW997)

Biotin-alkyne xxx (5 mg, 18 μmol) and azidocyclophellitol (3.4 mg, 17 μmol) were dissolved in DMF (0.75 mL). CuSO$_4$ (4 μL, 1M in H$_2$O, 4 μmol) and sodium ascorbate (6 μL, 1M in H$_2$O, 6 μmol) were added and the resulting mixture was stirred overnight. TLC-analysis showed complete conversion to a very polar product. The volatiles were removed under reduced pressure. Purification by RP-HPLC (linear gradient 7%→16% B in 15 min) yielded biotin-cyclophellitol xxx (83%, 6.80 mg, 14.1 μmol) as a white amorphous solid.

The invention claimed is:

1. An activity based probe (ABP) comprising a glycosidase inhibitor and a detection-group, wherein the glycosidase inhibitor covalently binds to a glycosidase and/or a glycosidase fusion protein, wherein said glycosidase inhibitor is a glucocerebrosidase inhibitor selected from at least one group consisting of

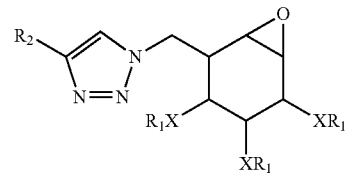

R1=Hydrogen, Carbohydrate, Alkyl, Aromate, Amide, biotin, fluorophore
R2=Alkyl, Aromate, Biotin, Fluorophore
X=O, N, S

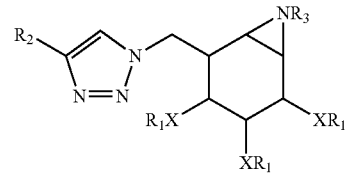

R1=Hydrogen, Carbohydrate, Alkyl, Aromate, Amide, biotin, fluorophore
R2=Alkyl, Aromate, Biotin, Fluorophore
R3=Amide, Alkyl, or Fluorophore
X=O, N, S
or

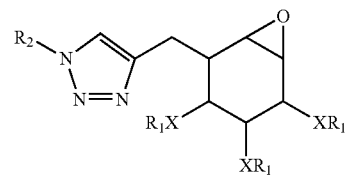

-continued

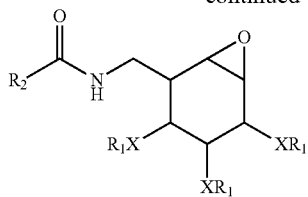

$R_1$=Hydrogen, Carbohydrate, Alkyl, Aromate, Amide, biotin, fluorophore
$R_2$=Alkyl, Aromate, Biotin, Fluorophore
X=O, N, S
or

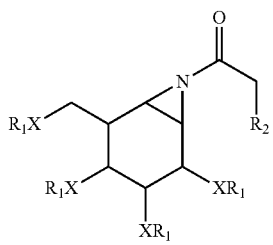

$R_1$=Hydrogen, Carbohydrage, Alkyl, Aromatic, Amide
$R_2$=alkyl, aromatic, Azide, alkyne, biotin, fluorophore
X=O, N, S
or

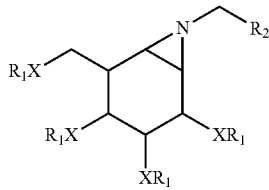

$R_1$=Hydrogen, Carbohydrage, Alkyl, Aromatic, Amide
$R_2$=alkyl, aromatic, azide, alkyne, biotin, fluorophore
X=O, N, S.

2. The ABP according to claim 1, wherein said detection group is a fluorophore or biotin.

3. An ABP according to claim 1, capable of being used in detecting and/or quantifying activity of an active enzyme, for screening of a compound for use thereof in treating and/or preventing a storage disease which is optionally Gaucher disease, and/or for visualizing a glycosidase fusion protein.

4. The ABP according to claim 3, capable of being used in detecting a storage disease.

5. The ABP according to claim 3, wherein said compound capable of being used in preventing and/or treating a storage disease is a chaperone.

6. The ABP of claim 1, wherein said glycosidase inhibitor comprises cyclophellitol.

7. A kit comprising an ABP according to claim 1, for determining an active enzyme optionally comprising glycosidase, and/or for screening of a therapeutic for use thereof in preventing and/or treating a storage disease.

8. A kit comprising an ABP according to claim 1, for labeling of a therapeutic glycosidase, which visualizes, targeting and/or stability of the therapeutic glycosidase.

9. A kit according to claim 8, wherein said labeling is selected depending on pH and/or calcium concentration in a cell or cell environment.

10. A method for producing an ABP according to claim 1, said method comprising chemically modifying said glycosidase inhibitor and linking said glycosidase inhibitor to a detection-group.

11. The method for producing an ABP according to claim 10, wherein said glycosidase inhibitor is cyclophellitol, which is physically linked to a fluorophore or biotin.

12. The method for producing an ABP according to claim 11, wherein azido-cyclophellitol is linked to a fluorophore or biotin.

13. A method for detecting an ABP according to claim 1, said method comprising:
    binding said ABP to a glycosidase and/or a glycosidase-fusion protein, and
    detecting the bound ABP via the detection group, optionally wherein said detection group comprises a fluorophore or biotin.

* * * * *